US009625463B2

(12) United States Patent
Miltenyi et al.

(10) Patent No.: US 9,625,463 B2
(45) Date of Patent: *Apr. 18, 2017

(54) SYSTEM FOR SEPARATING A CELL SAMPLE BY CENTRIFUGATION AND COLUMN CHROMATOGRAPHY WHILE MAINTAINING STERILITY

(71) Applicant: Miltenyi Biotec GmbH, Bergisch Gladbach (DE)

(72) Inventors: Stefan Miltenyi, Bergisch Gladbach (DE); Winfried Schimmelpfennig, Krakow am See (DE); Holger Lantow, Rostock (DE); Niklas Elmar Neuschaefer, Rostock (DE); Martin Biehl, St. Wendel (DE); Eiad Kabaha, Bonn (DE); Juergen Schulz, Jesteburg (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/181,023

(22) Filed: Feb. 14, 2014

(65) Prior Publication Data
US 2014/0370592 A1 Dec. 18, 2014

Related U.S. Application Data

(62) Division of application No. 12/745,688, filed as application No. PCT/IB2008/003823 on Dec. 8, 2008, now Pat. No. 8,727,132.
(Continued)

(51) Int. Cl.
*B01L 1/00* (2006.01)
*C12M 1/00* (2006.01)
(Continued)

(52) U.S. Cl.
CPC ........... *G01N 33/58* (2013.01); *A61M 1/3679* (2013.01); *A61M 1/3693* (2013.01);
(Continued)

(58) Field of Classification Search
CPC .. A61M 2202/0427; A61M 2202/0413; A61M 1/3693; C12M 33/10; B01D 21/26; B04B 5/10; B04B 13/00
See application file for complete search history.

(56) References Cited

U.S. PATENT DOCUMENTS 3,586,413 A 6/1971 Adams
3,955,755 A 5/1976 Breillatt et al.
(Continued)

FOREIGN PATENT DOCUMENTS

EP 0016552 A 10/1980
EP 0535618 A1 4/1993
(Continued)

OTHER PUBLICATIONS

English translation of DE 10127068, Bahr et al.*
(Continued)

*Primary Examiner* — Nathan Bowers
(74) *Attorney, Agent, or Firm* — Kilpatrick Townsend and Stockton LLP

(57) ABSTRACT

The invention relates to a system, comprising: a) a sample processing unit, comprising an input port and an output port coupled to a rotating container having at least one sample chamber, the sample processing unit configured provide a first processing step to a sample or to rotate the container so as to apply a centrifugal force to a sample deposited in the chamber and separate at least a first component and a second component of the deposited sample; and b) a sample separation unit coupled to the output port of the sample processing unit, the cell separation unit comprising separation
(Continued)

column holder (42), a pump (64) and a plurality of valves (1-11) configured to at least partially control fluid flow through a fluid circuitry and a separation column (40) positioned in the holder, the separation column configured to separate labeled and unlabeled components of sample flowed through the column.

23 Claims, 40 Drawing Sheets

Related U.S. Application Data

(60) Provisional application No. 61/012,361, filed on Dec. 7, 2007.

(51) Int. Cl.

| | | |
|---|---|---|
| *G01N 33/58* | (2006.01) | |
| *A61M 1/36* | (2006.01) | |
| *B03C 1/28* | (2006.01) | |
| *B04B 5/04* | (2006.01) | |
| *B04B 13/00* | (2006.01) | |
| *C12M 1/26* | (2006.01) | |
| *B01D 21/26* | (2006.01) | |
| *B04B 5/00* | (2006.01) | |
| *B04B 5/10* | (2006.01) | |
| *B04B 1/12* | (2006.01) | |
| *B04B 7/08* | (2006.01) | |
| *G01N 35/00* | (2006.01) | |
| *B01D 15/38* | (2006.01) | |
| *C12N 5/0789* | (2010.01) | |
| *C12N 5/077* | (2010.01) | |
| *C12N 5/0783* | (2010.01) | |

(52) U.S. Cl.
CPC ..... *B01D 15/3809* (2013.01); *B01D 15/3885* (2013.01); *B01D 21/26* (2013.01); *B03C 1/288* (2013.01); *B04B 1/12* (2013.01); *B04B 5/00* (2013.01); *B04B 5/04* (2013.01); *B04B 5/0442* (2013.01); *B04B 5/10* (2013.01); *B04B 7/08* (2013.01); *B04B 13/00* (2013.01); *C12M 33/10* (2013.01); *C12M 47/04* (2013.01); *C12N 5/0636* (2013.01); *C12N 5/0646* (2013.01); *C12N 5/0647* (2013.01); *C12N 5/0669* (2013.01); *G01N 35/0098* (2013.01); *A61M 2202/0071* (2013.01); *A61M 2202/0413* (2013.01); *A61M 2202/0427* (2013.01); *B04B 2005/0464* (2013.01); *B04B 2013/006* (2013.01); *G01N 2333/70596* (2013.01)

(56) References Cited

U.S. PATENT DOCUMENTS

| | | |
|---|---|---|
| 4,321,330 A | 3/1982 | Baker et al. |
| 4,632,908 A | 12/1986 | Schultz |
| 5,260,598 A | 11/1993 | Brass et al. |
| 5,316,667 A | 5/1994 | Brown et al. |
| 5,691,208 A | 11/1997 | Miltenyi et al. |
| 5,904,840 A | 5/1999 | DiBella |
| 6,080,581 A | 6/2000 | Anderson et al. |
| 6,709,377 B1 | 3/2004 | Rochat |
| 2002/0144939 A1 | 10/2002 | Dolecek |
| 2002/0173034 A1 | 11/2002 | Barbera-Guillem et al. |
| 2003/0040104 A1 | 2/2003 | Barbera-Guillem |
| 2004/0209755 A1* | 10/2004 | Moore et al. ............ 494/20 |
| 2005/0051466 A1 | 3/2005 | Carter et al. |
| 2007/0102374 A1 | 5/2007 | Kolenbrander |
| 2010/0311559 A1 | 12/2010 | Miltenyi et al. |
| 2011/0003380 A1 | 1/2011 | Miltenyi et al. |

FOREIGN PATENT DOCUMENTS

| | | |
|---|---|---|
| EP | 0654669 A2 | 5/1995 |
| EP | 2227334 B1 | 10/2011 |
| WO | 90/04019 A | 4/1990 |
| WO | 02/094351 A2 | 11/2002 |

OTHER PUBLICATIONS

International Search Report for PCT Application No. PCT/IB2008/003845 mailed Jun. 26, 2009.
International Search Report for PCT Application No. PCT/IB2008/003823 mailed Jul. 30, 2009.
Sugai et al., "Fresenius AS.TEC204 Blood Bell Separator," Therapeutic Apheresis and Dialysis 7(1): 37-43 (2003).
Granzin et al., "Fully automated expansion and activation of clinical-grade natural killer cells for adoptive immunotherapy", Cytotherapy, Mar. 2015; vol. 17: pp. 621-632.
Kumaresan et al., "Automating the Manufacture of Clinically Appealing Designer T Cells", Treatment Strategies, Blood & Marrow Transplantation, vol. 1, Issue 1, May 2014, 7 pages.
Miltenyi Biotec, "The way to integrated cell processing—25 years of development and innovation at Miltenyi Biotec", Excerpt from MACS&more vol. 16, Jan. 2014, 4 pages.
Miltenyi Biotec, Press Release, Now FDA approved—The CliniMACS CD34 Reagent System, accessed via www.miltenyibiotec.com/en/clinical-applications/Ip_clinimacs_system_fda_slider.aspx on Jan. 8, 2016, 2 pages.
Miltenyi Biotec, Product Guide for CliniMACS Prodigy System, accessed at www.miltenyibiotec.com/local on Jan. 8, 2016, 14 pages.
Miltenyi Biotec, Product Guide for The CliniMACS Prodigy, accessed at www.miltenyibiotec.com/local on Jan. 8, 2016, 2 pages.
Spohn et al., "Automated CD34+ cell isolation of peripheral blood stem cell apheresis product", Cytotherapy, Oct. 2015; vol. 17: pp. 1465-1471.
European Search Report and Written Opinion for EP Application No. EP11193362 dated Jul. 26, 2013, 8 pages.
European Search Report and Written Opinion for EP Application No. EP12178904 dated Jul. 16, 2013, 5 pages.

\* cited by examiner

SYSTEM FOR SEPARATING A CELL SAMPLE BY CENTRIFUGATION AND COLUMN CHROMATOGRAPHY WHILE MAINTAINING STERILITY

REFERENCE TO RELATED APPLICATIONS

This application is a divisional of U.S. application Ser. No. 12/745,688, which is the U.S. National Stage of PCT/IB08/03823, filed Dec. 8, 2008, and having a §371(c)(1) date of Aug. 20, 2010, which claims priority to U.S. Provisional Application 61/012,361, filed Dec. 7, 2007. The PCT application and U.S. National Stage application are hereby incorporated herein by reference in their entirety for all purposes.

BACKGROUND OF THE INVENTION

A variety of human diseases currently cannot be treated in a satisfactory manner with standard pharmaceuticals, proposing the use of primary human cells as an alternative or additional option for the treatment of various diseases. Those cellular therapy approaches usually require significant handling and processing of cellular products to separate wanted from unwanted functions, for example depletion of cells in an unwanted and potentially life threatening graft versus host reaction or enrichment of cells involved in wanted graft versus leukemia/tumor effects.

Methods known in the art require a massive infrastructure in hospitals to fulfill regulatory and safety requirements, including good manufacturing procedures compatible clean rooms and personnel to maintain rooms, devices, production, quality control and quality assurance procedures. Cellular products are usually processed utilizing a combination of different devices and disposables with manual transfer of samples between those systems.

The current invention integrates various cell processing steps into a single device and disposable, controlled in a fully automated process, eliminating the requirements for manual cell transfer, in-process controls, related risks to the cellular product, and risk reduction measures and thus provides a device and method for manufacturing of cellular therapy products that are ready for direct use. The cellular product manufactured using the system of the present invention will typically be ready for direct transfer into the patient.

The present invention is generally related to processing of biological materials. More specifically, the present invention provides systems, devices, and methods for the processing of biological materials to culture and/or separate components of a biological sample, and to further separate components of the sample by separation techniques, including application of magnetic separation.

Various techniques are known for separating components of a sample or biological material that make use of separation techniques. Such techniques include but are not limited to panning, magnetic separation, centrifugation, filtration, immunoaffinity separation, gravitation separation, density gradient separation, and elutriation.

Immunoaffinity methods may include selective labeling of certain components of a sample (e.g., antibody labeling) and separation of labeled and unlabeled components. Magnetic separation methods typically include passing the sample through a separation column.

Magnetic separation is a procedure for selectively retaining magnetic materials in a chamber or column disposed in a magnetic field. A target substance, including biological materials, may be magnetically labeled by attachment to a magnetic particle by means of a specific binding partner, which is conjugated to the particle. A suspension of the labeled target substance is then applied to the chamber. The target substance is retained in the chamber in the presence of a magnetic field. The retained target substance can then be eluted by changing the strength of, or by eliminating, the magnetic field.

A matrix of material of suitable magnetic susceptibility may be placed in the chamber, such that when a magnetic field is applied to the chamber a high magnetic field gradient is locally induced close to the surface of the matrix. This permits the retention of weakly magnetized particles and the approach is referred to as high gradient magnetic separation (HGMS).

The use of HGMS in biological separations requires that the conditions provide a high yield with substantial purity. Accordingly, it would be desirable to provide high gradient magnetic separators, devices and methods that are relatively easy to construct and use, yet provide maximized and uniform magnetic field gradients and flow characteristics during use. It would be most advantageous if such magnetic separators, devices and methods could be used to perform a variety of cell sorting or assay procedures with the selection of the appropriate specific binding member by which the target substance will be magnetically labeled.

In many instances, separation methodologies must be performed under conditions that ensure non-contamination of the sample or maintain sterility. For example, many current clinical cell separation systems need to be operated in clean rooms of high quality in order to maintain sterility of samples. Often ensuring non-contamination is cumbersome, expensive and requires separate facilities and personnel, as well as complex procedures requiring extensive efforts to maintain reproducibility and sterility. Additionally, numerous processing and handling steps (e.g., washing, volume reduction, etc.) must be performed separate from the separation systems with subsequent introduction of the processed samples as well as attachment of fluids and reagents to the systems, further complicating sterility compliance. As such, improved methods and systems are needed to ensure non-contamination of samples and/or reducing the complexity and expense of sample processing.

BRIEF SUMMARY OF THE INVENTION

The present invention provides a sample processing and separation system including a sample processing unit and a sample separation unit.

In one embodiment, the invention provides improvements in high gradient magnetic separation devices, apparatus and methods for the separation of biological materials. The subject devices, apparatus and methods allows a greater specificity and efficiency in the isolation of particular cells, proteins, polysaccharides, and other biological materials, or other materials that are magnetic or are capable of a specific binding interaction with a magnetically labeled binding member.

A magnetic separation column is provided, having a nonmagnetic housing that defines a separation chamber, and a fluid permeable matrix of e.g. metallic spheres within the chamber. The spheres form a closely stacked lattice, which creates substantially uniform channels for homogeneous flow during separations. A magnetic separator device may use the separation column in conjunction with a prefilter device. The device may be used in an instrument having a permanent or electromagnet for use during separations, with an optional retractable arm for moving the magnet, pumping means for washing and separating the target material, and a microprocessor for controlling the separation fluid flow.

In one embodiment, the system comprises a) a sample processing unit comprising an input port and an output port coupled to a rotating container (or centrifugation chamber) having at least one sample chamber, wherein the sample processing unit is configured to provide a first processing step to a sample or to rotate the container so as to apply a centrifugal force to a sample deposited in the chamber and separate at least a first component and a second component of the deposited sample; and b) a sample separation unit coupled to the output port of the sample processing unit, the sample separation unit comprising a separation column holder, a pump, and a plurality of valves configured to at least partially control fluid flow through a fluid circuitry and a separation column positioned in the holder, wherein the separation column is configured to separate labeled and unlabeled components of sample flowed through the column.

It is preferred that the rotating container comprises a means for detecting the progress of separation of the at least first component and the second component of the deposited sample in the rotating container.

The means for detecting the progress of separation can be located such that light from a light source can at least partially penetrate through at least a part of the sample that is being separated, and light passing through at least a part of the sample can be detected by a light detector.

Preferably, the means for detecting the progress of separation can be located at the rotating container, essentially perpendicular to a rotation axis of the rotating container.

It is further preferred that the means for detecting the progress of separation is positioned at the rotating container reaching essentially from an area adjacent to the rotation axis of the rotating container to an area adjacent to the perimeter of the rotating container.

The means for detecting the progress of separation in the rotating container can be a window, a prism or a mirror. The window, prism or mirror can be positioned to cover a channel formed in the lid or the bottom of the rotating container, wherein the channel is configured such that at least a part of the sample can flow into the channel during centrifugation. A window can also be used without a channel, i.e. the separation of the sample is then detected through a window in the lid or the bottom of the rotating chamber.

Preferably, the rotating container is configured such that it is usable for culturing cells. In that case, the rotating container preferably comprises at least one layer for growing cells thereon. The at least one layer can be positioned perpendicular to a rotation axis. It is preferred to arrange a plurality of layers for growing cells thereon in the rotating container.

The rotating container can be manufactured in a disposable form. It is also preferred that the rotating container can be sterilized to allow cell processing without contamination.

In particular, the rotating container comprises or can be made of a material chosen from the group consisting of: plastics, polystyrol (PS), polysterene, polyvinylchloride, polycarbonate, glass, polyacrylate, polyacrylamide, polymethylmethacrylate (PMMA), polyethylenterephtala (PET), polytetrafluorethylen (PTFE), thermoplastic polyurethane (TPU), silicone The chamber can also be made of polyethylene (PE), collagen, chitin, alginate, hyaluronic acid derivatives, polyactide (PLA), olyglycolida (PGA) and their copolymers, polystyrol (PS), polysterene, polycarbonate, polyacrylate, ceramics, glass materials, like hydroxylapatite (HA), and calcium phosphate, and compositions comprising one or more of the above mentioned materials.

Input and output ports typically comprise at least one sterile filter.

Furthermore, the invention relates to a method, comprising or containing the following steps:
a) providing a system as described above and herein; b) performing a first processing step to separate at least a first component and a second component of a sample; and c) performing a sample separation step to a processed component of the sample, the separation comprising separating labeled and unlabeled components from the processed sample component. The processing step can also be performed after the separation step.

Due to the presence of the rotating chamber in the system as described above and herein, it is preferred that the method comprises detecting the progress of separation, in particular by detecting the formation of layers of the sample, the change of pH value, and/or the change of temperature.

The method can preferably be performed when the sample is a biological sample, in particular, blood or bone marrow.

Furthermore, the invention relates to a computer program, in particular when executed on a computer, for controlling a system as described above and herein, in particular for performing a method as described above and herein. The computer program can be stored on a storage means, such as a floppy disk.

The invention further relates to an integrated cell processing instrument comprising a housing, at least one magnet unit for disposable magnetic separation chamber, at least one drive for a disposable centrifuge/culture chamber, various pinch valves arranged such that different arrangements of a disposable tubing set can be mounted onto the instrument. Further, the instrument may comprise a user interface with integrated monitor and/or computer for storing and performing different cell processing operations. For this purpose, at least one pump driver can be operated using the computer. An optical detection system for a centrifuge for measuring optical densities in different positions in the chamber can be present. The centrifuge chamber can be disposable and located in a temperature controlled area. Means for adjusting the temperature of the fluid moving to the chamber can be present (heater, cooler). A cell culture camera may be positioned at the rotating container, preferentially located at bottom, possibly with means for adjusting the focus of the camera.

The invention further relates to disposable sterile tubing set for sterile cell processing for use with the system of the invention. Typically, a sample bag or port for starting cells is provided. The tubing and/or the system can be configured to allow direct transfer of cell from patient to a sample bag. Further, the following can be part of the tubing and/or system: a different input port for buffer cell culture media, at last one input port magnetic labeling reagent, input ports typically with sterile filter(s), an output port for waste, and/or an output port for cells. The output port can be directly connected with cell freezing bags. Further, an output port can be directly connected with container for transfusion and/or injection.

BRIEF DESCRIPTION OF THE DRAWINGS

FIG. 20 shows unprocessed bone marrow (A, C) and CD133 selected cells (B, D).

FIG. 21 shows unprocessed apheresis product (A, B) and CD14 enriched product (C, D).

FIG. 22 shows unprocessed apheresis harvest (left) and enriched PDCs (right).

FIG. 23 shows CD4 selection using the present invention, unprocessed buffy coat (left), CD4 enriched target cells (right).

FIG. 24 shows Buffy coat cells before (left) and after (right) CD8 depletion using the present invention.

FIG. 25 shows growth of K562 cell line in centrifuge chamber.

FIG. 26 shows unprocessed bone marrow (left) and CD34 or CD133 selected cells after direct elution in 20 ml (right).

FIG. 27 shows unprocessed bone marrow (left) and CD34 or CD133 selected cells after direct elution in small volume of 6 ml (right).

FIG. 28 shows unprocessed bone marrow (left) and CD34 or CD133 selected cells after final volume reduction by filter (right).

FIG. 29 shows unprocessed bone marrow (left), CD34 or CD133 selected cells after direct elution in 20 ml (middle) and after final volume reduction by AutoMACS column.

DETAILED DESCRIPTION OF THE INVENTION

Figure 1:
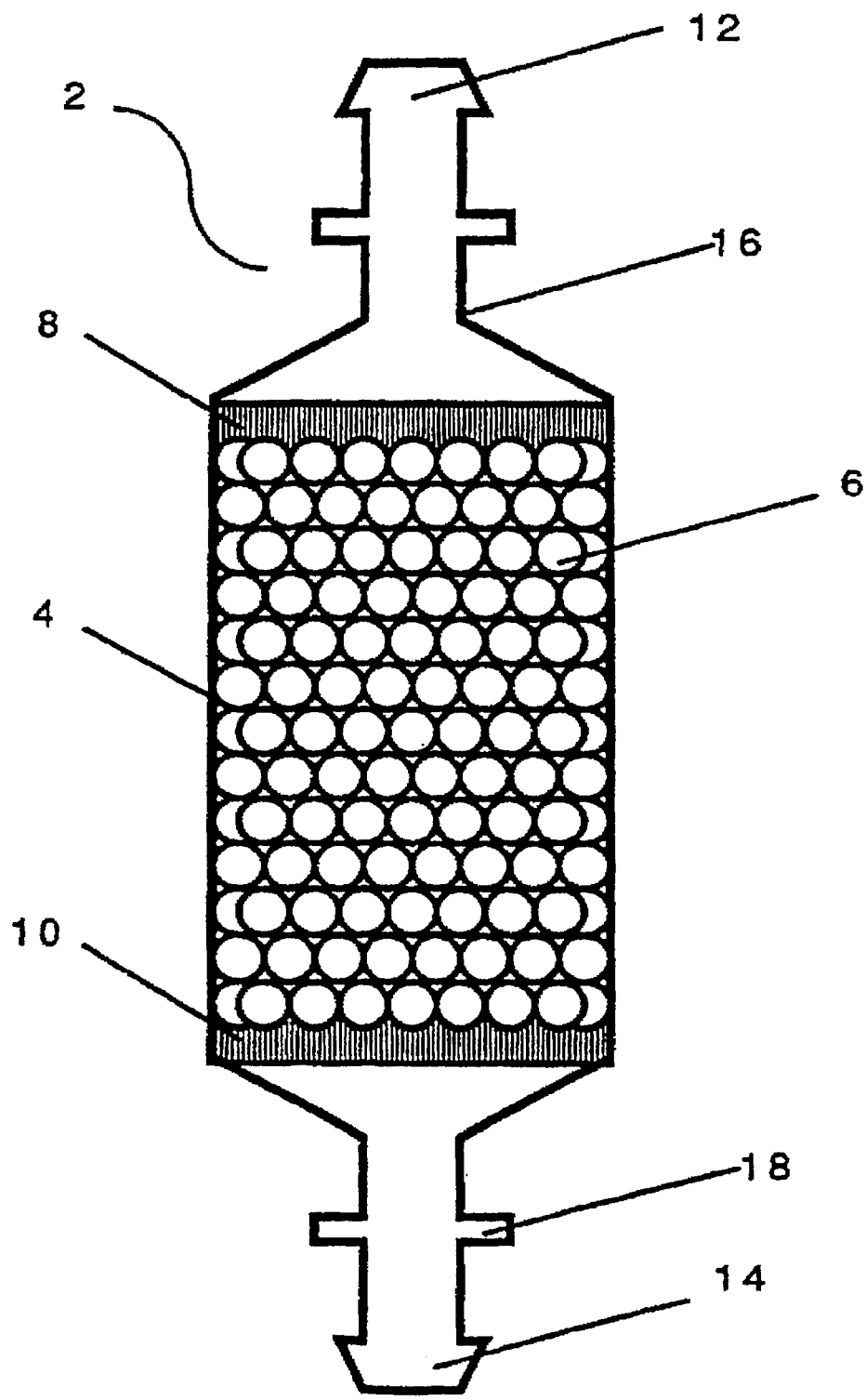
FIG. 1 is a schematic diagram of an exemplary separation or prefiltration column of the present invention.

The present invention provides sample processing systems that integrate both sample separation systems and sample processing techniques. A system can include a sample processing unit configured to perform certain processing steps prior to separation methods, such as magnetic based separation, cell culture or cell manipulation. As such, the present invention can include a combined sample processing system and sample separation system. Sample processing systems or units can provide sample processing such as cell culturing, washing, preparation, incubation, labeling and the like. Additionally, sample processing systems/units can include centrifugation based separation techniques, where a centrifugal force is applied to a sample so as to separate at least a first component and a second component from a sample.

Thus, a system of the present invention will typically include both a sample processing unit and a sample separation unit. The system may also comprise or contain a plurality of sample processing units and/or a plurality of sample separation units. The combined processing/separation system of the invention can include a closed system that can be programmed to automatically perform a variety of complex cell processing steps, including density based separations, immunoaffinity separation, magnetic including immuno-magnetic separations, cell cultivation/stimulation/activation, washing or final formulation steps. For this purpose, the system may be controlled by a computer program that can be run on a computer. The cell processing steps also may include delivery of certain substances to the cells, including cytokines, genetic materials as DNA, RNA, viruses, transcription factors, antigens or other chemical substances.

The invention provides a system that minimizes errors of the user, maintains sterility, performs complex cell processing steps with little or no manual interaction required, and minimizes operator exposure when processing infectious material. Processing at bedside or in a surgical room is possible. The device can be operated while connected to a patient from which a sample is being obtained or to whom a processed sample or fractions thereof are administered. E.g., bone marrow obtained from a patient may be processed directly into an input bag of the tubing set. From there, the e.g. bone marrow can be processed, i.e. separated into at least two components. At least one of these components may be administered to the patient, possibly after processing the component in a suited way.

Density based separation processes performed with the sample processing unit of the inventive system including, without limitation, cell washing, buffy coat generation, density based separation using density media, e.g. Ficoll™, Percoll™ (GE Healthcare), separation based on density labeling (e.g. Rosettesep (Stem Cell technologies), or other density labeling procedures), separation due to speed of sedimentation e.g. removal of thrombocytes, elutriation, cell adhesion, and the like. Additional processing steps/techniques that can be performed with a sample processing unit of the inventive system include cell culture including expansion, stimulation, differentiation, re-differentiation, antigen loading, transfection, transduction, culture, adherent or in suspension, multi-cell type multilayer or mixed, culture in standstill or with sheer forces or mixing. Input materials include but are not limited to blood, leukopheresis, bone marrow, liposuction, milk, any body fluid, cells from tissue e.g. cells from various organs, tumor cells, single cells, cell clumps, cell aggregates, tissue dissected mechanically or in conjunction with enzymes.

As stated above, a system of the invention will typically include a sample processing unit/system and a sample separation unit/system. Sample separation systems will typically include magnetic based separation systems. One such magnetic based sample separation system that can be included in the system of the present invention includes magnetic separation systems/processes described, for example, on the world wide web at the hyperlink "MiltenyiBiotec.com", and can be used for almost any cell type. Exemplary magnetic separation systems, which is described in part below, are also described for example in the European Patent Specification EP 0 869 838 B1 and in U.S. Pat. No. 5,691,208, which are hereby incorporated by reference.

Improved magnetic separators, devices and methods for magnetic separation procedures are provided and described in EP 0 869 838 B1, which can be included in a system of the present invention. The matrices of the magnetic separators provide uniform pores or channels that reduce the entrapment of air or non-target substances, decrease the loss of target substances due to mechanical disruption.

Biological substances, such as target cells from various systems and organs, are magnetically labeled with a suitable specific binding member, and isolated using the devices and methods of the present invention. The isolation of multipotential cells such as hematopoietic stem or progenitor cells is of particular interest. While hematopoietic cell separation is used herein to provide examples of cell separation procedures, the present invention may be applied to a wide range of cell types or other biological substances.

Cells processed using the present invention can be used for various purposes, e.g. in treatment of diseases, utilizing their potential to proliferate and to differentiate as well as their biological function(s) in living entities, e.g. blood or tissue.

Applications of cells that may be processed using the present invention include, but are not limited to
  graft engineering, e.g. in conjunction with for stem cell transplantation
  organ transplantation
  cancer treatment including but not limited to leukemia including acute myeloid leukemia, chronic myeloid leukemia and solid tumors such as renal cell carcinoma, breast cancer, melanoma, pancreatic cancer
  treatment of refractory autoimmune diseases such as systemic lupus erythematosus or systemic scleroderma, type 1 Diabetes, multiple Sclerosis
  cellular therapy including but not limited to directly utilizing effector cells
  treatment of infectious diseases
  tissue regeneration including, but not limited to myocardial infarction, liver damage or neurodegenerative diseases, and
  tolerance induction including but not limited to transplantation or autoimmune disease.

Processing methods using the present invention can be combined of various basic operations including cell washing, media exchange, cell concentration, incubation of cells with various substances (including antibodies, cytokines, magnetic separation reagents, media), magnetic cell separation, filtration, and cell culture.

Magnetic cell separation methods can comprise both enrichment and depletion procedures (Bosio et al. in "Engineering of Stem Cells", Springer 03/2009). If target cells can be identified based on surface proteins, target cells can be enriched to high purity. In some situations, non-target cells can be identified based on their unwanted functional characteristics within a specific clinical context. These non-target cells can be removed from the cellular product, resulting in a heterogenous mixture of different target cells.

Cell products processed by the present invention for graft engineering approaches can be enriched for CD34, CD133 or depleted for CD3, CD3 and CD19, CD6, CD4 and CD8, T Cell Receptor alpha/beta (TCR alpha/beta) or CD3/CD19/CD16/CD14, resulting either in enriched stein cell preparations or stem cells supplemented with other immune cells such as Natural Killer cells and dendritic cells.

Cell products processed by the present invention for cellular therapy approaches can be enriched e.g. for CD14 (monocytes), CD56 (natural killer cells), CD335 (NKp46, natural killer cells), CD4 (T helper cells), CD8 (cytotoxic T cells), CD1c (BDCA-1, blood dendritic cell subset), CD303 (BDCA-2), CD304 (BDCA-4, blood dendritic cell subset), NKp80 (natural killer cells, gamma/delta T cells, effector/memory T cells), "6B11" (Va24/Vb11; invariant natural killer T cells), CD137 (activated T cells), CD25 (regulatory T cells) or depleted for CD138 (plasma cells), CD4, CD8, CD19, CD25, CD45RA, CD45RO. Natural killer cells, natural killer T cells, T cells and their subsets can be utilized as effector cells in donor lymphocyte infusion approaches to eliminate virus infected cells, tumor cells or bacteria. Dendritic cells, either generated from monocytes in cell culture or directly isolated, can be used to "vaccinate" patients to promote antigen specific and natural immunity against virus infected cells, tumor cells, bacteria, and/or fungi.

Advantageously, the present invention allows for manufacturing of cellular products by sorting for two or more parameters that can be performed in a single tubing set without requirements to transfer the cell suspension from one single use tubing set to another, thus avoiding potential harm to the cell product (infection, contamination, increased temperature). Two parameter sorting applications include generation of highly enriched regulatory T Cells (cell product is first depleted for CD8 and/or CD19 and/or CD49d and subsequently enriched for CD25), of highly enriched natural killer cells (CD3 depleted, CD56 enriched) and of highly enriched blood dendritic cell subsets (CD19 depleted, CD1c enriched).

Tissue regeneration approaches usually utilize progenitor cells from blood, bone marrow or tissue to (re-)vasculize tissue, promote generation of novel tissue or directly provide in vitro generated tissue. Cells utilized can include cell products enriched for CD133, CD34, CD271 (LNGFR; mesenchymal stem cells), anti-MSCA-1 (W8B2; mesenchymal stem cells), CD144 (endothelial cells).

It is a specific and novel characterization of the current invention that manufacturing of cellular products by cell separation and culture can be performed in a single tubing set without requirements to transfer the cell suspension from one single use tubing set to another. In particular, the current invention can be used to obtain Stem cells, T-Cells, dendritic cells, NK-cells, B-cells, monocytes, cells positive for a particular marker, such as CD133, CD34, CD3, CD4, 8, 56, 19, 14, CD141 (BDCA-3), CD303 (BDCA-2), CD304 (BDCA-4), CD144, CD1c (BDCA-1), NKp46, NKp80, CD45RO, CD45RA, CD137, CD25, or CD138.

Composition/Formulation:

It is a specific and novel characterization of the current invention that cell products manufactured by basic operations as described above can be composed for direct clinical use. Methods known in the art require manual post-processing of engineered cell products to adapt it to clinical requirements. With the system of the present invention, the cell product can directly be formulated for immediate use. Formulation steps include: adjustment to a desired volume or cell concentration, exchange of processing liquids by injectable liquids, addition of stabilizers (such as autologous plasma or serum, serum albumins, other proteins or synthetic polymers) or adjuvants, supplementation with cryoprotective agents such as DMSO for subsequent storage, drawing of retain samples for quality control, delivery to combinations of bags or syringes for infusion. Some components of the final formulation e.g. plasma, platelets, or platelet components may be derived from the originating sample.

The magnetic separation system of the present invention can be used to magnetically label and isolate any desired target substance. Of particular interest is the separation of a specific component from a complex mixture. The separation system of the present invention has great versatility, in that almost any target substance may be separated once a specific binding member is available. The target substance or analyte may be any member of a specific binding pair, or a substance associated with a member of a specific binding pair. As an example, a cell surface antigen-antibody binding pair may be used to isolate the antigen itself, cells that express the antigen, a particular organelle involved in processing of the antigen, etc. The devices and methods of the present invention are also advantageously applied to diagnostic techniques involving the binding of a receptor and ligand, such as immunoassays, and the like.

In its simplest form, a cell separation system of the present invention has two main components: a magnetic separator and a cell separation reagent. A schematic diagram of a magnetic separator device is given in FIG. 1. The diagram shows the general construction of the separator and the uniform fluid passage that results from the use of a matrix of metallic spheres. FIG. 2 depicts a more complex separation device, including the general positions of fluid passages, collection and storage containers and the separation column. The fluid circuitry can be constructed with integrated valves, or the valves may be applied externally to the fluid pathways.

Figure 2:
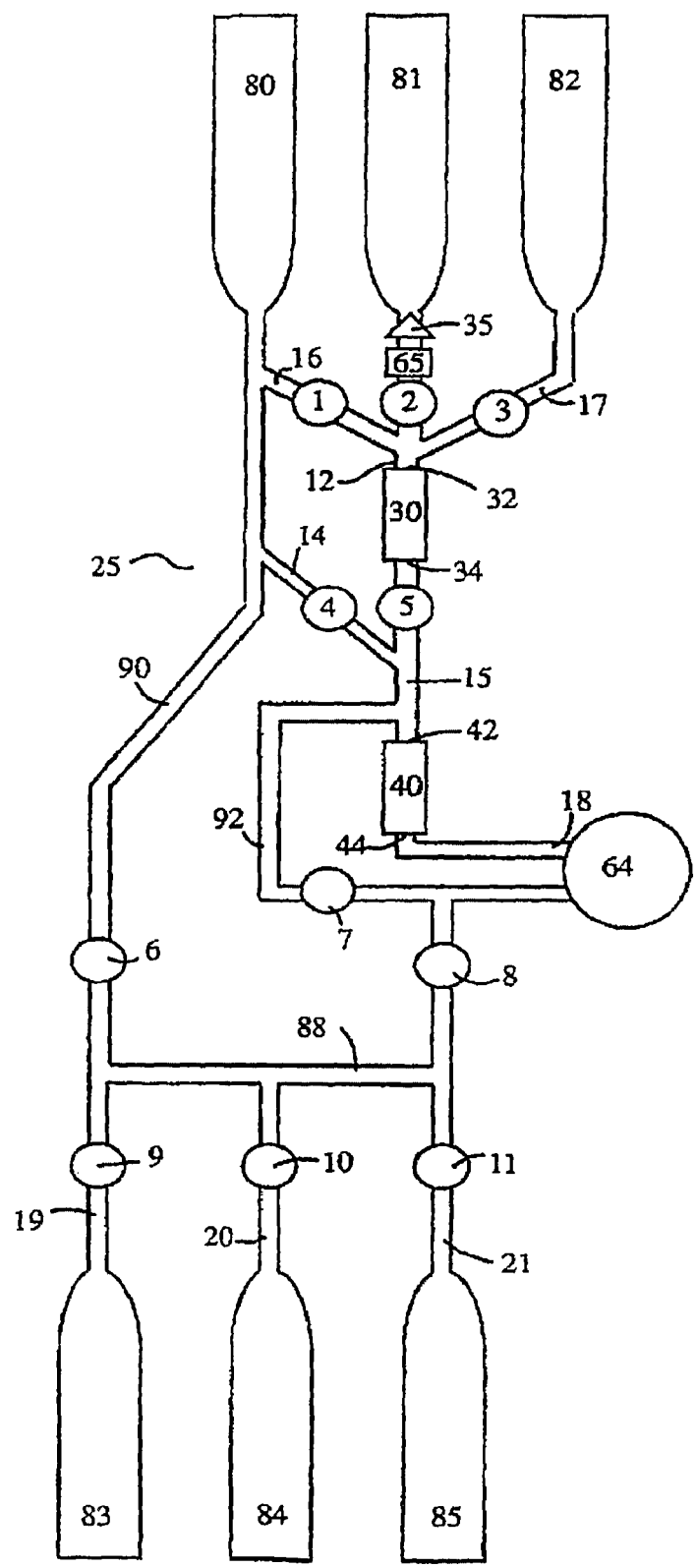
FIG. 2 depicts separation and prefiltration columns, together with the sample and collection containers, interconnected by a series of fluid pathways or fluid circuits. The figure also shows the positioning of valves and a peristaltic pump that is used in the preferred embodiment of the separation system.
Figure 3:
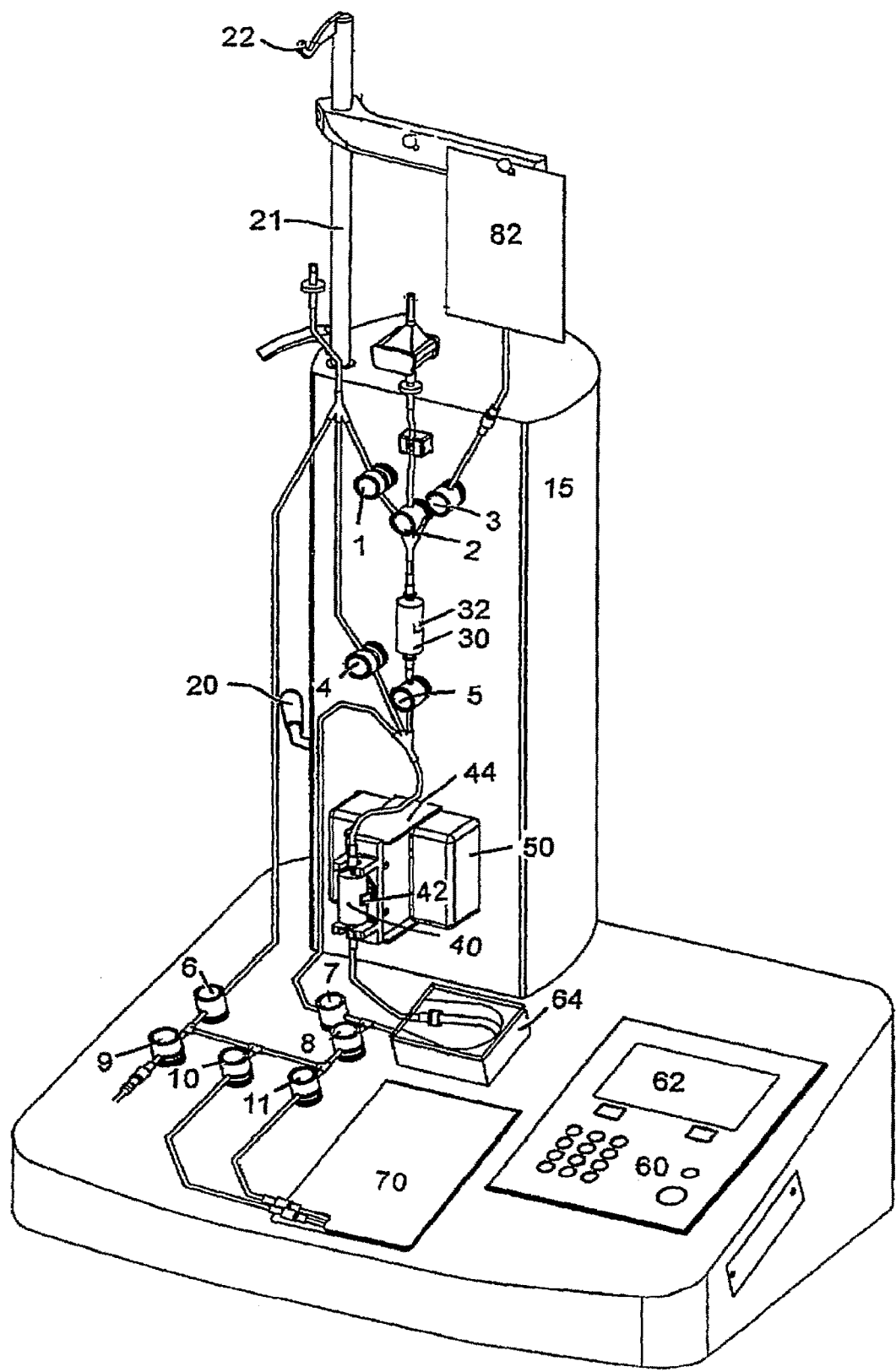
FIG. 3 depicts a computer-controlled unit on which sterile columns, disposable tubing and storage and collection containers, as illustrated in FIG. 2, are appended. In a preferred embodiment, the computer-controlled unit contains a magnet, valves and peristaltic pump.

An optional third component to the preferred cell separation system is a cell separation instrument. FIG. 3 depicts a cell separation instrument, preferably computer-controlled, which may incorporate the valves together with a magnet, pump and keyboard control. A device similar to that of FIG. 2, constructed without valves, may be mounted directly onto the instrument of FIG. 3 for use in the automated separation of target cells.

The cell separation reagent, which may also be referred to as a conjugate, antibody/magnetic particle reagent or magnetic label, includes a magnetically responsive material bound to a specific binding member. There are many well-known magnetically responsive materials used in magnetic separation methods. The present invention involves the use of magnetically responsive particles or microparticles. Suitable magnetic particles are described in Molday U.S. Pat. No. 4,452,773, and in the European Patent Specification EP 452342 B, which are hereby incorporated by reference. Colloidal sized particles, such as those described in Owen U.S. Pat. No. 4,795,698, and Liberti et al. U.S. Pat. No. 5,200,084, are also suitable.

The term "specific binding member" as used herein refers to a member of a specific binding pair, i.e. two molecules, usually two different molecules, where one of the molecules through chemical or physical means specifically binds to the other molecule. The complementary members of a specific binding pair are sometimes referred to as a ligand and receptor. In addition to antigen and antibody specific binding pairs, peptide-MHC antigen and T cell receptor pairs; alternative specific binding pairs of interest include biotin and avidin or streptavidin; carbohydrates and lectins; complementary nucleotide sequences (including nucleic acid sequences used as probes and capture agents in DNA hybridization assays); peptide ligands and receptor; effector and receptor molecules; hormones and hormone binding protein; enzyme cofactors and enzymes; enzyme inhibitors and enzymes; secretion markers, as described in International application PCT/US93/10126 (hereby incorporated by reference); autologous monoclonal antibodies, and the like. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc. so long as an epitope is present.

Immunological specific binding pairs include antigens and antigen specific antibodies or T cell antigen receptors. Suitable antigens may be haptens, proteins, peptides, carbohydrates, etc. Recombinant DNA methods or peptide synthesis may be used to produce chimeric, truncated, or single chain analogs of either member of the binding pair, where chimeric proteins may provide mixture(s) or fragment(s) thereof, or a mixture of an antibody and other specific binding members. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well known to those skilled in the art.

For brevity, the separation system will mainly be described in terms of its ability to specifically select and separate a defined population of cells (target cells) from a mixed cell population, such as peripheral blood, bone marrow, blood from the umbilical cord or placenta, fetal blood or a leukapheresis product. It will also be appreciated that some tissues may be disrupted into a single cell or monodisperse suspension to allow isolation of a particular cell subset, such as the separation of tumor infiltrating lymphocytes from a tumor mass, the separation of islet cells from kidney tissue, etc. For example, different cell types may be labeled with a specific antibody to allow cell purging and/or cell enrichment. The target cell population is generally identified by a specific binding member, as described above, which selectively binds to a cell surface antigen present on the target cells. It should be understood, however, that the subject apparatus and method is not limited to such uses.

For simplicity, the specific binding member will be exemplified herein by an antibody. The antibody may be directly or indirectly bound to a magnetic particle. If the antibody is directly bound to the magnetic particle, then the target cell population is magnetically labeled when the antibody binds to the cell surface antigen. If the antibody is indirectly bound to the magnetic particle, then the target cell population is susceptible to magnetic labeling when the antibody is bound to the target cells. The antibody-bound cell population is actually labeled by further contacting the cells with a specific binding member for the antibody, where that specific binding member is itself bound to a magnetic particle. The target cells, identified by such magnetic labeling, are then separated from other cells by means of a magnetic field. For example, a specific binding member such as avidin can be conjugated to a magnetic particle where the avidin binds to a biotinylated antibody that in turn specifically binds to the target cells.

The specific binding member may be directly attached to the magnetic particle. This may be accomplished by means of reactive groups on the specific binding member and magnetic particle themselves. Alternatively, the specific binding member and magnetic particle may be joined by means of a coupling agent or linker. The terms "coupling agent" or "linker", as used herein, include various bifunctional crosslinking or coupling agents, i.e. molecules containing two reactive groups or "ends", which may be separated by a spacer.

Conventional high gradient magnetic separation matrices are typically prepared from materials such as wires, metal-coated fiber or steel wool. In the improved magnetic separation device of the present invention, the gradient-intensifying matrix of the high gradient magnetic separator is formed from small spheres of magnetically susceptible or ferromagnetic material. Such materials include, but are not limited to iron, steel, cobalt nickel, and other ferromagnetic rare earth metals or alloys thereof. For example, the matrix material may include ferromagnetic metal spheres such as iron spheres (e.g. MARABU Balls, Kugelfabrik Schulte & Co., Wermelskirchen, Germany). Many different methods of manufacturing spheres are known. Usually the spheres have an average diameter ranging from about 0.2 to 1.5 mm for the separation of large cells or cell complexes, and about 0.05 to 0.2 mm diameter for subcellular material. Preferably, the spheres have an average diameter ranging from about 0.2 to 0.5 mm, and most preferably, the spheres are selected to have an average diameter ranging from about 0.2 to 0.3 mm. It is desirable that the size of spheres be relatively homogeneous, usually varying not more than about 15% from the average size, more usually by not more than about 10%, and preferably by not more than about 5%.

Figure 4:
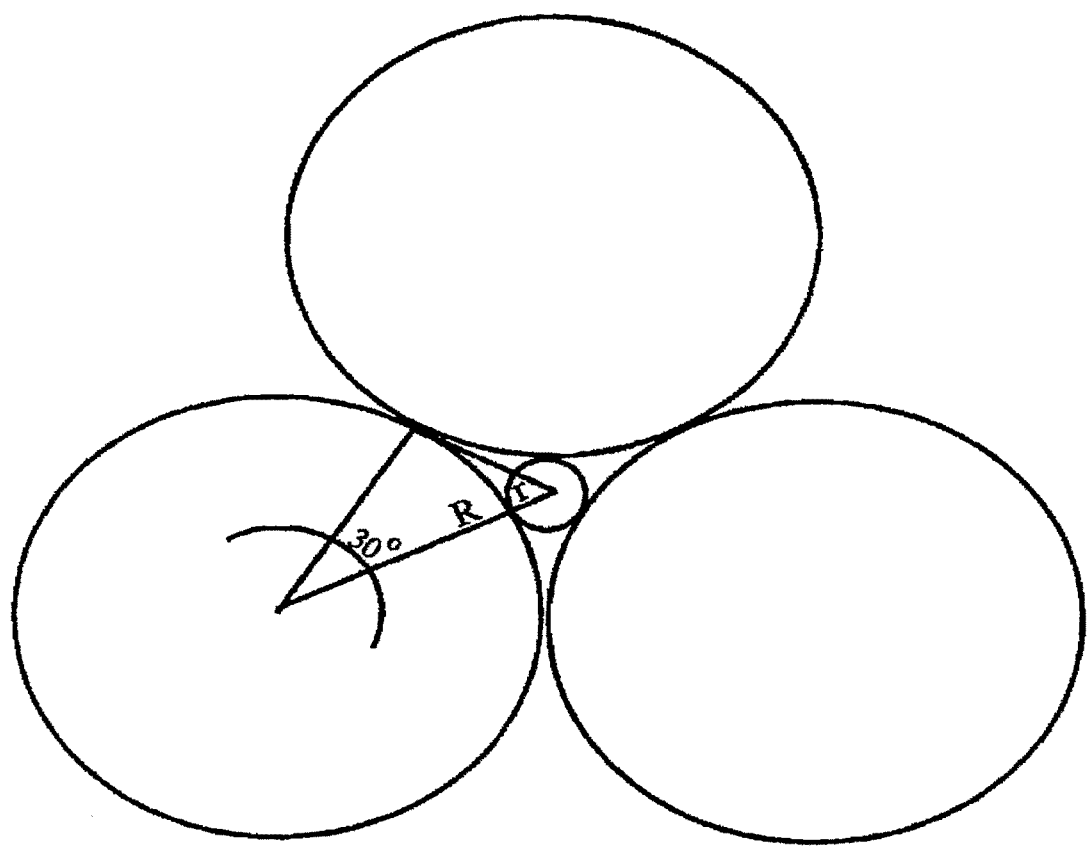
FIG. 4 depicts the flow channel formed between three connecting spheres.

The substantially symmetrical spherical shape and substantially uniform size of the spheres are desirable for the construction of a magnetic separator matrix, as the spheres can assume a lattice configuration wherein the gaps between the spheres form regular channels or pores in the matrix. The lattice configuration is a patterned framework of spheres that forms channels of regular size between adjacent spheres and throughout the matrix. Upon the application of a magnetic field to the separator, magnetic field gradients are created in the gaps between the spheres. The uniform size, and therefore spacing, of the spheres provides for a substantially uniform magnetic gradient throughout the matrix, and substantially uniform fluid flow characteristics. A flow channel is depicted in FIG. 4. The dimensions of the channel can be described by the maximum size ball or particle that would fit between the matrix spheres. With reference to FIG. 4, the geometrical relationship is r=about 0.155 R. It will be appreciated from the teachings of the present invention that the channel size may be adjusted to an average diameter optimal for the desired separation process by varying the size of the spheres that are used to form the matrix.

The spherical shape provides for the formation of a substantially stable matrix structure when the spheres are packed within a housing that defines a separation chamber. As described in detail below, the matrix is also coated with a substantially fluid impermeable material such as a plastic polymer. On application of a plastic polymer coating, the tight gaps between the spheres are closed, resulting in a hydrodynamically optimized matrix. The resulting ferromagnetic matrix will usually occupy about 60% to 75% of the total volume of the separation chamber, and will be permeable to fluids. The impermeable coating will occupy about 1 to 5% of the total volume. The free volume will range from about 20% to 40% of the total separation chamber volume. In a preferred embodiment, the total matrix will occupy about 75% to 80% of the total volume of the separation chamber.

FIG. 1 presents a schematic of an exemplary separation column. The spheres are not depicted at scale, but so as to better depict the formation of a three dimensional fluid permeable matrix 6. The spheres are packed in a housing 4 which is made of a non-magnetic material. The magnetic separator housing serves as the body of the separation column, and the interior of the housing defines a separation chamber. Housings of various lengths, shapes and diameters are advantageously made of plastic. Suitable nonmagnetic materials for the construction of a magnetic separator housing include stainless steel, glass, plastic, etc.

In one preferred embodiment, the magnetic separator housing is a plastic that the matrix coating will adhere to, allowing improved hydrodynamic properties at the boundary of the matrix and housing. It will be appreciated that the coating material and housing material will be selected for compatibility with one another, e.g. a lacquer coating must be selected that will not result in non-adherent plastic debris accumulating in the column. Various mechanisms are known by which materials adhere to each other, and may be exploited for this purpose. Conveniently, the selection for compatibility may be made based on the solvent used in conjunction with the lacquer. The solvent will be slightly reactive with the plastic housing, such that the lacquer in the solvent will adhere, but not so reactive that the structural integrity of the column is compromised during the lacquer curing process. For example, the coating material may be selected to include a solvent that causes a slight dissolution of the interior of the plastic housing. Upon curing, the plastic rehardens thereby bonding or sealing the coating material and housing material to each other. One of skill in the art will appreciate that information regarding such reactivity is generally available. Exemplary of a suitable solvent and housing combination is methylethylketone and the plastic ULTEM® (General Electric).

Preferably, each of the materials selected for the construction of separation column 2 will also be compatible with sterilization procedures. Preferably, the housing is cylindrical in shape to facilitate the flow of sample through the separation chamber as well as the formation of three-dimensional matrix 6 within the housing. The walls of the housing preferably have a thickness of about 1 to 3 mm. The separation column has inlet 12 and outlet 14 ports for the introduction and discharge of fluids. Generally, the inlet and outlet ports are narrow structures relative to the main body of the housing. This facilitates the attachment of the separator to further fluid circuitry in a separation system and advantageously maintains the device as a closed system. The inlet and outlet ports may be positioned at different sites than as depicted in FIG. 1, but it will be appreciated that the overall structure of the separator will preferably provide a separation chamber having the fewest bends or corners which might otherwise slow fluid flow or create spaces where sample might accumulate.

At the inlet and outlet of the column, the column is constructed to have a feeding mechanism ensuring optimal homogeneous distribution and flow through the matrix. The distribution mechanism is comprised of the volume in front of cap layer 8 and the cap layer itself, which serves as a flow resistor. The distribution volume (in milliliters) may be defined relative to the width of the column (in millimeters), usually having a ratio of about 0.1 to 10. The chamber volume in front of base layer 10, as well as the base layer itself, also serves as feeding mechanism for fluids passing into the chamber via the outlet port.

It is preferable to have column dimensions where the diameter to length ratio is at least 0.2 to 1. The actual dimensions of the column will depend on the material being separated, and the desired flow rate for separation. The column dimensions will provide a chamber that will accept a matrix having an adequate surface area to create sufficient magnetic field gradients in the separation chamber and permitting efficient retention of magnetically labeled material. The volume necessary for a given separation may be empirically determined, and will vary with the size, antigen density on the cell surface, antibody affinity, etc. As an example, a sectional area of 3 cm$^2$ allows a flow rate of 5 to 40 ml/minute. The binding capacity of a 2×4 cm matrix is approximately 10$^9$ labeled cells.

To facilitate the manufacture of the separation column, base layer 10 of nonmagnetic porous material is positioned in the housing such that when the ferromagnetic spheres are placed in the chamber they do not pass through outlet port 14. Suitable porous materials for the formation of the base layer include, but are not limited to, porous plastic, sintered metals or glass, grids, etc. For example, various porous frits available from Porex Singwitz, Germany may be used. Usually, the porous material will have a pore size of about 20 to 200 μm, preferably of 50 to 150 μm. A suitable pore size will be selected according to the dimensions of the target substance and the make up of the sample material. In addition, the pore size will not be so large as to allow the spheres to fill the porous openings of the layer material. Following the insertion of the spheres into the chamber, the housing may be shaken or vibrated to facilitate the settling of the spheres into a more uniform configuration. Optionally, cap layer 8 of non-magnetic porous material is positioned in the housing over the matrix to maintain the uniform configuration of the matrix during storage, handling and use. Pressure may also be applied to cap layer 8 to more firmly pack the spheres within the chamber. Upper portion 16 of the separation column, which includes inlet port 12 in this embodiment, is then positioned on the top of housing 4 and is attached to the housing. For example, when using plastic materials, upper portion 16 might be glued or ultrasonically welded to housing 4 to complete the formation of the separation column. Following the completion of the housing, the matrix is coated.

With reference to FIG. 1, a coating is applied to the fluid permeable matrix described above. The coating is selected to be substantially impermeable to ions, and therefore protects the metallic matrix material from corrosion as well as inhibiting the escape of cations from the matrix, which might damage the cells. In addition to the formation of an impermeable protective layer over the matrix material, a complete coating of the matrix closes the gaps between spheres, providing both mechanical stability to the matrix, and a hydrodynamically optimized matrix. Such mechanical stability is particularly advantageous when the matrix is formed from small spheres of magnetically susceptible or responsive metal, as described above. A coating material such as a lacquer coating may be flowed into inlet port 12 of the separation column. The lacquer flows through cap layer 8, matrix 6 and base layer 10, thereby coating the porous surface of each component. Excess lacquer is allowed to pass from the chamber outlet port 14. The coated separation column may be centrifuged to further expel excess coating material from the chamber. The coating is then allowed to dry. The separation column may be heated to further promote the drying of the coating. For example, the coated separation column may be placed in an oven at 110° C. for four to five hours followed by continued drying at room temperature for three to seven days.

Upon drying, the coating hardens, thereby providing mechanical support to the matrix. Not only does this mechanical support aid in maintaining integrity of the matrix during the storage and handling of the separation column, it also provides the matrix with a rigid structure which does not exhibit significant elasticity. This rigidity is advantageous because the matrix might otherwise be deformed upon the application of an external magnetic field to the separation column. The applied magnetic field strength of the external magnetic means is typically within a range of about 0.1 about 1.5 Tesla, and more preferably between about 0.2 to about 0.8 Tesla. The field should be great enough and the distance between the magnet and the separation column should be small enough to induce intensified magnetic field gradients within the matrix. To maintain uniform magnetic gradients in the separator, the matrix material should move or shift in the chamber upon the application of the magnetic field. The spherical metallic components, the housing and the coating are advantageously combined in the present invention to provide an improved matrix with sufficient rigidity to resist substantial deformation when the separation column is placed within a magnetic field.

It is preferable to coat the matrix while the spherical metallic components are within the separation column housing. Coating the matrix within the housing avoids disrupting the matrix after the coating has been applied. Moreover, the matrix within the housing serves to fill or seal small void spaces, interstices crevices formed near the contact points between the spheres, as well as between the spheres and housing, while simultaneously providing a uniform surface to the channels or formed by the separated points of the spheres. These channels or pores result in the permeability of the matrix. By sealing the void spaces, there is a decrease in the areas where cells or other solid components of the sample might wedge or become physically en-trapped, even in the absence of a magnetic field.

In the completed separation column, the selection of matrix coating materials will preferably result in channels or pathways through the permeable matrix having an average diameter ranging from 20 to 60 μm and an occupying of about 60% to 80% of the total volume of the separation chamber. For example, a separation column for the separation of blood cells may have a final coated-channel size averaging 20 μm, with the matrix occupying approximately 80% of the total volume of the chamber.

Following the preparation of the substantially impermeable coating, the matrix and other interior surfaces of the separation chamber are preferably further treated by the addition of a hydrophilic material such as polyvidone (BASF, Ludwigshafen, Germany). Other suitable hydrophilic coating materials include, but are not limited to, polyvinylpyrrolidine, polyethylene glycol, hydroxyethyl starch, and hydrophilic coatings, such as acrylamides, surfactants or detergent-type wetting agents, and biological material including, but not limited to, heparin and human serum albumin. The interior surface of the separation chamber may also be made hydrophilic by plasma or corona etching of the surface. The hydrophilic coating provides the interior the separation column and the fluid permeable matrix with a readily wettable surface. By enhancing the wettability of these surfaces, the introduction of fluid into the separation column will produce a uniform fluid front as it passes through the chamber. This in facilitates the removal of air bubbles from the permeable matrix and other void space in the separation chamber. It is desirable to maintain the separation column and other device components as a closed system substantially free of air during the separation process. The presence of air in the system during the separation of target cells affects the interior surface tensions and unventilated areas, which can lead to cell destruction.

Referring to FIG. 2, which depicts a separation device, separation column 40 may be preceded by a prefiltration device. The figure depicts the prefiltration device as a column 30, however it will be understood that other configurations, such as prefilter, may find use. The prefiltration column is generally a three dimensional structure that may be substantially identical to the separation column in terms of its structural composition. The prefiltration column, however, may have different dimensions, the matrix may be made of spheres having a different composition, e.g. a non-ferromagnetic material, or the matrix may be made of spheres having a different diameter from those used in the separation column, thereby providing a pore or channel size different from that found in the separation column. In one embodiment, the prefiltration column is identical to the separation column. Passage of the sample through the prefiltration column serves to trap and remove fluid components that are not desired in the final separation product. For example, in blood cell separations, "sticky" cells such as monocytes, granulocytes and platelets may be removed from the cell suspension by the prefiltration column. Alternatively, the prefiltration column may be constructed to have an average pore size that is smaller than that found in the separation column. For example, the pore size of the permeable matrix may be selected to remove large tumor cells from the sample prior to the fluid's passage through the separation column. The passage of the fluid sample through the prefiltration column may also serve to break apart aggregates, such as cell aggregates, that may exist in the fluid. Moreover, because the prefiltration column contains materials substantially identical to those of the separation column, those sample components that might non-specifically bind to the separation column are advantageously caught by the prefiltration column. Thus, the prefiltration column reduces the possibility of fouling the separation column during the separation process, and it reduces the collection of unwanted cells or fluid components in the final separation product.

Referring to FIG. 2, a preferred embodiment of separation device 25 is depicted. Sample container 81 is connected to an optional suspension filter 35. The suspension filter may be used to remove unwanted particulate components from the fluid sample and is selected to have a pore size sufficient to remove particulates above a certain size. For example, the suspension filter may be a Pall Filter (Pall SQ40S; Pall Biomedical, Inc., Puerto Rico) having a pore size selected to remove particulates larger than 40 μm, such as cell clots and clumps in hematopoietic cell samples. The suspension filter is connected by fluid pathway two 12 to inlet port 32 of prefiltration column 30.

Outlet port 34 of the prefiltration column 30 is connected by fluid pathway five 15 to inlet port 42 of separation column 40 to which the magnetic field will be applied in the course of the separation process. Outlet port 44 of the separation column is connected by fluid pathway eight 18 to distribution channel 88 which leads to product collection container 83, final wash waste container 84 and unlabeled sample container 85. Separate fluid pathways nine 19, ten 20, and eleven 21 lead to these containers, respectively.

This separation device further includes a wash or buffer container 80 and an initial wash waste container 82, which are connected by fluid pathways one 16 and three 17, respectively, to fluid pathway two 12. Buffer container 80 is also connected via wash or buffer line 90 (fluid pathway six) to distribution channel 88. The buffer line is further connected to fluid pathway five 15 by means of fluid pathway four 14. The fluid pathways, containers, filters and columns may be coupled to one another by means of any suitable means such as standard spikes, Luer locks, male-female connectors, T-connectors, Y-connectors and 4-way connectors or other fittings as are commonly used in intravenous solution delivery sets.

Fluid flow through the fluid circuitry of the separation device can be controlled by means of valves placed within the fluid pathway(s). Fluid pathways one through eleven are associated with corresponding valves one through eleven (1-11). The valves may be inside the pathways themselves or may be external to the pathways. The fluid flow may also be controlled by a pump. For example, when the fluid pathways are made of a flexible material, such as flexible tubing, suitable valves for the control of fluid transport include pinch valves. The pinch valves close the fluid pathway by depressing the walls of the tubing against one another. It will be appreciated by those skilled in the art that such pinch valves will be selected to accommodate the size of the tubing chosen for use as a fluid pathway. In addition, the compression force of the pinch valve will be selected to achieve the compression of the chosen tubing and thereby affect the closure of the fluid pathway. The valve specifications, therefore, will be matched to the softness or hardness (durometer) specifications of the selected tubing.

An embodiment of the separation device further includes recirculation loop 92 (fluid pathway seven) such that fluid that has already passed through separation column 40 may be recirculated through the separation column. Typically, a pump 64 will be connected to the recirculation loop to facilitate the recycling of fluid through the separation column as well as control the flow through the column. It will be appreciated by those skilled in the art that a variety of pumps may be used. An exemplary pump is a peristaltic pump that can control the passage of fluid through the recirculation loop in either direction and at variable speeds.

The separation device having a recirculation loop allows sequential separations on one column, by a process of binding and elution, followed by a second binding and elution. Sequential separations provide improved purity in the final target population.

FIG. 2 schematically depicts a preferred embodiment of a separation device. It will be appreciated, however, that a separation process may be accomplished using the basic system components, i.e. the improved magnetic separator and collection containers.

It will be appreciated by those skilled in the art that the recirculation means and fluid flow pathways of the present invention are also suitable for use in alternate separation systems. For example, the recirculation means may be advantageously used in a system wherein the separation means involves centrifugal techniques, absorption columns or chemical means as alternatives to the magnetic or electromagnetic separation means.

In an exemplary cell separation process, the fluid pathways and columns are primed by allowing a wash liquid to flow through all of the fluid pathways and columns, preferably at varying flow speeds and pressures. The wash liquid may contain materials such as a physiologically acceptable protein, such as human serum albumin (HSA), which inhibits cells from adhering to the interior surfaces of plastic device components. The wash liquid may also contain small quantities of physiologically acceptable surfactants or detergents, to improve the wetting of the interior surfaces.

It is found that large air bubbles in the fluid pathways are detrimental to the recovery of viable cells. Methods of removing air bubbles from fluid pathways are known in the art, and may be employed for this purpose. A method of particular interest exploits the observation that a permeable frit such as those used in the cap layer and/or base layer will not allow passage of air bubbles at fluid flow rates of less than about 400 ml/minute. A column may be cleared of air bubbles by circulating wash liquid through a recirculation loop at flow speeds of less than about 400 ml/minute. The air bubbles then accumulate outside of the column at the base and/or cap layers. The direction of flow is then reversed, and the bubbles are washed out of the system into a suitable waste bag. Preferably, the sequence is repeated to ensure the removal of all bubbles. The existing bubbles may be intentionally enlarged by the generation of negative pressure.

In such an exemplary process, magnetically-conjugated antibodies may be used to specifically target the desired cells in a mixed cell population. The magnetic reagent is incubated with the mixed cell population, then unbound particles are washed away by any convenient means, e.g. centrifugation, etc. When cell sterility is desired, the antibody incubations and washes may be performed in a closed container process, where the antibodies and wash liquids are added to a sterile container by means of a sterile syringe or similar device. In this way, contamination of the desired cells by air-borne microorganisms is minimized. In such a closed system, particularly where the container is a flexible bag, the mixing of cells and antibody may be improved by injecting a small amount of sterile air, at a ratio of from about 0.5 to 2 of air to liquid, into the container.

The incubated cell suspension, now containing magnetically labeled target cells, is passed through the separation device. The system transports the cells through a magnetic separator which is positioned within or is adjacent to a magnetic field. The source of the magnetic field may be a permanent magnet or an electromagnet. The separation column is preferably constructed to include a ferromagnetic matrix of stacked ferromagnetic spheres, as described above.

Optionally, the sample is passed through a prefiltration column, also constructed as described above, prior to passage through the separation column. If the separation column contains a matrix comprised of other than ferromagnetic spheres, then the sample may be first passed through a prefiltration column that is substantially identical to that separation column.

The magnetically labeled cells accumulate in the separation column in response to the magnetic field. The non-labeled cells and other suspension components pass through the separation column and into an unlabeled sample container and/or waste container. The labeled or purified cells may then be eluted from the separation column by either removing the separation column from the magnetic field or removing the magnetic field from the separation column. A wash solution, such as a buffered liquid, is passed through the separation column to wash the labeled cells from the separation column and into a product collection container. The collection container may be used for further processing of the target cells or cryopreservation of the target cells.

In preferred embodiments, the separation column is a high gradient magnetic separation column constructed from ferromagnetic spheres, as described above. The containers referred to herein are typically plastic bags, such as those used for the storage and delivery of intravenous fluids, but any suitable containers can be used. The containers will be selected for their necessary storage or collection volume, their capacity for sterilization and their ability to be used in a closed system, i.e. a separation system from which substantially all of the air can be removed prior to use.

In another embodiment, the magnetically labeled cells are recirculated through the separation column to enhance the selection of the target cells and the removal of unwanted cells or other suspension components. Some preferred embodiments also include the use of a prefiltration column. The prefiltration column, however, is not, subjected to a magnetic field. Instead, the preliminary passage of the cell suspension through the prefiltration column results in the capture of suspension components or materials that otherwise might non-specifically bind to the separation column. Such non-specific binding may cause the blockage or fouling of the separation column, which could in turn inhibit or reduce the separation and collection of the labeled cell population.

The fluid pathways, collection containers, suspension filter, prefiltration column and separation column, may be constructed, interconnected and supplied as a disposable separation device. The target cells are preferably collected in a sterile blood transfer container from which the cells can be transplanted to the patient or in which the cells can be stored or subjected to further processing. The complete cell separation device may be pre-packaged in suitable containers. The pre-packaged device can be sterilized and provided ready for use in the improved magnetic separation process of the present invention. The reagents necessary for the desired separation process may also be provided in kit form. For example, a conjugate specific for the target cell population or other analyte may be provided separately from, or with the device. The kit may also include wash solutions, for example standard sterile saline solution, and/or other buffered liquids, such as phosphate buffered saline, 1 mmol/l EDTA and 0.5% human serum albumin. These reagents or other solutions can be provided in containers such as plastic bags that can be connected to the appropriate fluid passages of the cell separation device.

The improved separation system of the present invention may be totally automated. In the automated system, a computer controls the flow of fluids through the fluid circuitry and separation column, controls the magnetic field strength or placement of the magnet and/or separation column to provide for the retention and release of the magnetically labeled target cells or analyte, and directs the final collection products into appropriate containers.

One embodiment of an automated cell separation instrument, as depicted in FIG. 3, includes mechanical, electromechanical and magnetic components. The mechanical components may include: an instrument outer shell or housing 15; adjustable container holder 21; peristaltic pump 64; prefiltration column holder 32, and separation column holder 42. The electromechanical components may include: solenoid pinch valves 1-11; an internal motor (not shown) to drive peristaltic pump 64; an internal motor (not shown) to move separation column holder 42 (and thereby move the separation column 40) into or out of the magnetic field, or to move the magnet 50; and a bubble detector (ultrasonic sensor) 65, which is used to detect the presence of fluid in the fluid circuitry. The magnetic means may include permanent and electromagnets. It will be appreciated that these individual components may be selected from a number of readily available alternates and may be combined in a variety of configurations without departing from the general description of the improved magnetic separation system of the present invention.

In a preferred embodiment of the separation device, the fluid pathways, solution and collection containers, suspension filter, prefiltration column, separation column and connectors are provided as a preassembled disposable component to the separation system. The separation device is mounted on the separation instrument for the performance of the separation process. Upon completion of the separation process the product collection container may be removed, and the remaining separation device components are disposed.

Preferably, an onboard microprocessor (not shown) controls all of the electromechanical components of the instrument, and software directs the system to perform the appropriate operations in a standard sequence. A display 62 and operator keypad 60 allow the operator to monitor automatic system operation and to control instrument operation in a manual mode. A printer (not shown) may be connected to the microprocessor for printing process information, labels, etc.

FIG. 3 depicts a separation instrument and mounted separation device. In this embodiment, the separation device is mounted or installed upon the instrument by positioning the tubing of the fluid pathways in their respective external pinch valves 1-11, as described above. Prefiltration column 30 is placed within prefiltration column holder 32. Separation column 40 is placed within separation column holder 42 which is moved relative to magnet 50 by means of retractable arm 44. Adjustable clamp 20 is used to secure hanger arm 21 in a raised position. There are mounts or pegs 22 on the hanger arm on which to place initial wash waste container 82 and buffer and sample containers (not shown) as appropriate. The apparatus may further include storage compartment 70 to separate the final waste container and unlabeled sample container from the product collection container (not shown).

Figure 5:
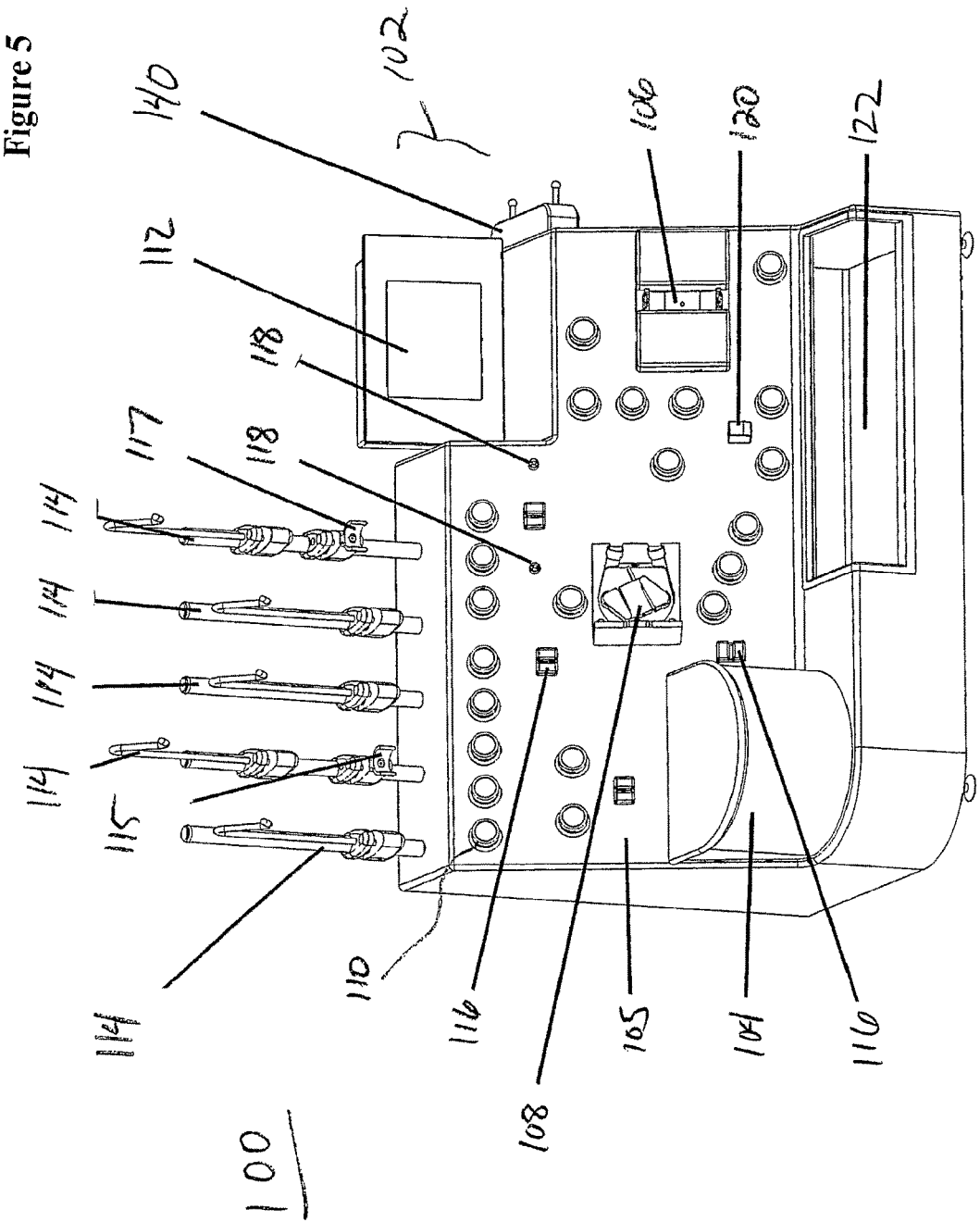
FIGS. 5 through 7 illustrate a system according to an embodiment of the present invention.

As previously mentioned, separation systems as described above can further be integrated with various sample/cell processing systems for accomplishing sample preparation steps prior to sample component separation by the described magnetic based separation techniques. FIG. 5 illustrates a system according to an embodiment of the present invention. As described above, a system of the present invention can include various mechanical, electromechanical, and magnetic components. The system 100 includes a separation unit 106 and processing unit 104 integrated into a single system containing an outer shell or housing 105. The system 100 can include a magnetic separation system or unit similar to those described above. The system 100 includes a magnetic separation unit 106 including a housing for positioning a separation column (e.g., magnetic separation column as described above, FIG. 1) in the magnetic separation unit 106. The system 100 further includes a pump 108 and a plurality of fluid flow control means or valves, as illustrated by valve 110. It is noted that, while only valve 110 is specifically identified by number, the system 100 as shown in FIG. 5 illustrates a number of valves that are identifiable as having an illustrated structure identical to that of valve 110. It will be further recognized that while each of the plurality of flow control means/valves are identical in FIG. 5 for illustrative purposes, flow control means according to the present invention can take a variety of embodiments and can include one or more different types of means/valves in a single system. Components of the system 100 (e.g., valves, pump, separation unit, etc.) can be coupled or connected by one or more flow paths so as to form a series of fluid pathways or fluid circuits similar to as discussed above. The system further includes a computer control system or unit 112 providing monitoring and/or control of one or more aspects of the system 100.

The computer system 112, as described above, can include one or more input and/or output devices, graphical displays, user interfaces and may allow for manual and/or automated control of system 100 operation and functions. The computer control system 112 can include a module or system to process information (e.g., flow information, etc.) within the system 100 and can include a wide variety of proprietary and/or commercially available computers, components or electronics having one or more processing structures and the like, with such systems often comprising data processing hardware and/or software configured to implement any one or a combination of method steps as described herein. Software will typically comprise machine readable code of programming instructions embodied in a tangible media such as a memory, digital or optical recording media, optical, electrical, or wireless telemetry signals, or the like, and one or more of these structures may also be used to output or transmit data, signals, or information between components of the system in any of a wide variety of signal processing architectures.

The system can further include various supports, sensors, housings, etc. for various components that can be coupled with the present system to perform methods as described herein. The system 100 further include one or more support structures 114 configured to hold and/or support various fluids, reagents, samples fluid reservoirs, filters, and the like that can be utilized with the system 100 according to the present invention. Support structures can include various hook or hanger, or holder (e.g., filter holder or housing) configurations and are not limited to any particular design. Fluids, buffers, reagents, etc. positioned on a support 114 can be coupled to a fluid path or tubing, that can in turn be connected to more or more components of the system 100. The system 100 can include sensors for monitoring and/or further controlling fluid flow through the system. Sensors can include, for example, liquid sensors, which can include bubble detectors (ultrasonic detector), pressure sensors, and the like. Bubble detector 116 and pressure sensors 118 are shown. A support 120 is show, which can be configured to hold a filter or volume reduction unit. Collection area 122 can support collection containers, reagents, etc.

Figure 6:
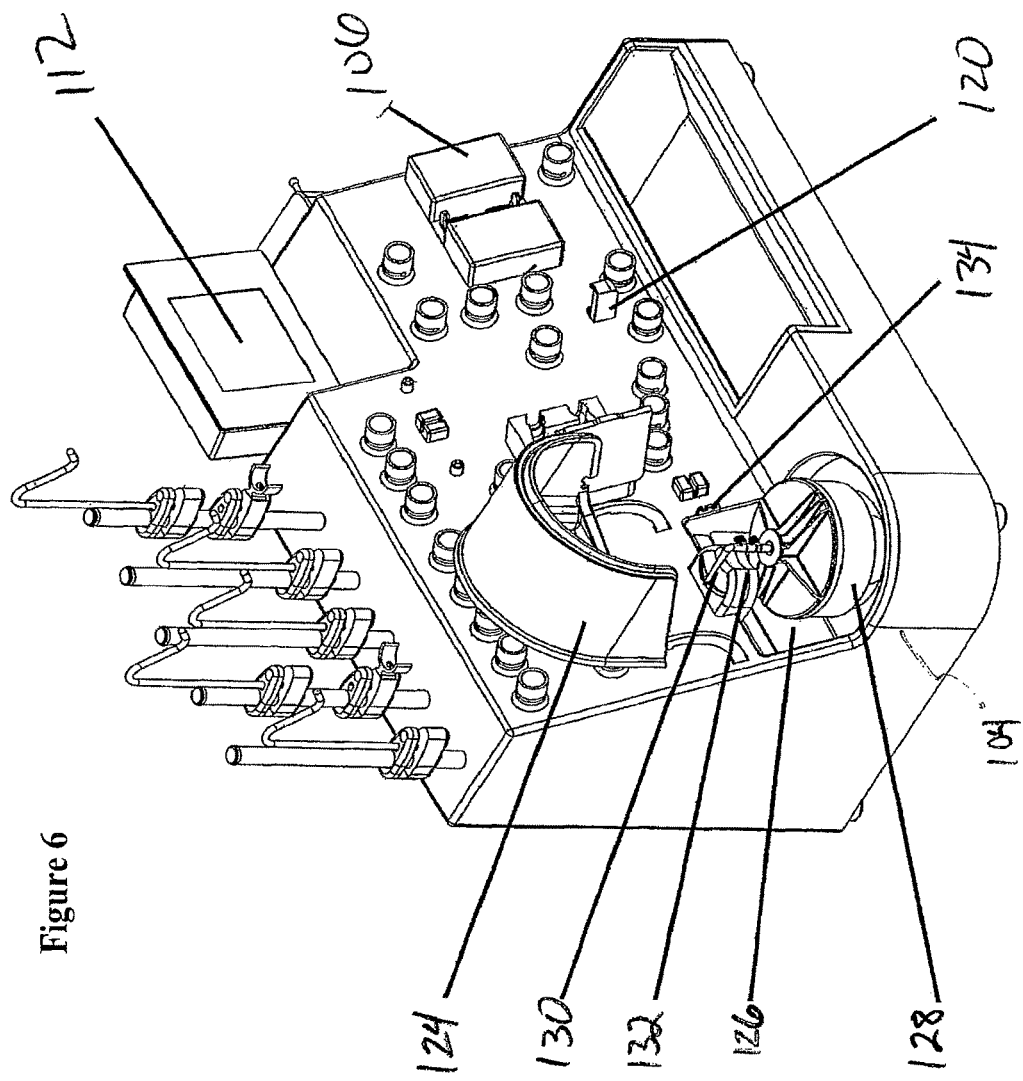

The system 100 is further illustrated with reference to FIG. 6. Processing unit 104 can include a housing or cover 124, that can be movable (e.g., removable) about one or more hinge. The cover 124 at least partially defines a processing area 126 that can be temperature controlled and coupled to temperature monitoring and control components that may be housed within the housing 105 of the system 100. The processing unit 104 includes a sample chamber 128 configured for holding and processing (e.g., centrifugation, culturing, sample component separation, etc.) of a sample. The sample chamber 128 shown is a rotating chamber held in position about an axis that can include an anti-rotation lock 130. The processing unit 104 can include one or more detection systems, such as an optical detector 132 positioned within the cover 124 and configured to detect or monitor processing of a sample in the chamber 128. One or more fluid input/output lines can be coupled to the chamber 128 and may be held in position by a holder 134.

Figure 7:
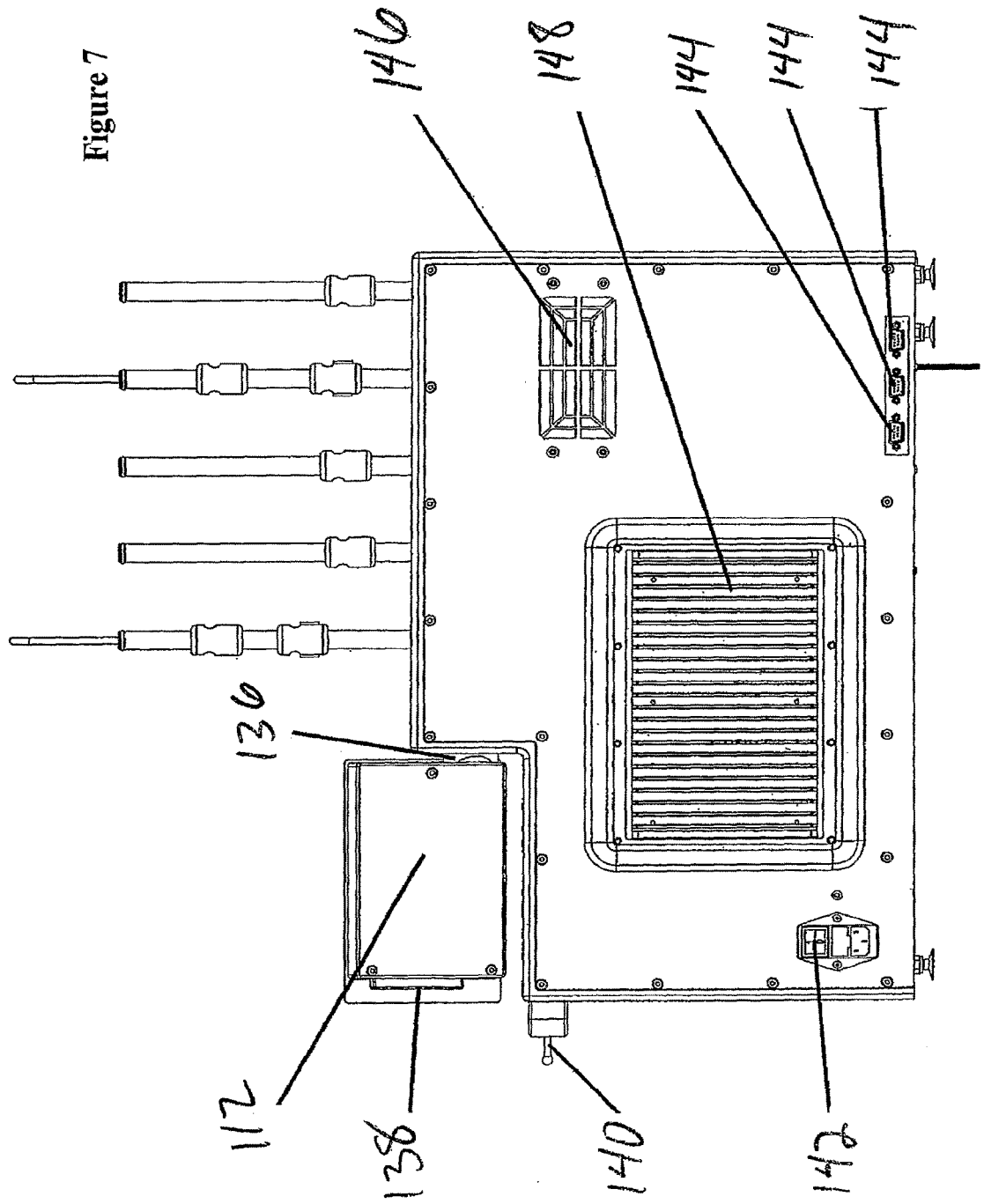

FIG. 7 illustrates a backside view of the system 100. The computer control unit 112 is shown with a component coupled to the system housing 105 about a rotational pivot, and the unit 112 having a storage media (e.g., program card) input slot 138. Hanger 140 is shown, which can provide support for external components, collecting equipment, etc. The system 100 includes power connect and switch 142 and various interface connects 144 (e.g., barcode reader connect, printer connect, network connect, etc.); vent 146; and heat sink 148 providing a component of internal temperature control systems.

Figure 8:
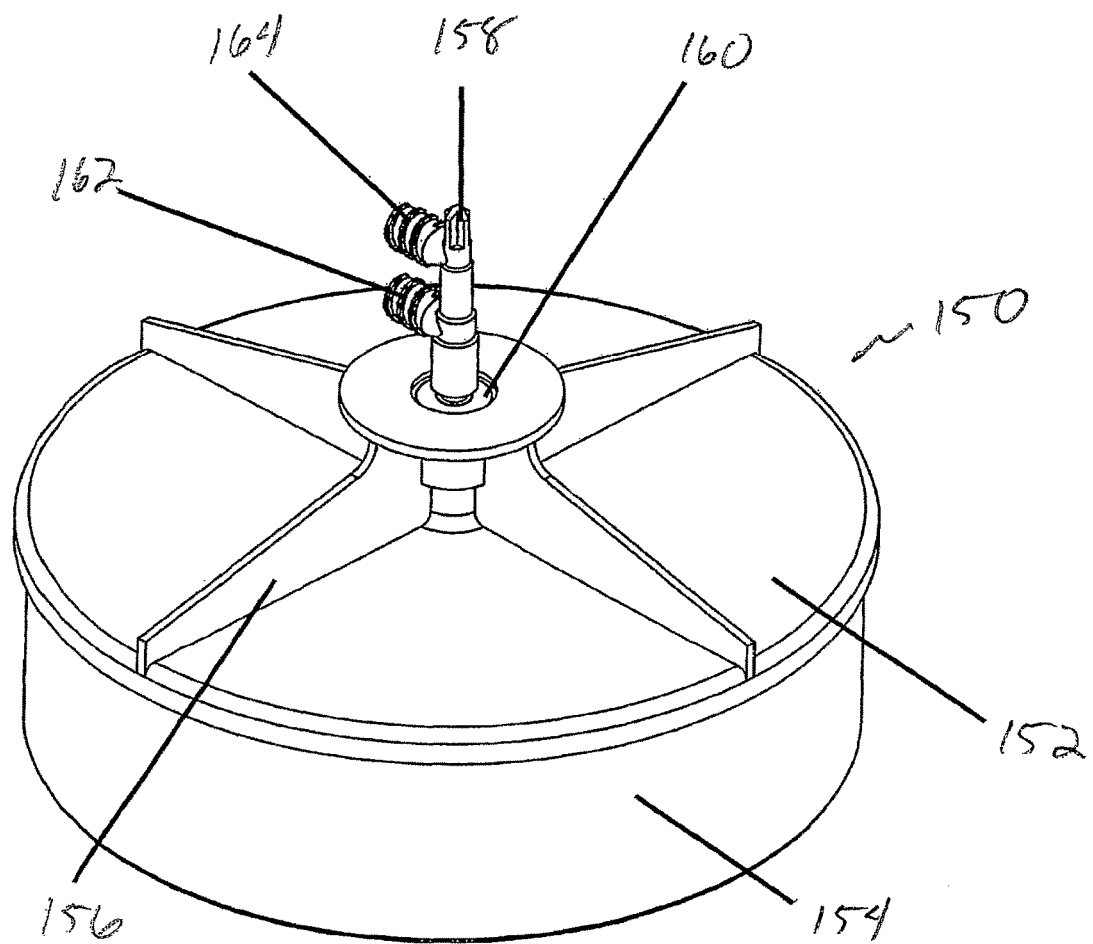
FIG. 8 illustrates a chamber of a processing system, according to an embodiment of the present invention.

Components of a processing unit, including a sample chamber, are further described with reference to FIGS. 8 through 12. Referring to FIG. 8, processing chamber 150 is illustrated having an upper portion 152 and a lower base portion 154. The upper portion 152 can include a reinforcement or support structure 156. The chamber 150 further includes an axis 158 about which the chamber 150 rotates, the axis 158 having a rotational lock, and the axis 158 extending through about the center of the chamber 150 and extending out the upper portion 152. Rotational means or bearing 160 provides rotational movement of the chamber 150 about the axis 158. The chamber 150 further includes fluid ports or line connects 162, 164 coupled to a housing structure surrounding the axis 158, and ports 162, 164 fluidly connected to one or more internal compartments of the processing chamber 150.

One of the ports may be used as vent to exchange gases.

Figure 9:
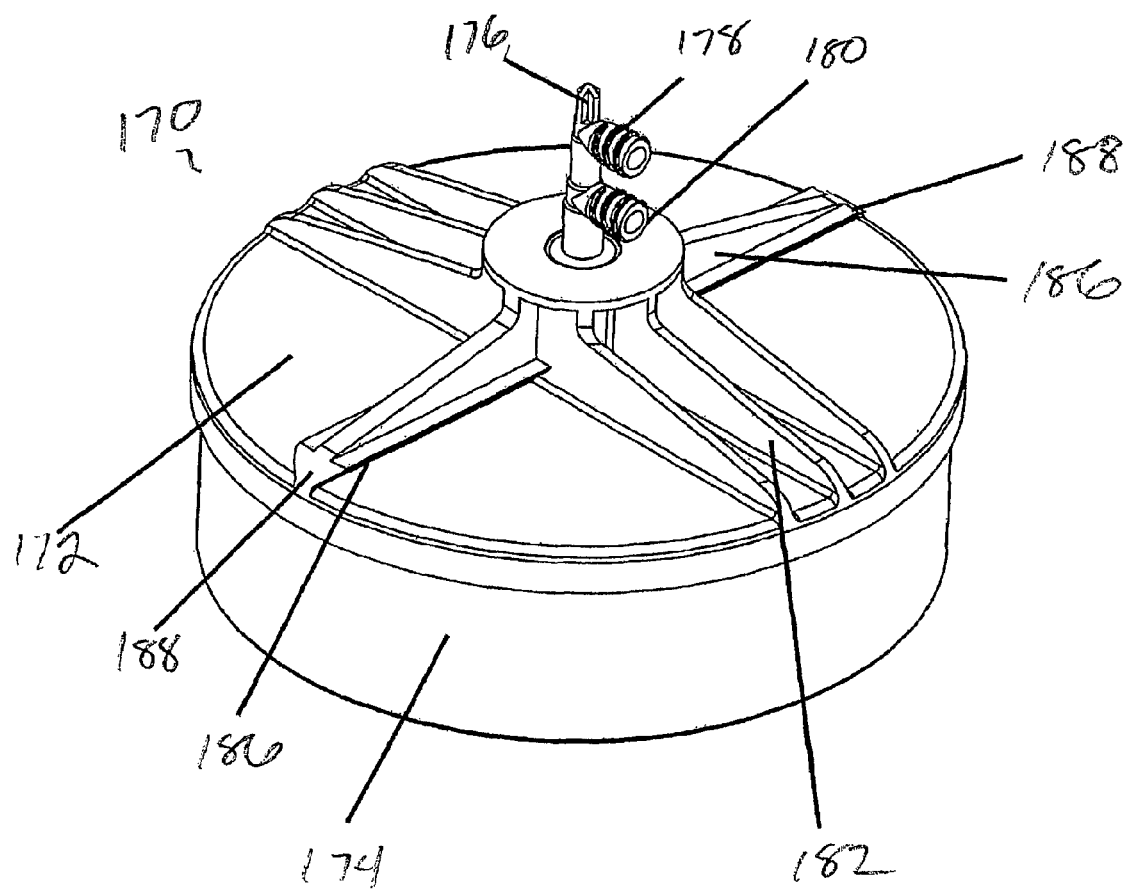
FIG. 9 illustrates a chamber of a processing system, according to another embodiment of the present invention.

A processing chamber according to another embodiment of the present invention is described with reference to FIG. 9. The chamber 170 includes an upper portion 172 and a lower portion 174, with a rotational axis 176 and ports 178, 180 configured similarly as described above. The upper portion 172 includes a support structure 182 as well as structure 184 including a channel 186 that can include at least a portion visible through a window or prism 188.

The channel 186 can be fluidly coupled to a sample containment compartment in the chamber 170 and configured for external monitoring or detection of sample processing. For example, a component (e.g., cells) in fluid in the channel 186 may become visibly separated during processing steps, thereby indicating separation of cells or sample components in one or more internal compartments of the chamber.

The chamber 170 may further comprise at least one vent, preferentially comprising a sterile, hydrophobic membrane or tampon. Preferably these membranes or tampons may be located at the top or bottom of the chamber. The at least one vent in the chamber has the particular advantage that the volume in the chamber can be changed easily without changing the pressure in the chamber or providing further inlet an/or outlet ports for the exchange of air or gas.

The centrifuges of the present invention permit a batchwise as well as a continuous centrifugation: sample, media, gases and other materials can enter and leave the system e.g. through inlet and outlet ports (e.g. 178 and 180 in FIG. 1) without a need of stopping the rotation of the centrifugation chamber and refilling the centrifuge (batch-wise centrifugation). This allows a continuous concentration of the sample and the product may be removed only once at the end of the centrifugation thus avoiding potential contamination due to additional handling.

Figure 9A:
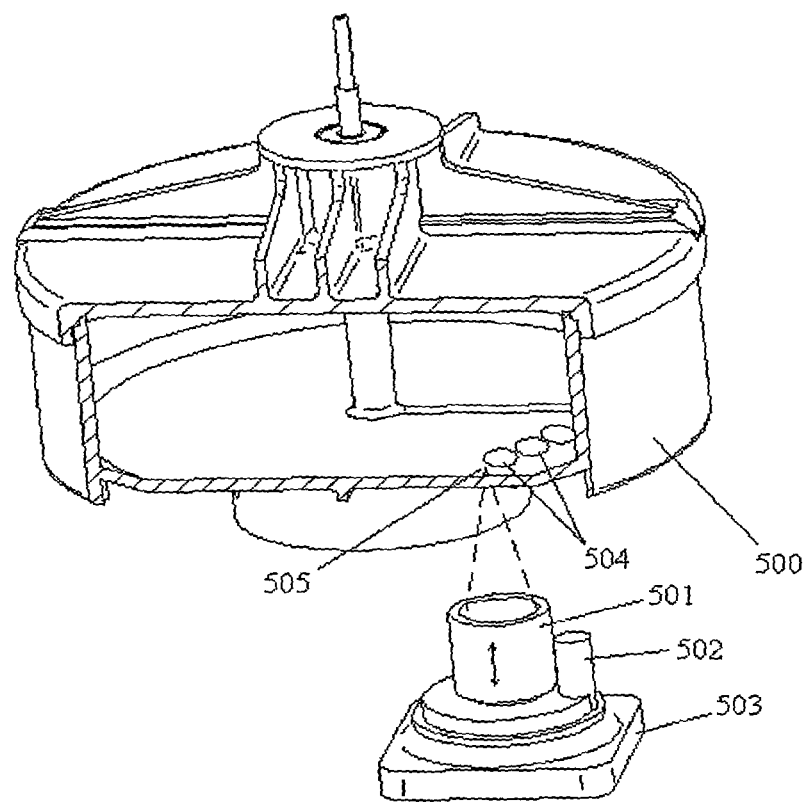
FIG. 9A illustrates a chamber of a processing system, according to an embodiment of the present invention.

In FIG. 9*a*, a rotating container or centrifugation chamber 500 is shown. At the bottom of the rotating chamber 500 a microscope focus area 505 is positioned which comprises at least one sensor pad 504. Below the rotating chamber 500, a microscope camera module 503 is located that comprises a microscope optics 501 and a microscope drive motor 502 for focusing the optics. The microscope optics 501 is configured such that is can focus automatically to detect the sample that is being separated into at least two components during centrifugation. Thereby, the microscope camera module 503 can be used to detect different layers formed by the separated sample in the chamber 500 due to centrifugal forces. In addition, the pH value of the sample components can be measured. For this purpose, an indicator is used in the chamber 500 that changes its color dependent on the pH value that is present. Moreover, it is possible that the temperature of the sample in the chamber be measured using liquid crystals that are position in the chamber such that their position can be detected with a microscope camera module 503 from the outside. Thereby, the temperature in the chamber 500 can be determined.

The microscope camera module 503 can be mounted in a movable fashion, such that the module 503 can be directed with its microscope optics 501 at different sensor pads 504 located in the wall of the chamber 500. This facilitates the detection of various layers formed in the chamber 500 or the detection of the pH or the temperature at different positions within the chamber 500.

Figure 10:
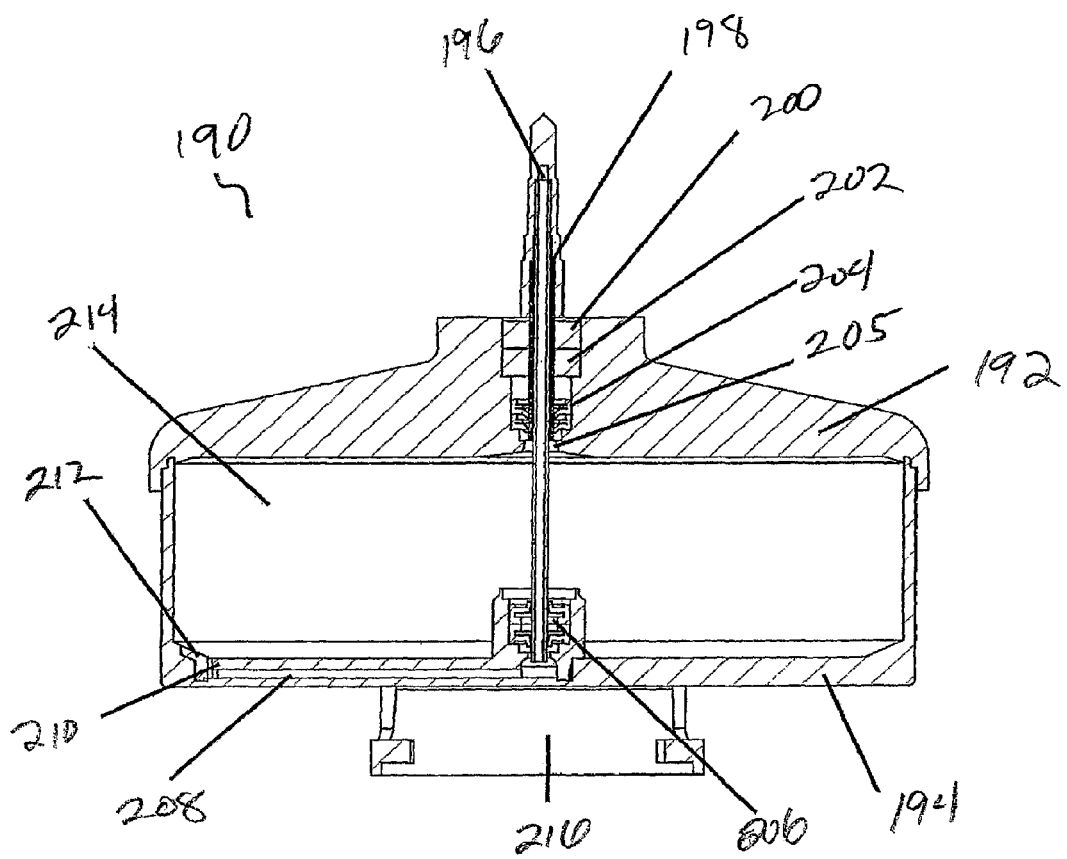
FIG. 10 shows a cross-sectional view of a processing chamber, according to an embodiment of the present invention.

FIG. 10 illustrates a cross-sectional view of a sample processing chamber according to an embodiment of the present invention. The chamber 190 includes an upper portion 192 and a base portion 194, and one or more internal compartments. The chamber 190 is configured to rotate about an axis so as to apply a centrifugal force to a sample disposed in one or more compartments in the chamber, thereby separating at least two components of the sample. The chamber includes central line 196 fluidly connected to at least one compartment of the chamber. Components of the chamber 190 further include outer line 198; rotational bearing 200, rotational seals 202, 204, 206; outer entry line to the chamber 205; lower radial channel 208; inner line entry 210 to a chamber compartment; slant 212, and deflector 214. Chamber retainer 216 is included and configured for secure positioning/coupling of the chamber 190 with other components of a system of the invention.

The centrifugation chamber 190 preferably comprises a rotating seal, optionally with two fluid lines, preferably with two fluid lines. The fluid lines can enter the chamber 190 at different position. For example, it is possible to position a first fluid line at the outer perimeter of the upper portion 192 (lid). A second fluid line could be positioned further inward, e.g. 2 mm to 20 mm further towards the center of the chamber 190. Optionally, a vent can be located at the upper portion 192, e.g. in the form of a membrane.

Generally, the position of openings such as holes or line entries in the centrifugation chamber can be configured such that they are best suited for the centrifugation of a particular sample. Depending on the components of a particular sample, and the relative volume of each component in the sample, the openings can be positioned so that the removal and/or detection of a particular component can be achieved.

Figure 10A:
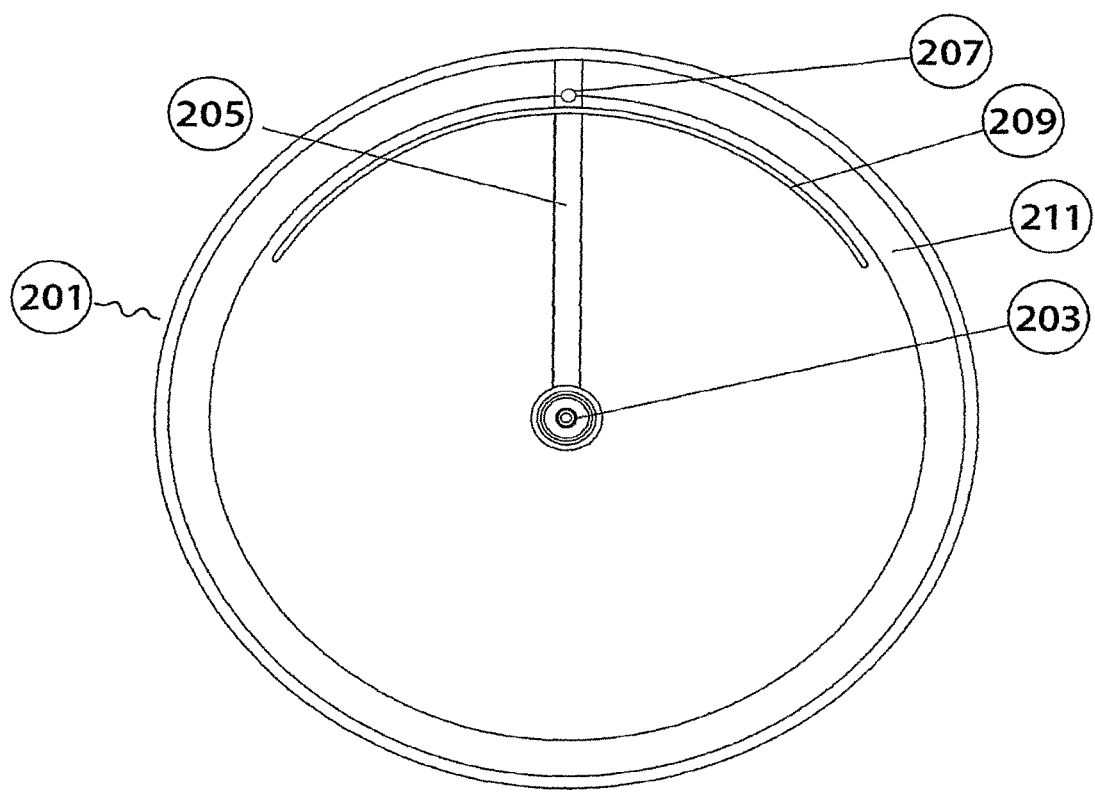
FIG. 10A illustrates a top plan view of a processing chamber, according to an embodiment of the present invention.

FIG. 10A illustrates a top plan view of a chamber 201. The chamber 201 includes an inner line 203, lower radial channel 205, inner line entry 207 to the chamber, optionally a deflector 209, a slant 211 and a light pass 209.

Figure 11:
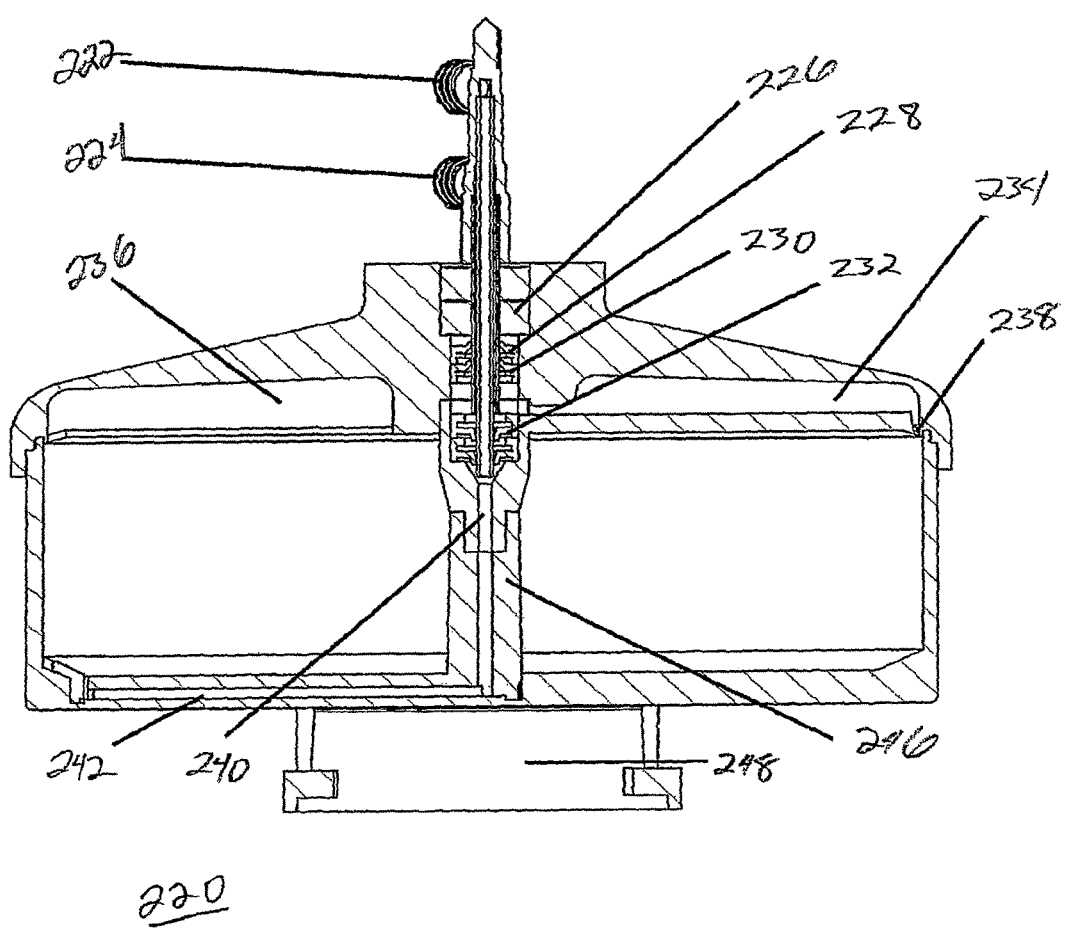
FIG. 11 shows a cross-sectional view of a processing chamber, according to another embodiment of the present invention.
Figure 11A:
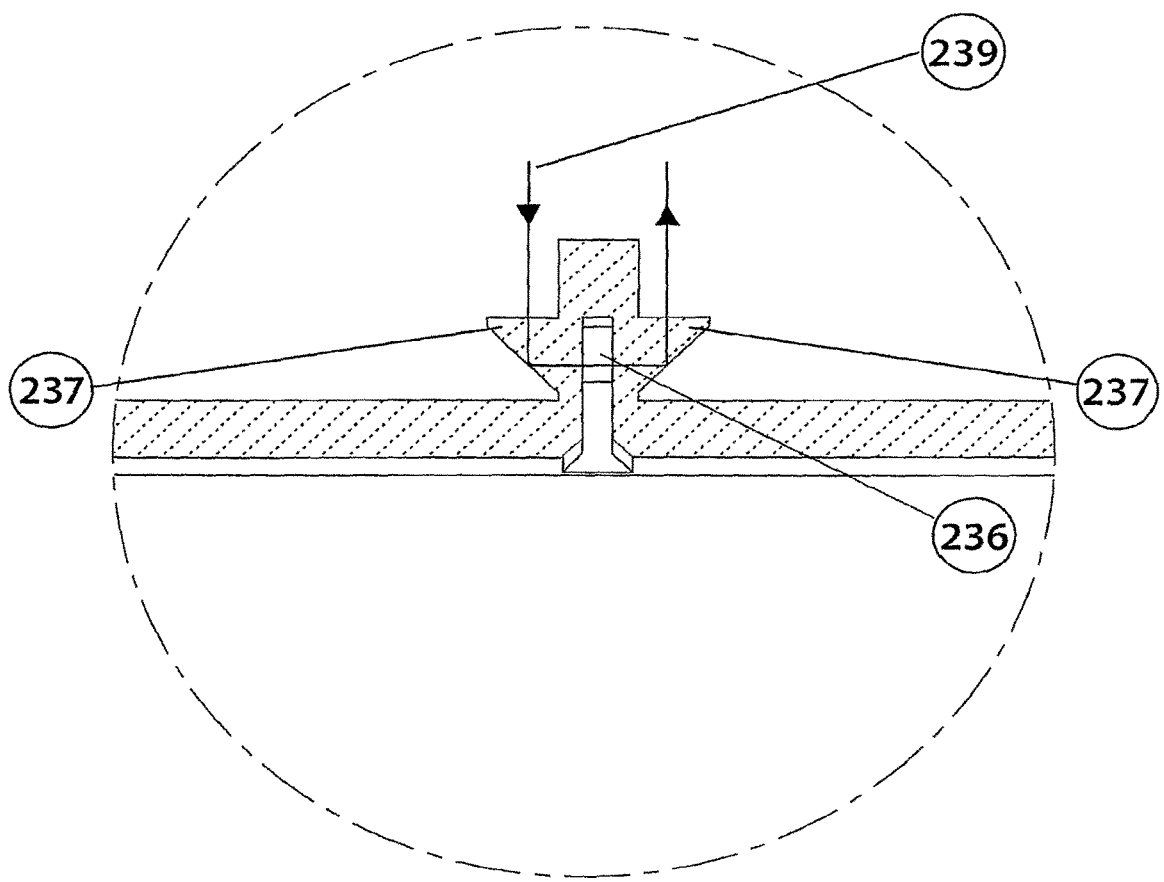
FIG. 11A illustrates a focused view of a portion of a processing chamber as shown in FIG. 11.

FIG. 11 illustrates a cross-sectional view of a chamber according to another embodiment of the present invention. The chamber 220 includes an axis about which the chamber rotates, a central line connect 222 and a outer line connect 224, and one or more internal compartments. Further illustrated are rotational bearing 226, as well as rotational seals 228, 230, 232; inner channel 234, optical detection channel 236 (similar to described above); inner line entry 238 to the chamber; inner line 240, and lower radial channel 242. The chamber further includes an inner reinforcement 246 and a chamber retainer 248. FIG. 11A illustrates a focused view of portion of a chamber 220 is described above. Shown are an optical detection channel 236, a prism 237, and light pass 239 (further indicated by arrows).

In another embodiment of the present invention, the bottom of the chamber can possess one or more openings (FIG. 12A, 291) covered with a hydrophobic membrane 292. These openings can be used for gases to be delivery into or removed from the chamber, for instance for cell culture processes. The membrane can be glued, thermally, ultrasonic or by other means bonded to the bottom of the chamber in a way to assure sterile connection with the chamber.

In another embodiment of the present invention (FIG. 12B), the chamber can possess a system of channels for the gas flow, for instance channels assembled as a spiral system 293, which assures a large contact area between the gases and a membrane bonded over the channels (not shown). These channels may be located at the bottom or the top of the chamber. The channel system possesses at least one input (opening) 294 and an optional output (opening) 295 for the gases.

The entries or ports of the channels of FIGS. 8-11A may vary in number and location within the channel.

Figure 12:
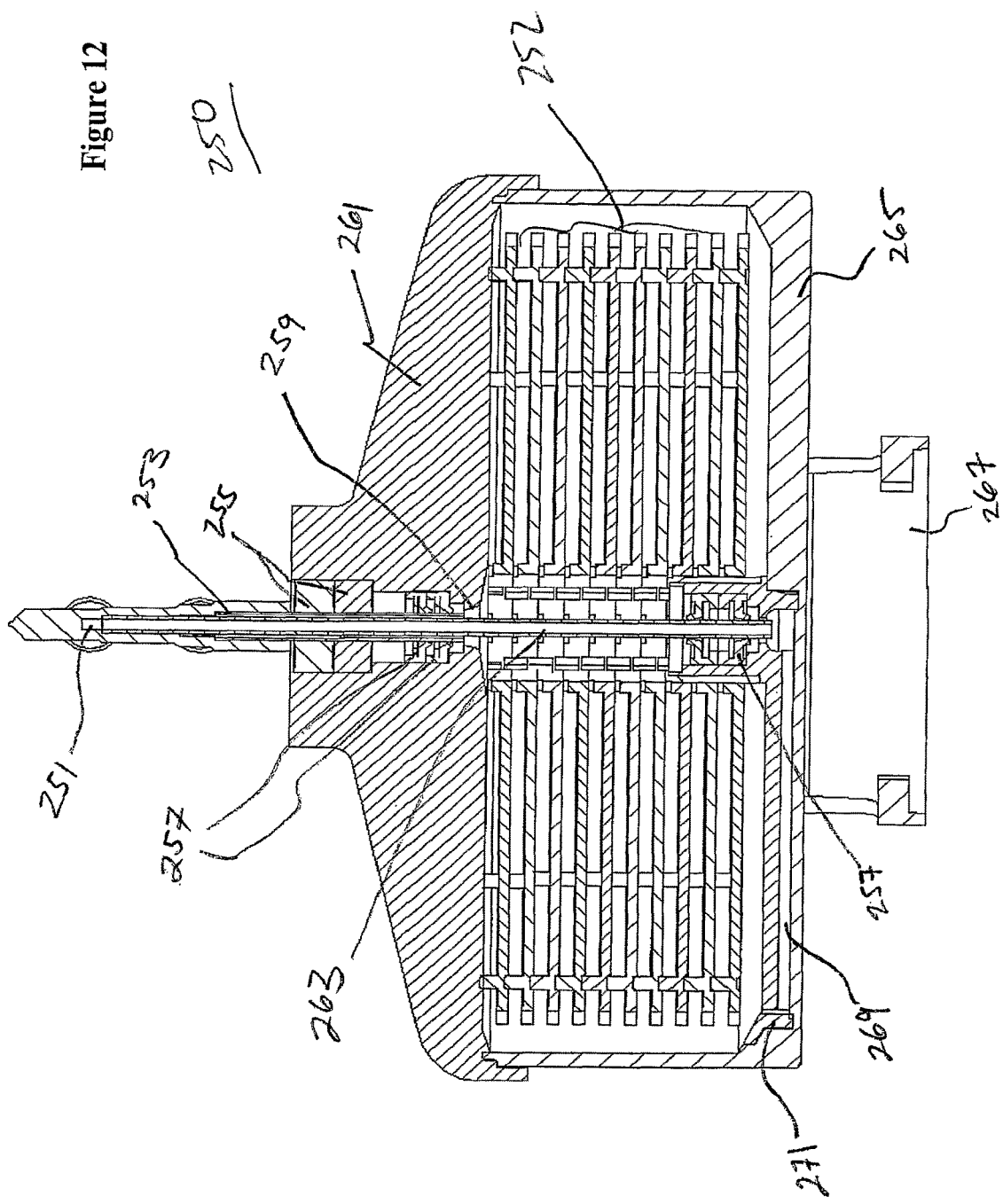
FIG. 12 shows a cross-sectional view of a processing chamber, according to yet another embodiment of the present invention.
Figure 12A:
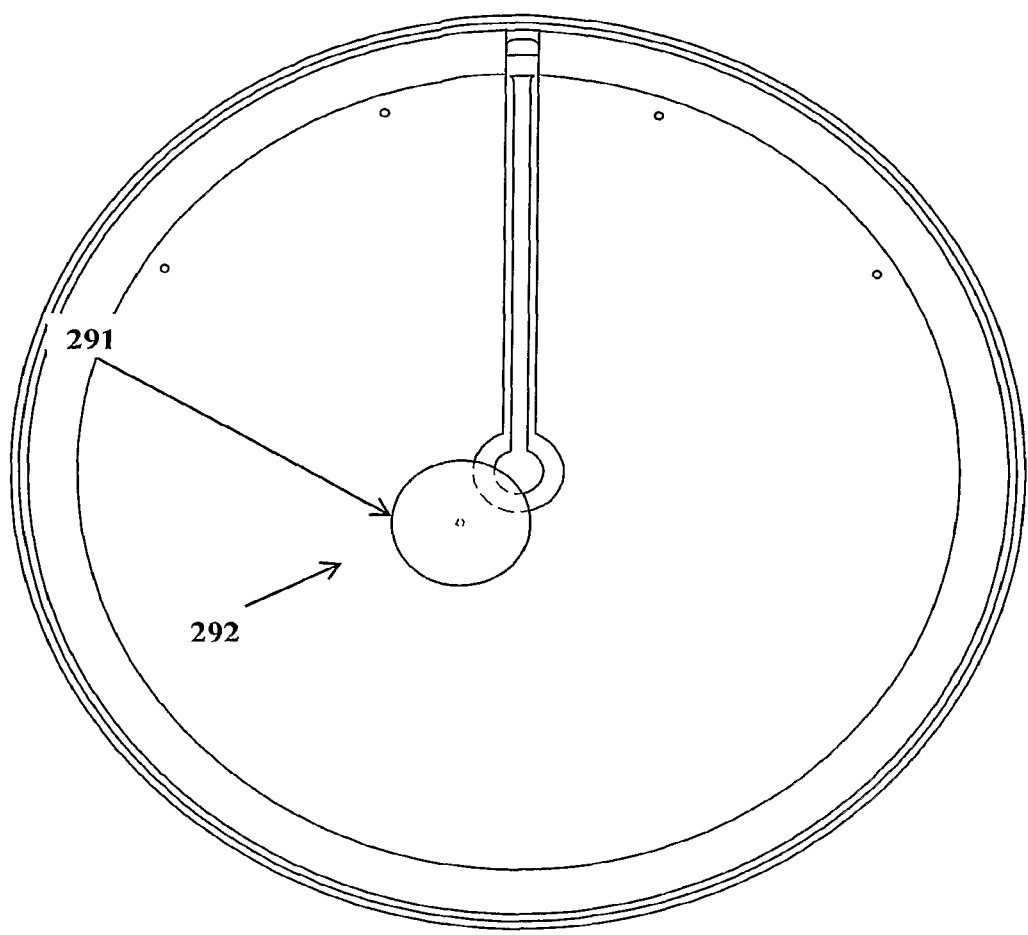
FIG. 12A shows a view over the bottom of the process chamber with an opening for gas delivery and a bonded hydrophobic membrane.
Figure 12B:
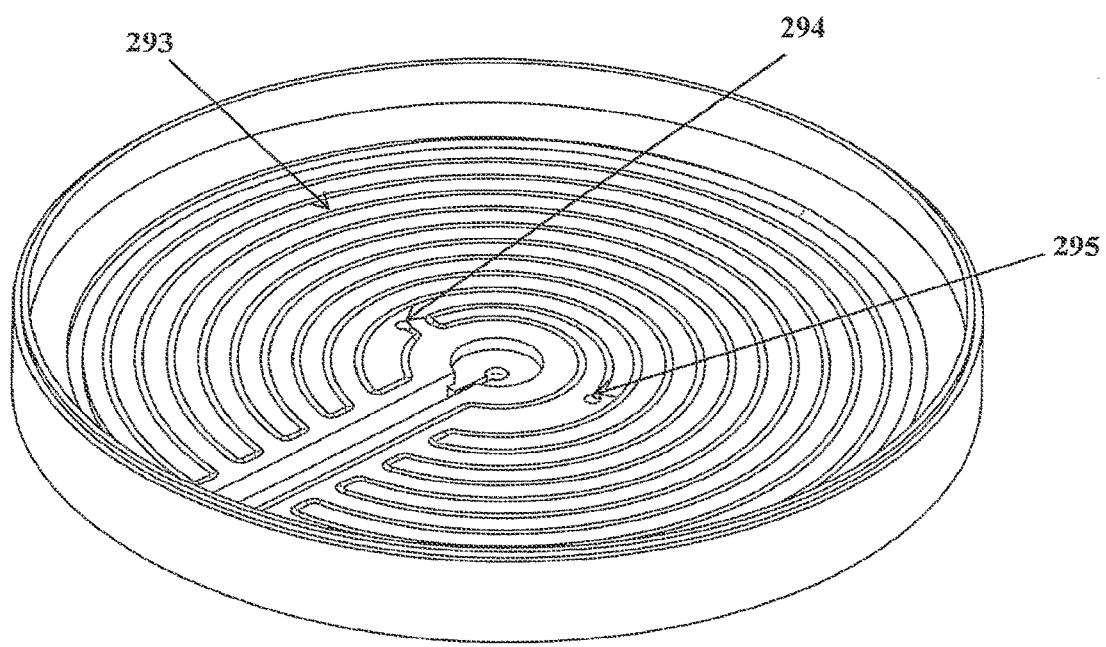
FIG. 12B shows the bottom of the chamber with spiral channels for aeration through membrane bonded to the bottom of the chamber.

FIG. 12 illustrates a cross-sectional view of a chamber according to another embodiment of the present invention. Construction of chamber 250 is similar in many regards to chambers as described above, but further includes a plurality of layered structures 252. The layered structures 252 can be configured to provide cell culture structures or layers. In use, sample including cells can be introduced into the chamber and flowed over layers 252. Separation processing can include rotation of the chamber such that cells adhering to the layers are separated from those with lesser affinity for the layers. Intermittent rotation and/or breaking during rotation can further disconnect cultured cells from the surface of the layered structures 252 for separation processing. Surprisingly, it was found that this intermittent process is also able to resuspend clumped or attached biological material, like cells after culturing. The chamber further includes illustrated central line 251, outer line 253, bearing 255, rotational seals 257, outer line entry 259 to the chamber, upper portion 261, inner channel 263, base portion 265, retainer 267, lower radial channel 269, and inner line entry 271 to the chamber.

The chamber may comprise or may be made of various materials. In a preferred embodiment, transparent materials are used like plastics, polystyrol (PS), polysterene, polyvinylchloride, polycarbonate, glass, polyacrylate, polyacrylamide, polymethylmethacrylate (PMMA), and/or polyethylenterephtala (PET). Polytetrafluorethylen (PTFE) and/or thermoplastic polyurethane (TPU), silicone or compositions comprising one or more of the above mentioned materials. The chamber can also be made of polyethylene (PE). In a preferred embodiment, the layers in the chamber comprise or are made of collagen, chitin, alginate, and/or hyaluronic acid derivatives. Possible are also polyactide (PLA), olyglycolida (PGA) and their copolymers, which axe biodegradable. Alternatively, non-biodegradable materials can be used, such as polystyrol (PS), polysterene, polycarbonate, polyacrylate, polyethylene (PE), polymethylmethacrylate (PMMA), and/or polyethylenterephtala (PET). Polytetrafluorethylen (PTFE) and/or thermoplastic polyurethane (TPU) can also be used. Other alternatives include ceramics and glass materials, like hydroxylapatite (HA) or calcium phosphate. The layers in the chamber can be of solid material or porous.

In a preferred embodiment the chamber has a size of 2 cm to 50 cm in diameter and a height of 5 mm to 50 cm. Centrifugation is preferentially carried out up to 1000×g.

The number of the layers and the distance between the layers is variable.

In a preferred embodiment, the chamber can be heated and cooled to provide for a temperature appropriate for the sample to be centrifuged. For this purpose, a heating and/or cooling means is located in the system.

Figure 17:
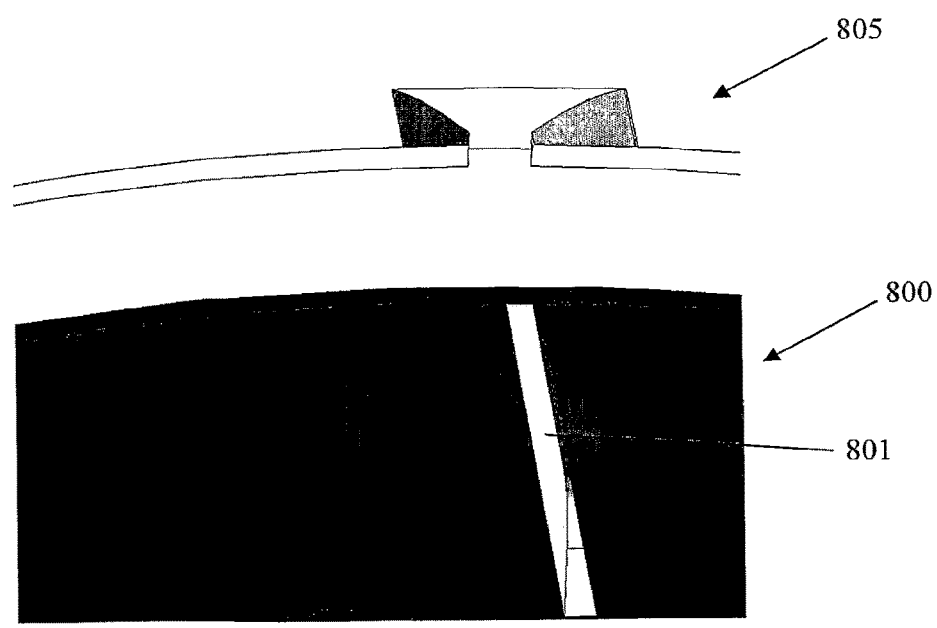
FIG. 17 shows a view of the inside of a lid for a rotating chamber with a channel or gap in which the sample flows during centrifugation, with a means for detecting the progress of separation of the sample in the form of a prism.

As shown in FIG. 17, the cylindrical shaped centrifuge chamber my be limited on its upper side by a lid 800, which may carry one or more stabilizing ribs 805 on the flat top surface. At least one of these radial ribs 805 can cover a narrow gap or channel 801, open to the centrifuge's inner volume when the lid 800 is tied on the centrifuge chamber. The gap 801 extends in axial direction from the inner lid surface passing the lid 800 some millimeters into the rib 805. Therefore, it may be visible from the outside within the rib 805 when transparent material is used. In radial extension, the gap 801 reaches from near the center up to the cylindrical centrifuge wall (FIG. 17).

During centrifugation, the same forces take effect in the gap 801 as in the whole centrifuge chamber. The ring shaped neighbored suspension layers extend parallel into the gap 801 and are displayed as axial standing neighbored thin areas, like a thin layers cross cut, well detectable by external optical sensors.

The gap 801 width can be determined freely, also small enough for a transmitted light analysis of all layer-associated areas in the gap. Thereby, it is possible to quantify the optical densities and colors of all layers of the suspension in the centrifuge chamber in a "touchless" manner from the outside through optical transmission measurements.

To enable a vertical illumination and sensor position to watch the layers movements in the gap, a window, a mirror or preferentially a prism can be added on both rib sides, which may preferably be preformed by the transparent housing material itself.

Figure 18:
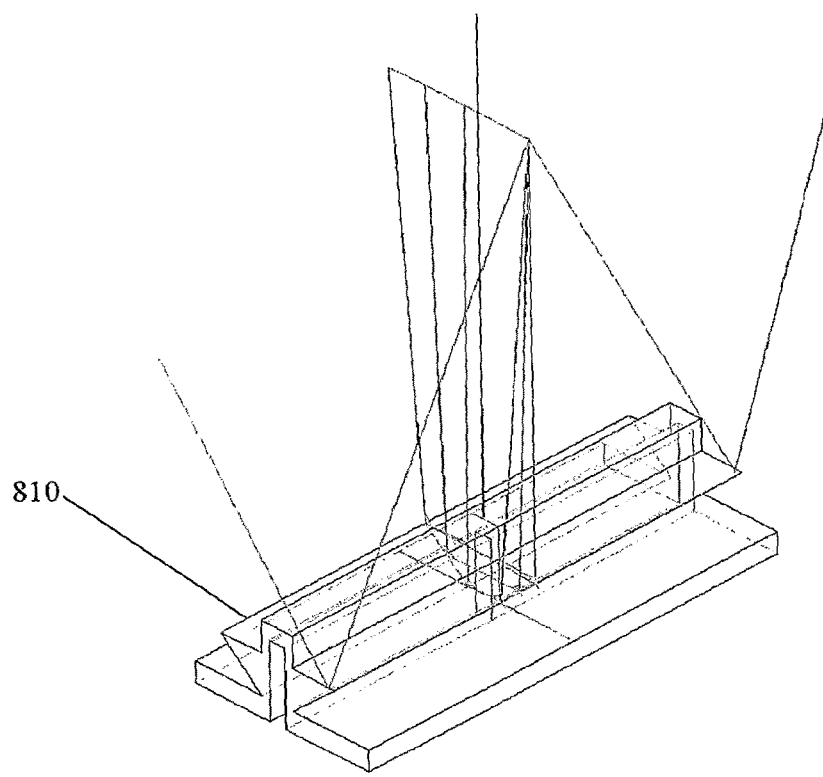
FIG. 18 shows the path of light through the sample by means of a prism. The prism (double prism) is configured such that light from a light source can at least partially penetrate through at least a part of the sample that is being separated through centrifugation, and light passing through at least a part of the sample can be detected by a light detector.

The prism 810 refracts the vertical generated illuminating beam through the gap (horizontal) and back to the top, vertical again (FIG. 18). During centrifugation, a synchronous position triggered electronic flash light can transmit light into one side of the prism 810, e.g. the left prism, illuminating the gap by refraction. The transmission result is refracted by the other side of the prism 810, e.g. the right prism, back to a vertical mounted sensor or camera, possibly in the neighborhood to the upper flash source on the top. The resulting optical sensor unit is easy to handle like a reflex sensor but at the same time allows for full-scale transmission measurements.

Figure 19:
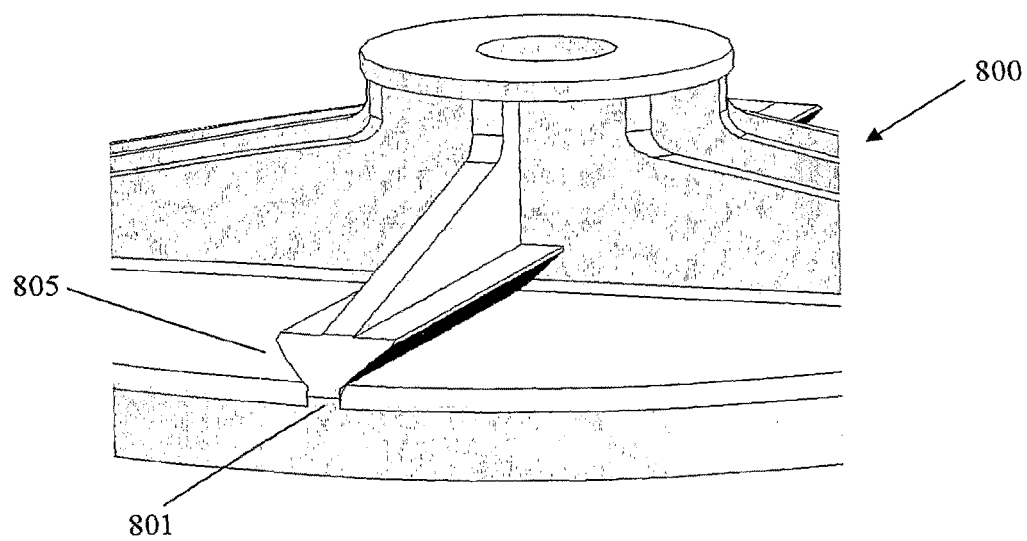
FIG. 19 shows a double prism that is part of a rib located at the lid of the rotating chamber.

The arrangement of the prism's angels ensures the "total reflection" on its inner prism surface for the illuminating flash beams and avoids direct reflections on its outer surfaces between light source and camera. Therefore, there is no need for mirror coatings and injection molding technologies can be used without rework of the facilities being required (FIG. 19).

Figure 13:
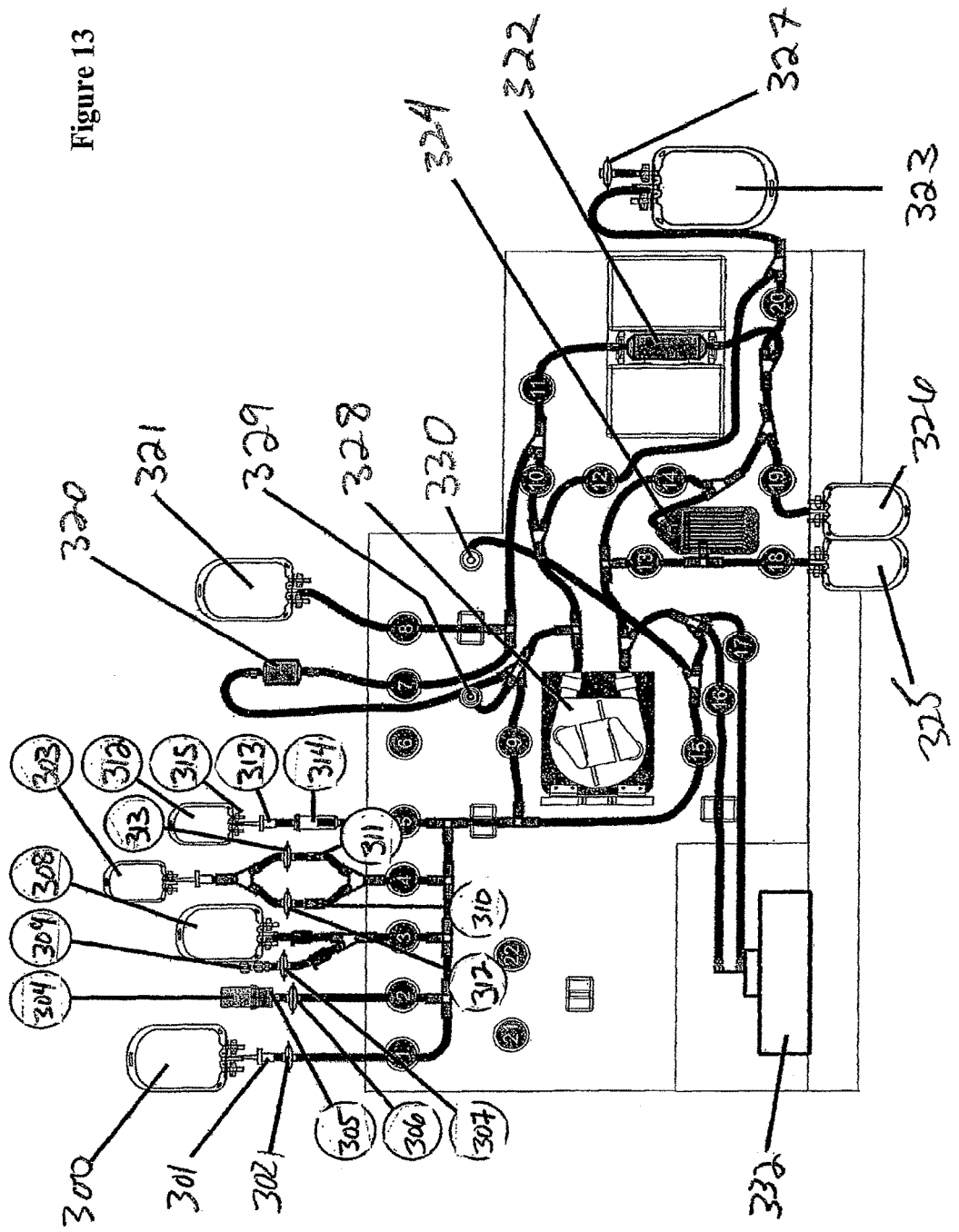
FIG. 13 illustrates a system according to an embodiment of the present invention.

Another embodiment of the present invention is described with reference to FIG. 13. As illustrated, a processing system including various coupled components, flow channels, buffers, reagents, etc. It will be recognized that numerous configurations are available and that the current configuration is provided for illustrative purposes. Referring to FIG. 13, components include a system buffer 300, spike port 301, sterile filter 302, plasma/in process bag 303, magnetic labeling reagent container 304, spike port 305, magnetic reagent sterile filter 306, sterile filter 307, buffer/media bag 308, cell culture media port, auxiliary port 309, single direction valve downwards 310 possibly including a filter, single direction valve upwards 311, sample bag 312, sample bag connector 313, sample filter 314, sample port 315, filter 316, pre-separation filter 320, in process storage bag 321, magnetic separation column 322, waste bag 323, volume reduction unit 324, positive fraction bag 325, negative fraction bag 326, sterile air filter 327, pump 328, air filter to pressure sensor1 329, air filter to pressure sensor2 330, sample/cell processing unit 332.

Figure 14A:
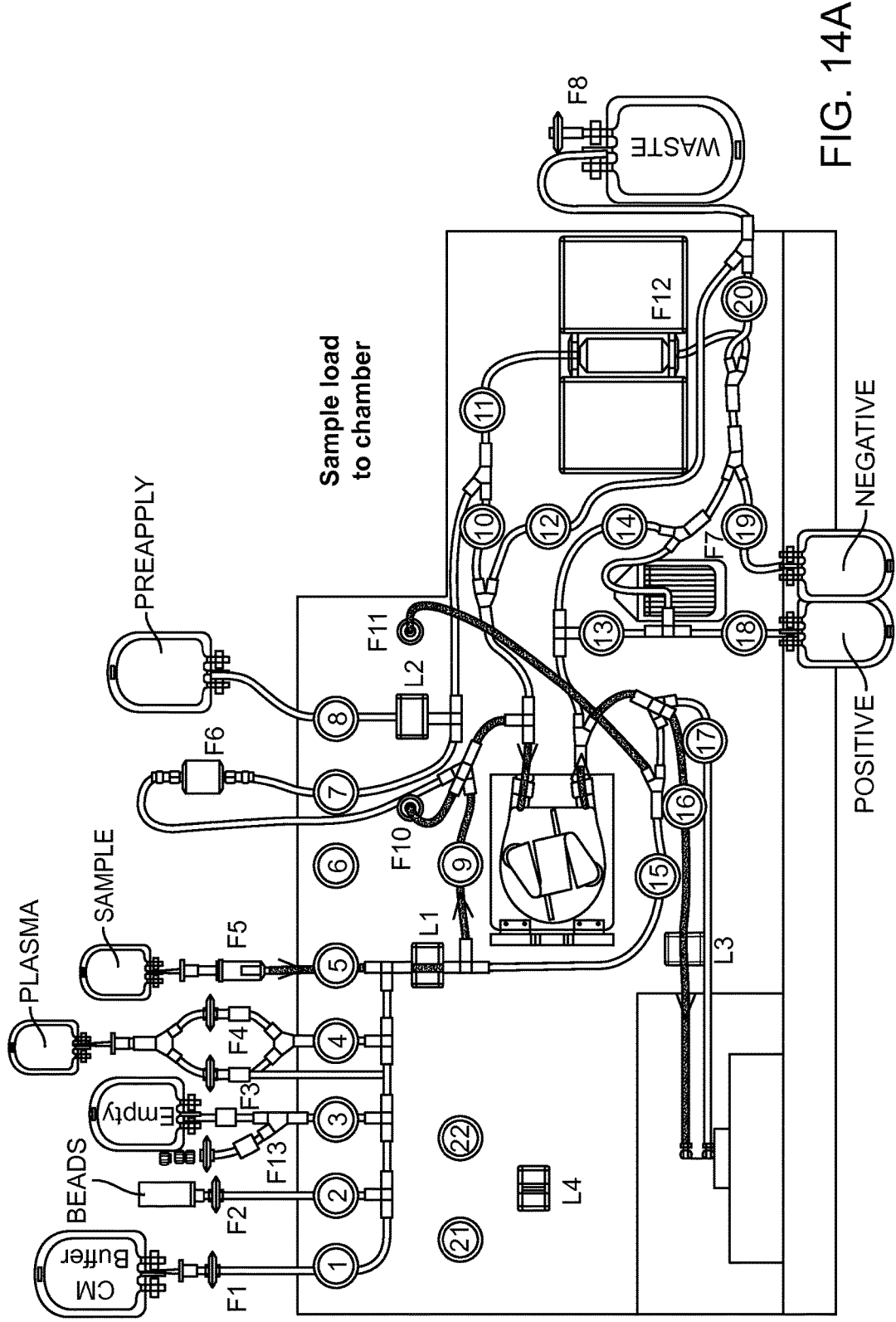
FIG. 14A through 14N illustrate an exemplary sample processing method according to an embodiment of the present invention.
Figure 14B:
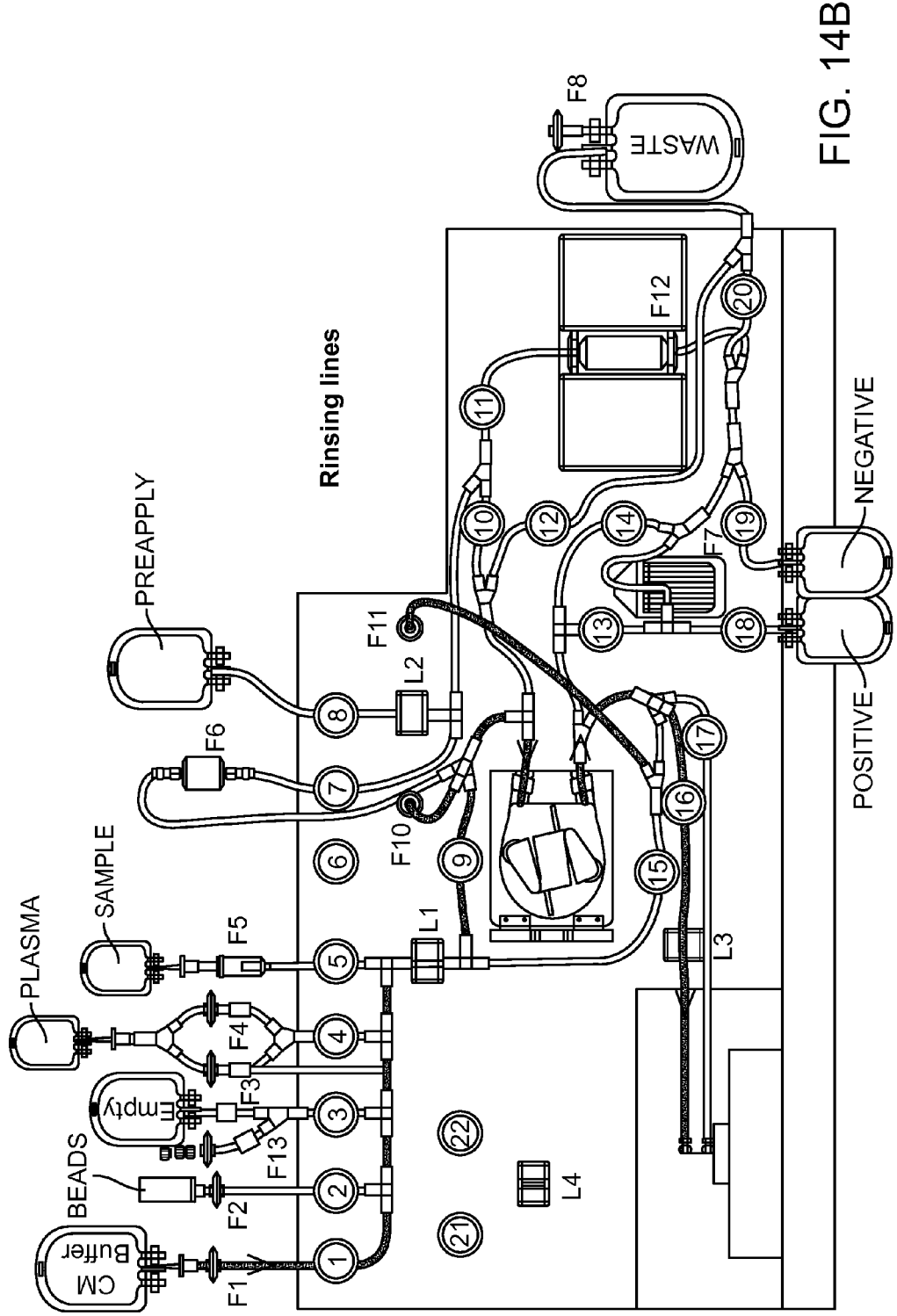
Figure 14C:
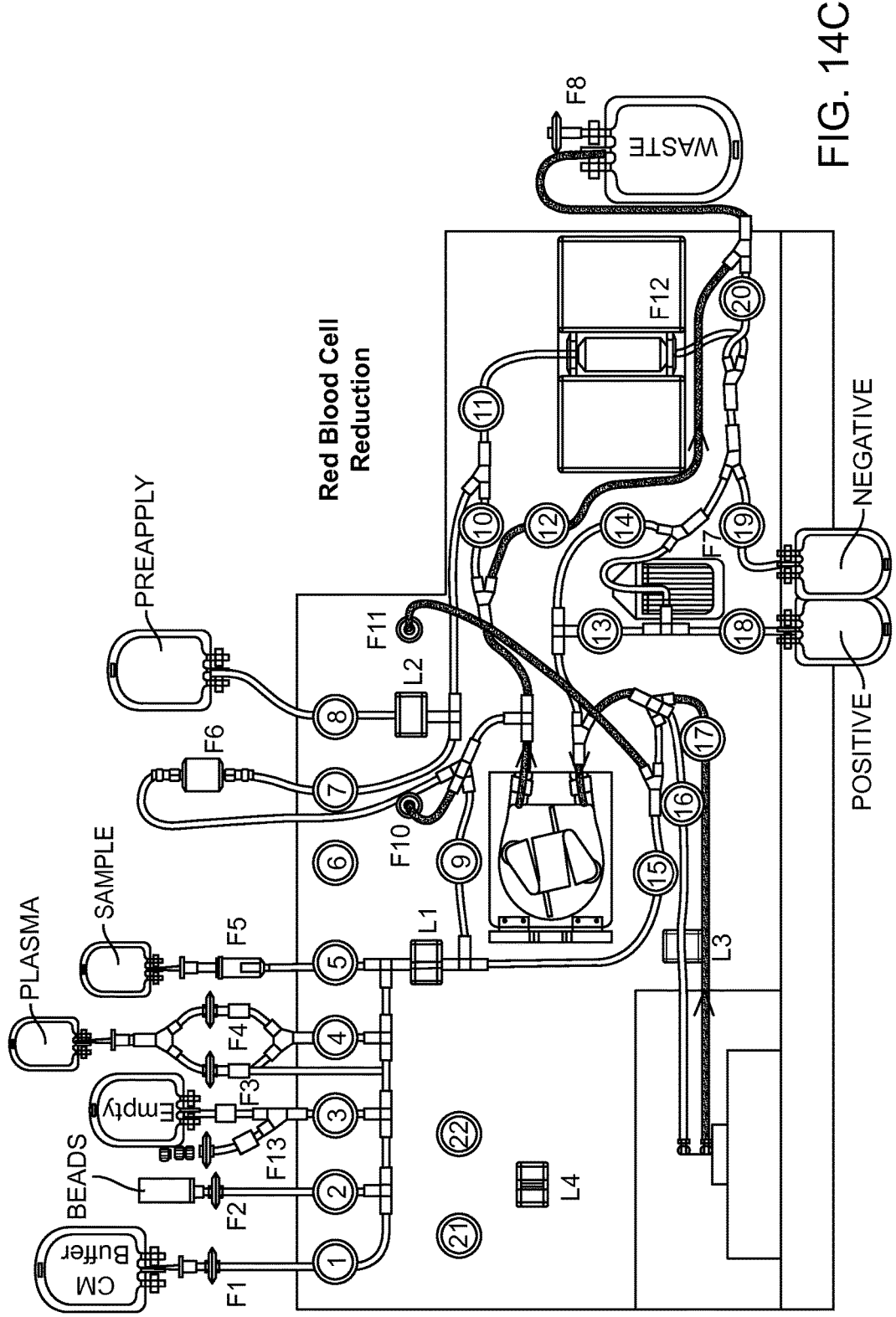
Figure 14D:
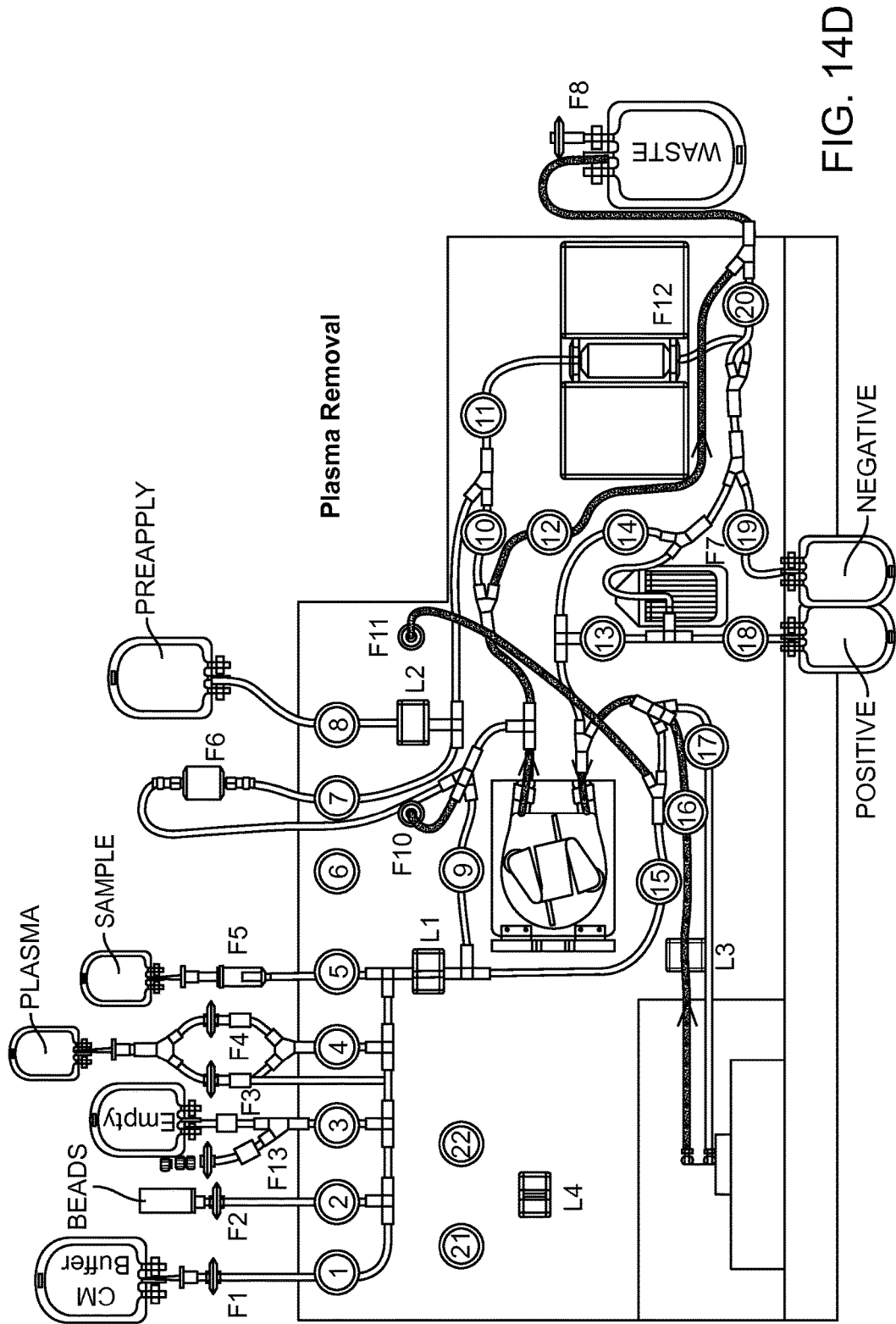
Figure 14E:
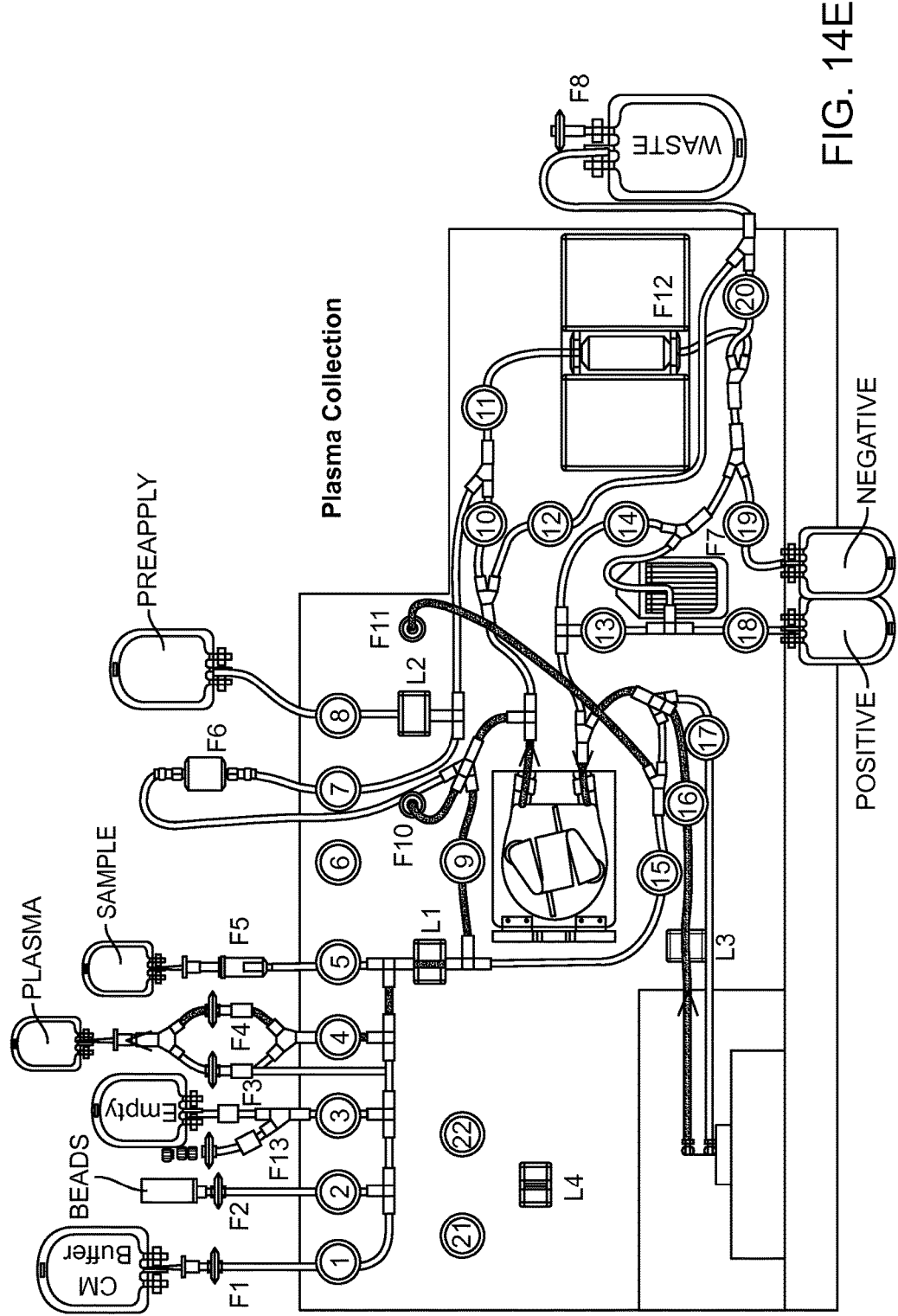
Figure 14F:
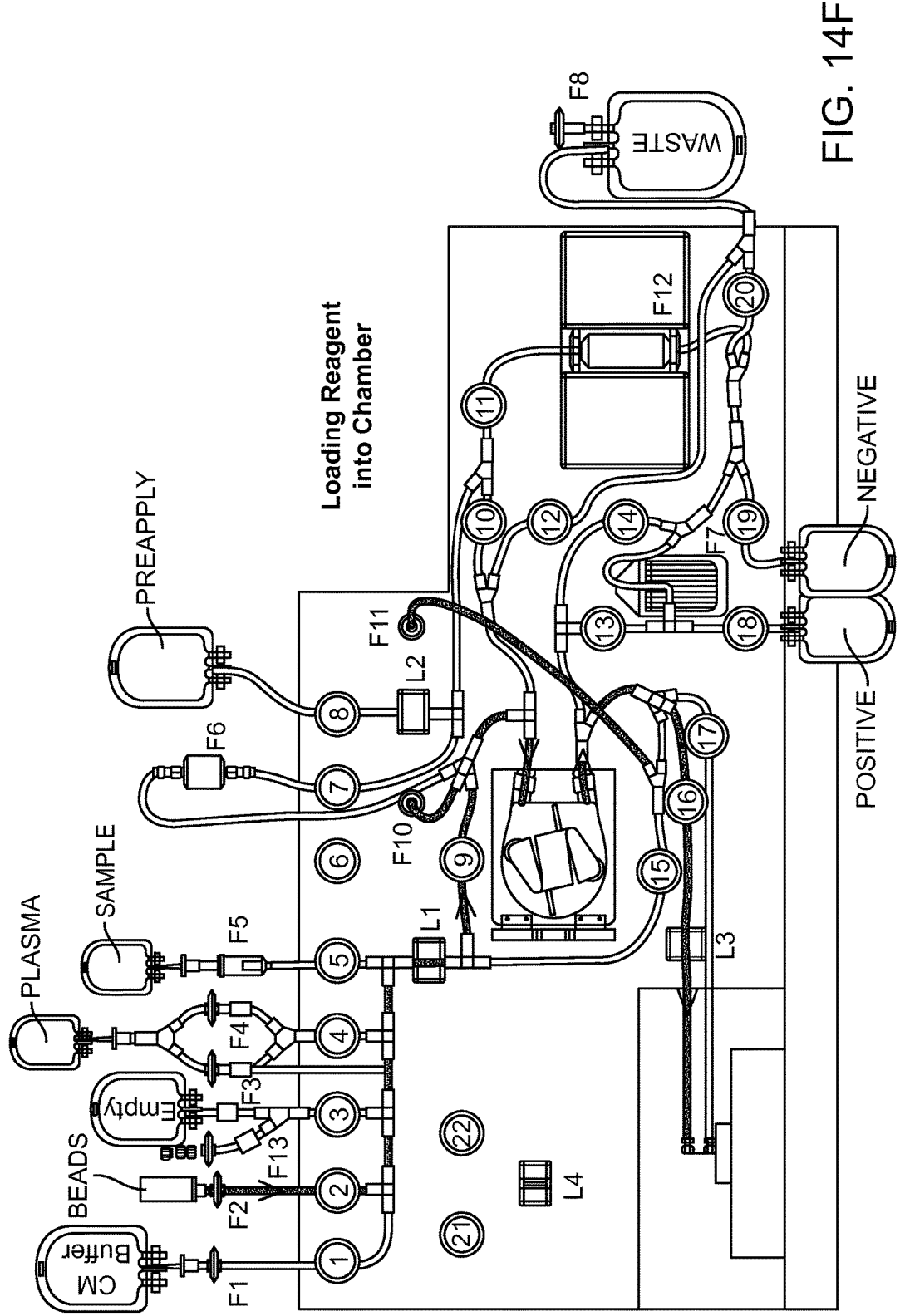
Figure 14G:
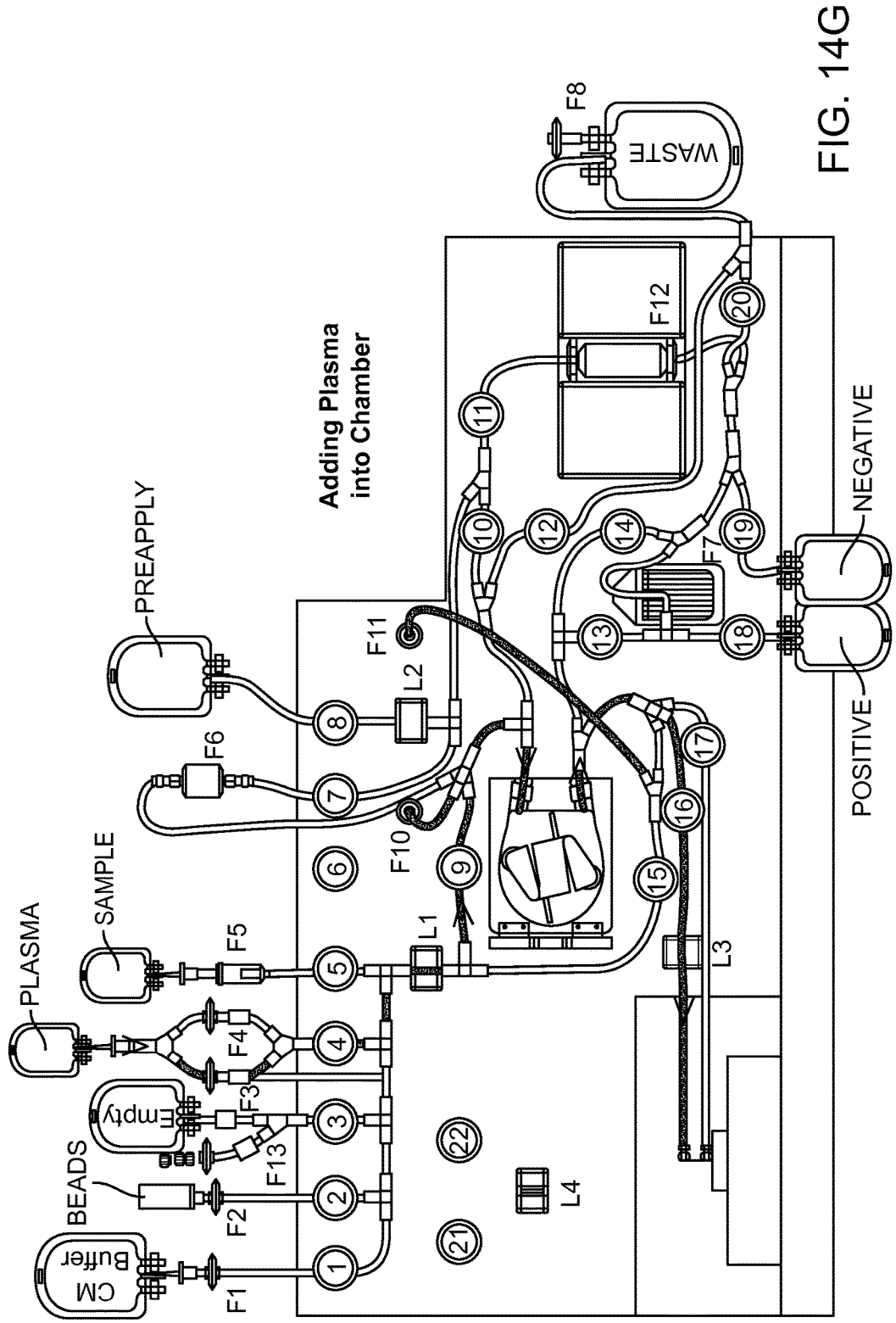
Figure 14H:
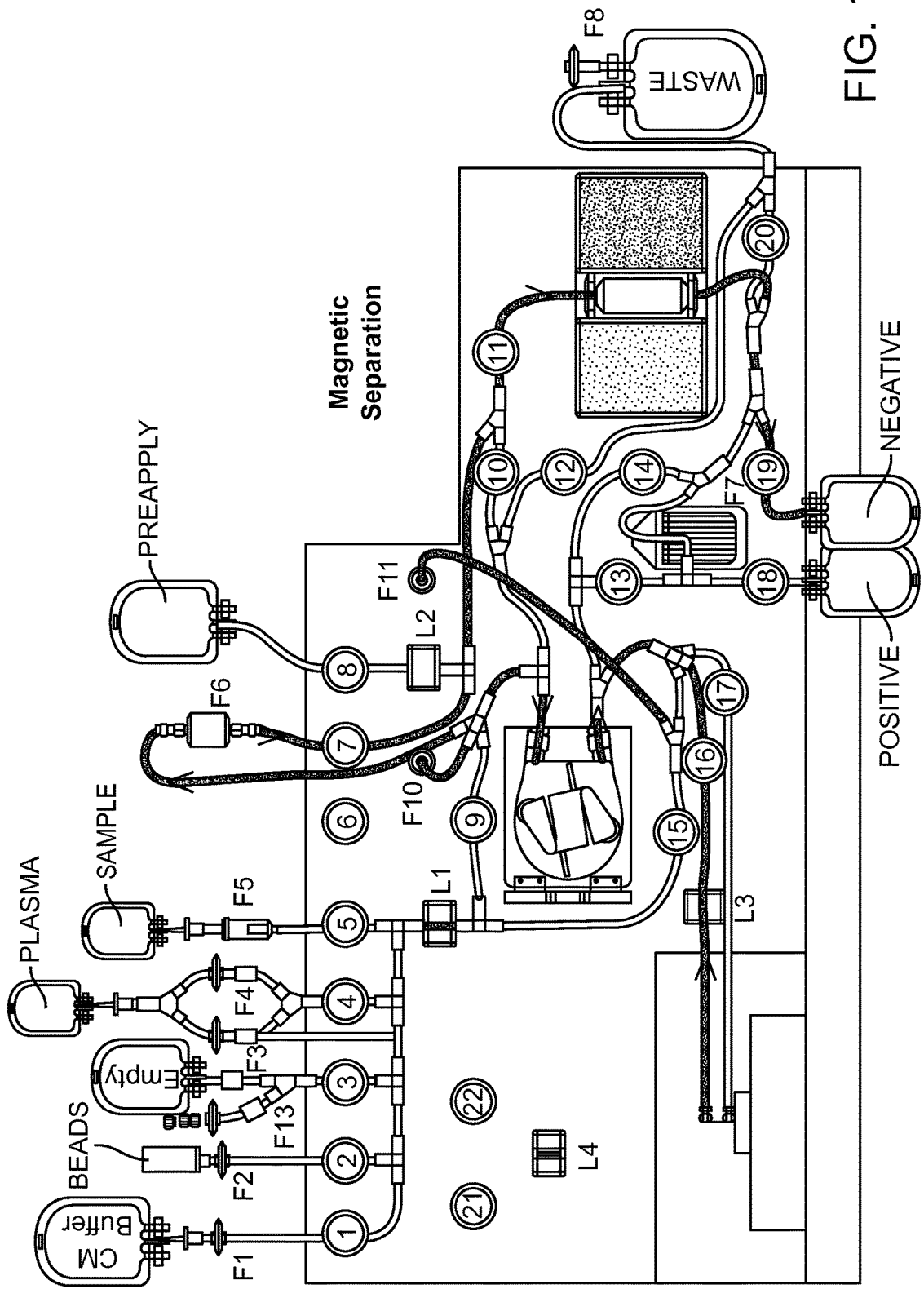
Figure 14I:
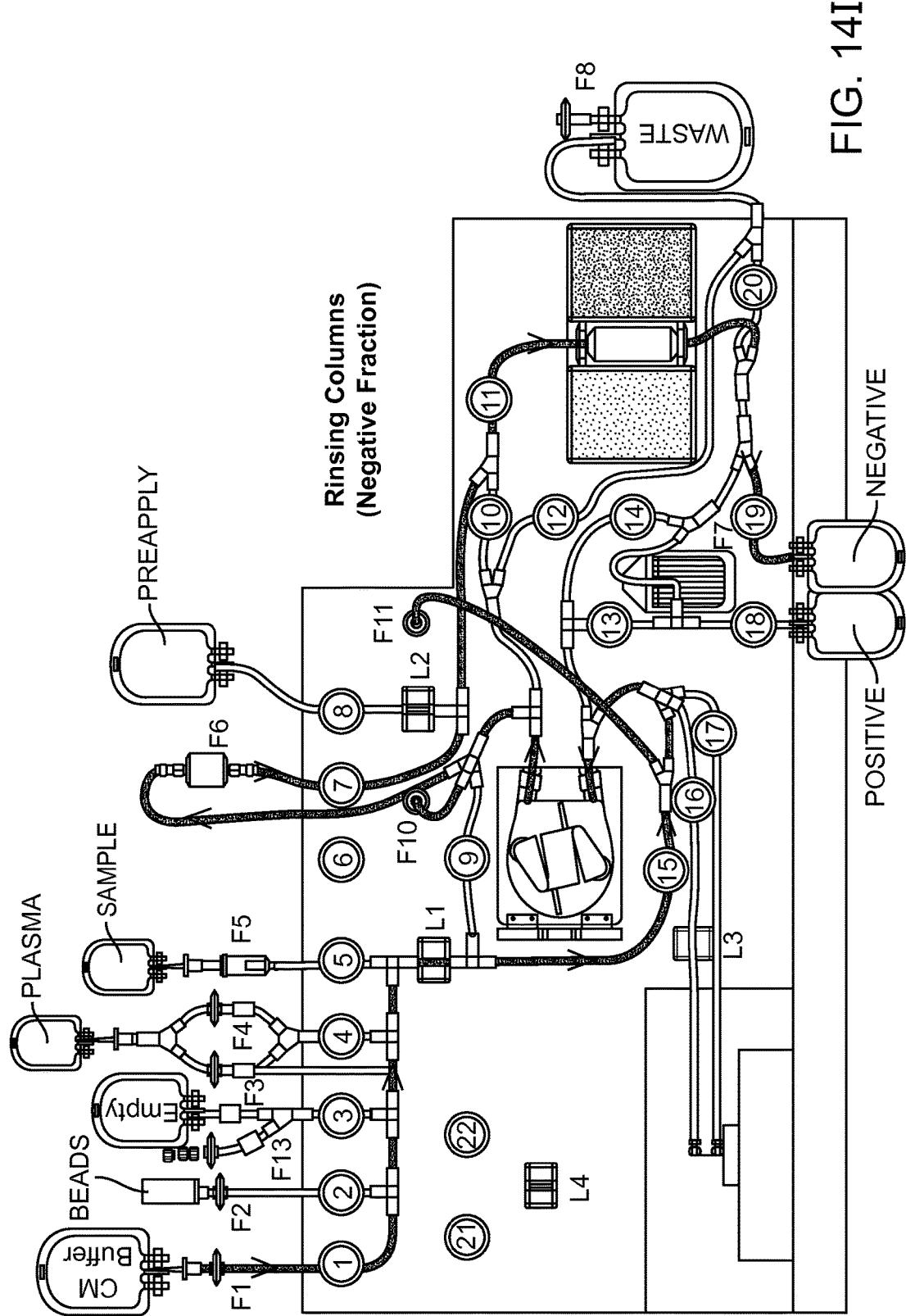
Figure 14J:
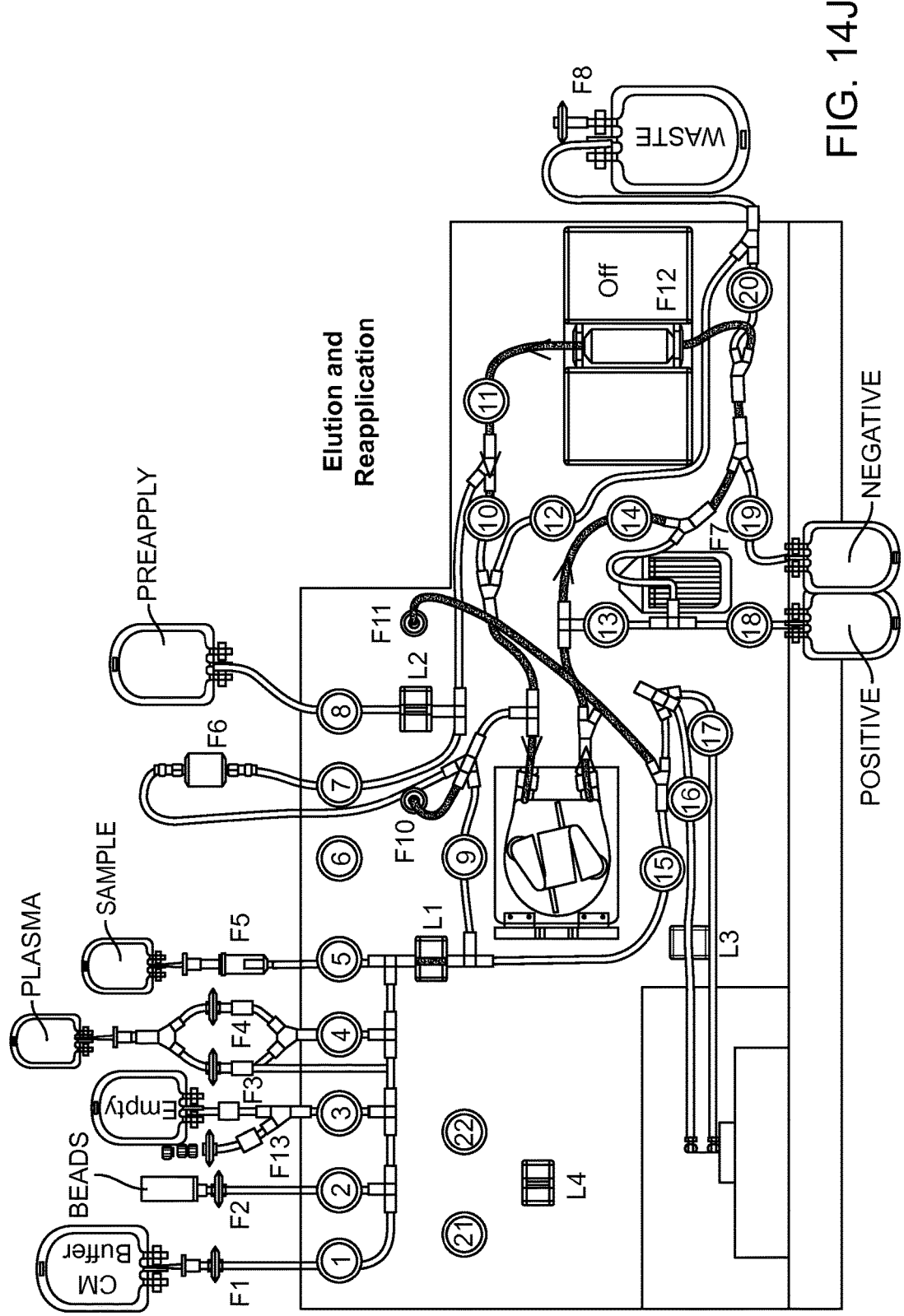
Figure 14K:
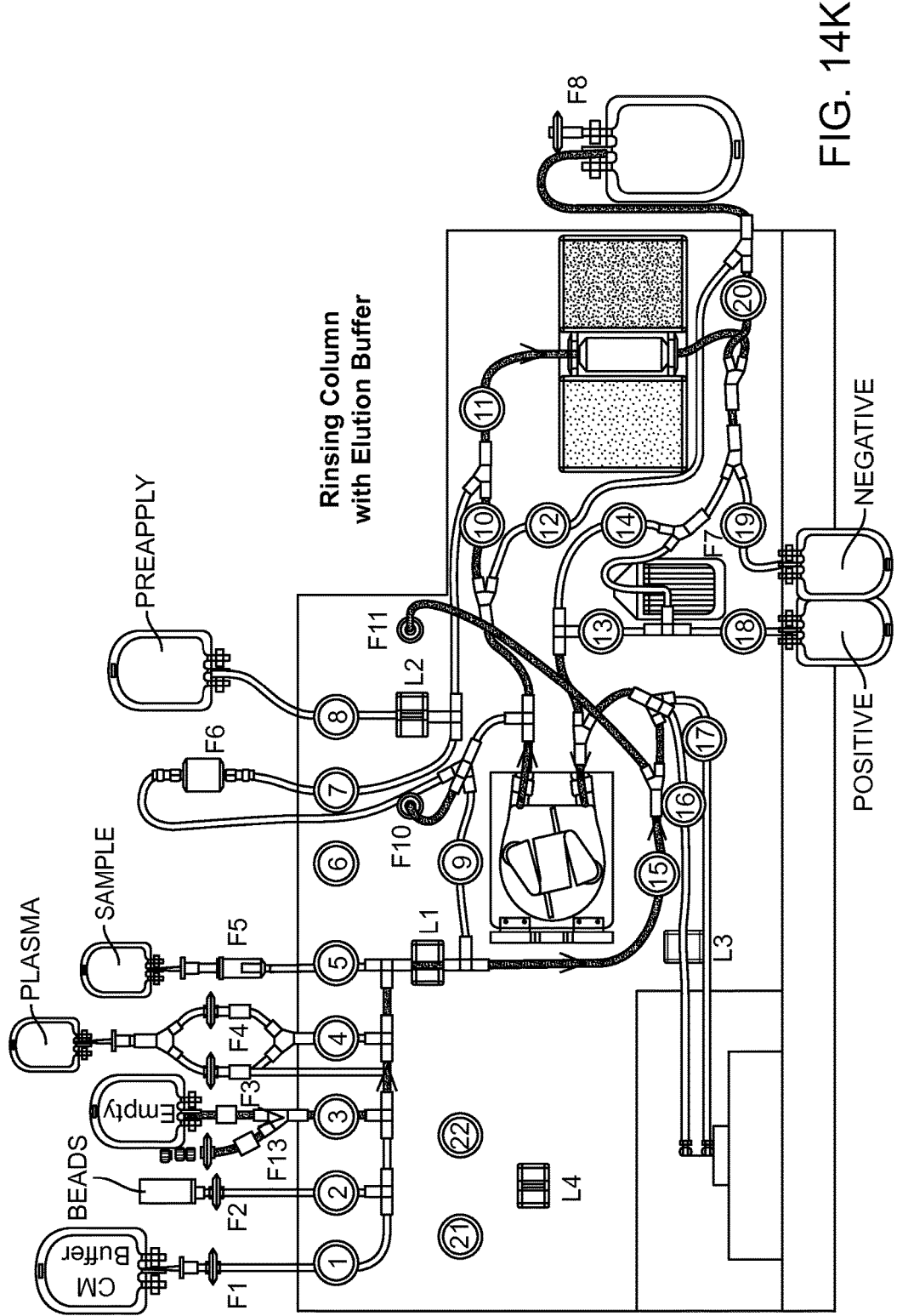
Figure 14L:
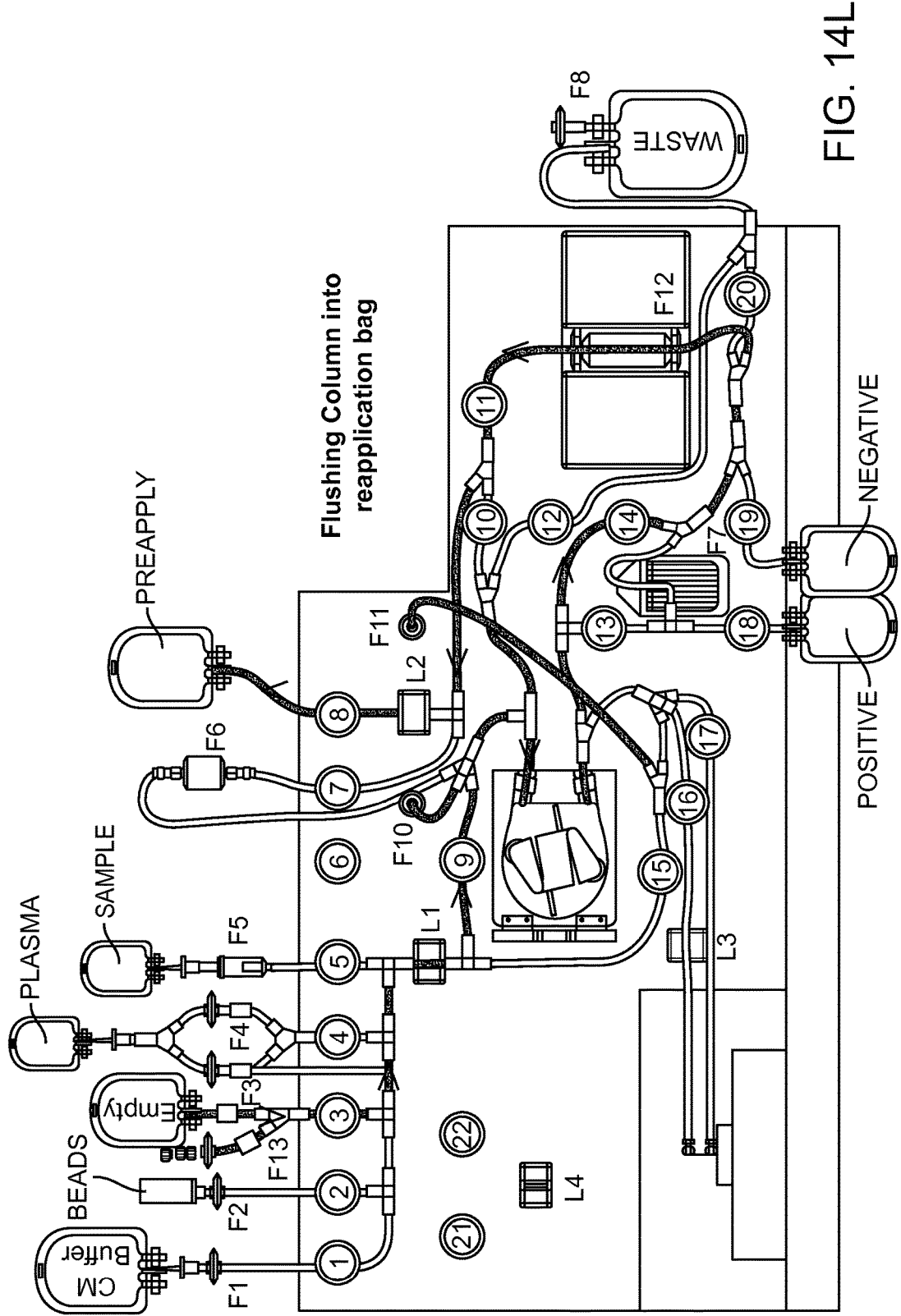
Figure 14M:
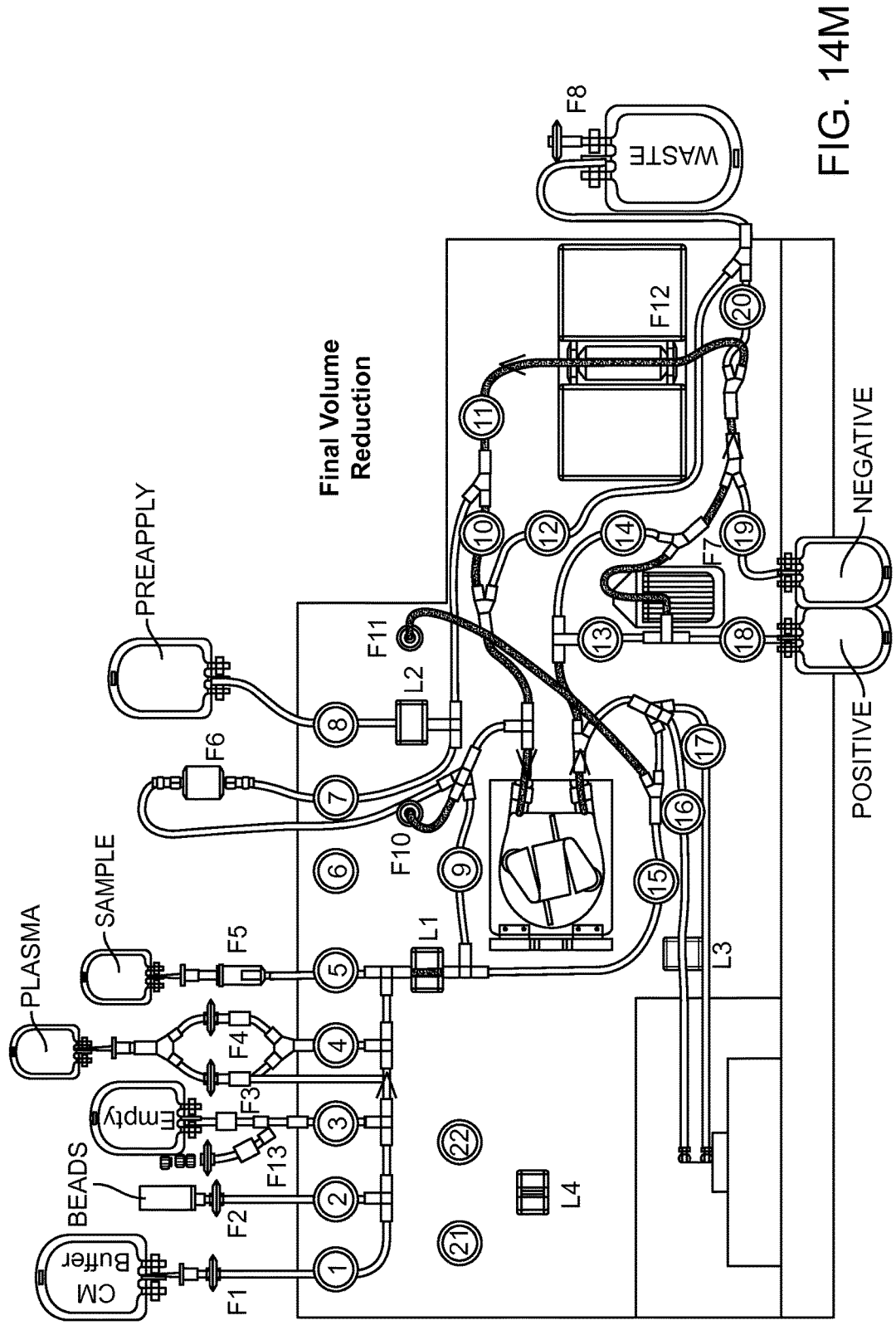
Figure 14N:
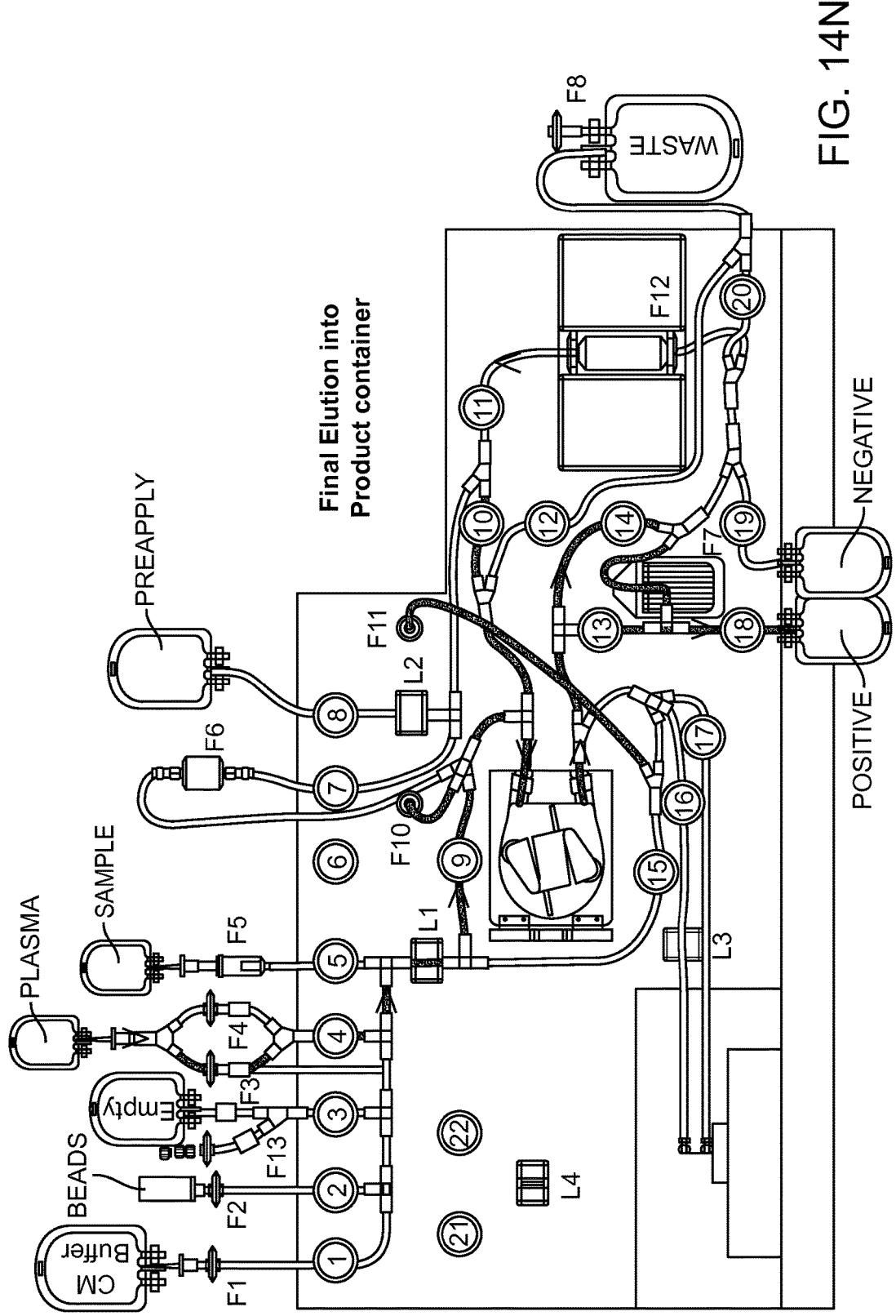

A typical use of a system as illustrated in FIG. 13 and described above, is discussed with reference to FIGS. 14A through 14N. Activation of various components of the system can be selected to direct flow along a desired path. Selected flow is illustrated with reference to FIGS. 14A through 14N and shown by darkened flow paths and flow direction arrows. FIG. 14A illustrates sample loading into a rotating/processing chamber of the sample processing unit. Sample flows from the sample source through open valves 5, 9, 16 and through the pump and into the processing unit. FIG. 14B illustrate rinsing of lines/components of the system, with buffer flowing through open valves 1, 9, 16, pump, and into the processing unit. Sample and buffer can be flowed as illustrated, sample in the processing unit centrifuged for separation of components, and the rinsing process repeated. FIG. 14C illustrates red blood cell reduction and removal from the sample. As stated above, sample in the processing unit can be centrifuged for separation of components, including formation of a buffy coat for separation of red blood cells. Red blood cell component can then be removed from the processing unit and flowed through the system through open valves 17, 12 and into the waste container. FIG. 14D illustrates removal of plasma from the chamber in the processing unit, where plasma rinse/component is flowed through the system through open valves 16, 12 and into the waste container. FIG. 14E illustrates collection of plasma as plasma is removed from the processing unit, flowed through the system at open valves 16, 9, 4 and into a plasma collection container. FIG. 14F illustrates loading of reagent into the chamber and labeling of cells. Reagent (e.g., magnetic label) is flowed through the system at open valves 2, 9, 16 and into the chamber. Cells can be processed (e.g., agitated, reconstituted, mixed with reagent, etc.) for incubation with label reagent. FIG. 14G illustrates addition of plasma into the chamber. Plasma from the plasma container is flowed through the system through open valves 4, 9, 16 and into the chamber. Additional processing, rinsing, etc. steps (e.g., as illustrated in FIG. 14B) can be preformed. FIG. 14H illustrates magnetic based separation of labeled and unlabeled components of the sample. Sample/resuspended labeled cells are flowed through the system through open valves 16, through a filter or (pre-)column (e.g., size based separation filter so as to remove clumped cells), open valves 7, 11, through the magnetic column where labeled cells are bound, with primarily unlabeled cells flowing through open valve 19 and into negative/unlabeled cell container. FIG. 14I illustrates column rinsing where buffer is flowed through the system at open valves 1, 15, 7, 11, 19 and into the cell container. Rinsing steps are selected to wash unlabeled cells from the system/magnetic separation column. FIG. 14J illustrates elution of cells from the column and reapplication. Magnetic application is turned off and fluid flowed as illustrated through open valves 11, 10, 14, e.g., at high speeds, so as to wash cells from the column. The magnetic field application is then turned back on for reattachment of labeled cells to the magnetic separation column. FIG. 14K illustrates rinsing of the column with an elution buffer. Buffer is flowed as illustrated so as to preferentially wash unlabeled cells from the separation column and into the waste container. FIG. 14L illustrates flushing of the column so as to remove labeled cells from the column and into the reapplication bag. As shown, the magnetic field is turned off to free labeled cells from the column. FIG. 14M illustrates volume reduction steps. Solution containing cells is flowed as illustrated so as to pass the solution through the filter F7. The filter includes a membrane filter that collects cells as solution flows through. FIG. 14N illustrates final elution and collection of the product into the collection container. Plasma is flowed as illustrated through open valves 4, 9, 14, 18, with fluid passing through filter F7 so as to wash cells from the filter and into the positive collection container.

The tubing set of the present invention can be used for delivery of nutrient medium, cytokines, growth factors, serum and other substances necessary for the cultivation of the cells, or for taking out samples from the cultivation chamber. Nutrient medium can be continually or periodically delivered into the chamber or withdrawn from the chamber through the ports 222 and 224 (FIG. 11) by using the pump 328 (FIG. 13) or by using additional syringes connected to the tubing set. The medium can be completely or partially exchanged with fresh medium during the cell cultivation process. The medium can be enriched with $O_2$, $CO_2$, $N_2$, air or other gases necessary for the growth of the cells. The medium enrichment can be done by direct injection of the gases into the cultivating chamber through the ports 222 or 224 (FIG. 11), through an additional opening at the bottom of the cultivation chamber covered with a hydrophobic membrane (FIGS. 12A and 12B) and/or by using an aeration device, positioned outside the cultivation chamber (FIG. 15).

Figure 15:
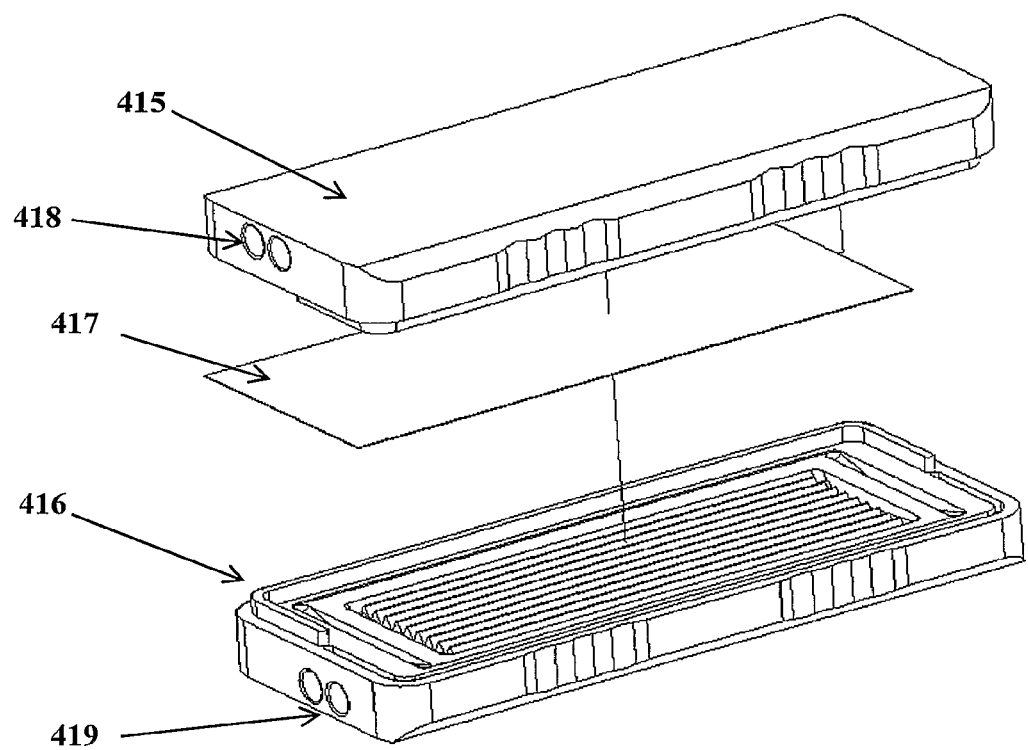
FIG. 15 illustrates an aeration device that can be part of the system according to the invention.

An example of such an aeration device is depicted in FIG. 15. It consists of two parts (415 and 416) made of, for instance, polycarbonate (PC) or polymethymetacrylate (PMMA) with engraved channels on one side. Both parts are brought together forming a hollow space in between, separated in two or more compartments by at least one membrane (417). The membrane can be bonded to one of the parts or several membranes can be bonded on both parts. The compartments contain at least one inlet (418) and one outlet (419) port for connection with the tubing set. The first compartment is used for the gas-mixture. The second compartment is used for the nutrient medium, which has to be enriched with the components of the gas-mixture. The membrane positioned between both compartments is permeable for gases and not permeable for liquids. Preferentially, this is one hydrophobic membrane, for instance nylon hydrophobic membrane. Preferentially, the pores of the hydrophobic membrane are smaller then 0.2 µm, which assures a sterile connection between the nutrient medium and the gas-mixture. In another embodiment of the aeration device, one or more additional membranes can be bonded to either of the parts depicted in FIG. 15, in a way that the gas flows between the medium containing compartments. In this case, the contact surface between the medium and the gas-mixture is larger by multitudes depending on the number of membranes used.

The membranes in the aeration device can be bonded to the parts by means of thermal bonding, ultrasonic bonding or gluing, or other suitable bonding process, which allows a sterile connection between the plastic parts and the membrane.

The aeration device can be sterilized by means of irradiation, (e.g. gamma-, beta-radiation), plasma- (e.g. hydrogen peroxide), hot vapor/steam (e.g. autoclaving) or ethylene oxide (EtO) sterilization. Preferentially the aeration device is used as a part of the disposable tubing set.

Figure 16:
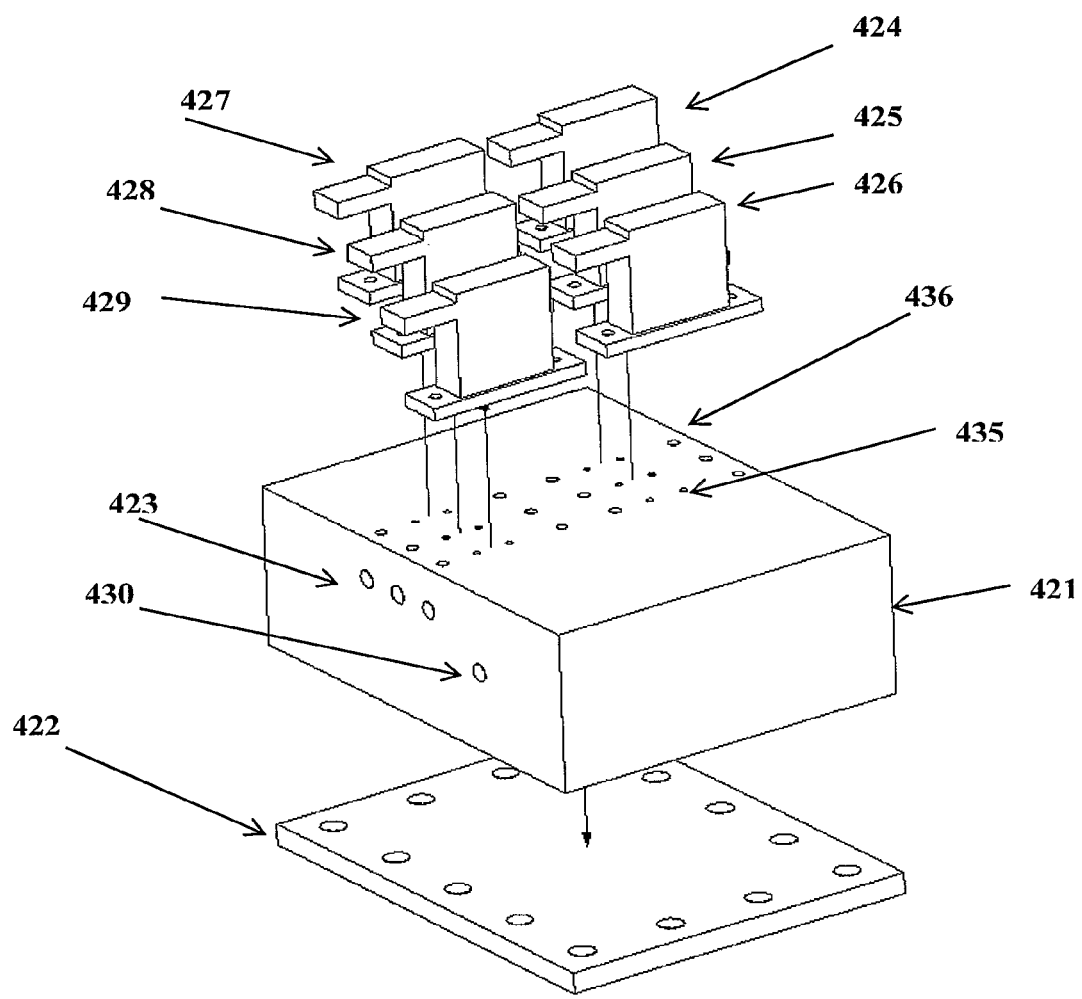
FIG. 16A shows a gas-mixing chamber that can be part of the system according to the invention.
FIG. 16B shows the bottom part of the gas-mixing chamber that can be part of the system according to the invention.
Figure 16:
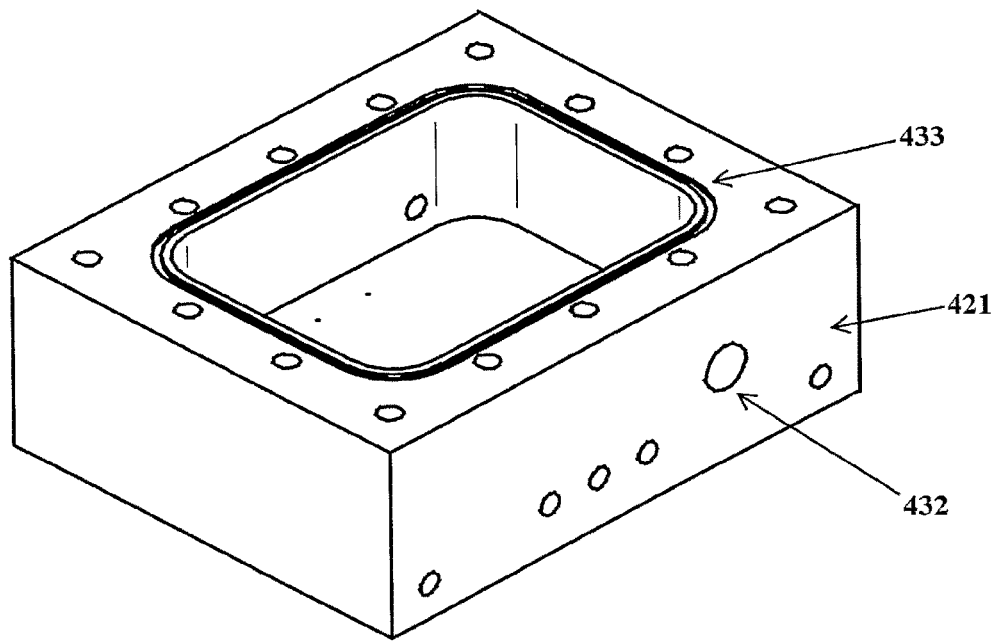

The gas-composition used for the aeration device is preferentially composed through use of a gas-mixing chamber. A preferred embodiment of the gas-mixing chamber is shown in FIG. 16 A. It consists of two parts (421 and 422), preferably made of plastic material, for instance POM (Polyoxymethylene), which are connected with bolts, glued, thermally or ultrasonic bonded together in a way to form a hollow space between them. Preferentially, one of the parts contains a channel for a sealing ring, which assures the sealing between both parts (433, FIG. 16B). The gas-mixing chamber possesses at least one inlet port and at least one outlet port (423). It comprises a port (430) for connection of a pressure sensor device for measurement of the pressure inside the chamber. The gas-mixing chamber optionally contains another port (432, FIG. 16b) for connection with a safety valve, which opens automatically, when the pressure in the chamber rises over a certain value. The gas-mixing chamber possesses inlets and outlets (435) for connection with at least one inlet and at least one outlet valve, as well as drillings with threads (436) for connection of the inlet and outlet valves to the walls of the gas-mixing chamber.

For reduction of the flow rates of the gasses into and/or out of the gas-mixing chamber, blends can optionally be included in the walls.

Principle of operation of the gas-mixing chamber: the inlet ports of the gas-mixing chamber are connected with a gas supply. The supply of the inlet gasses should have pressure of more than the atmospheric pressure, e.g. 2 bar. The operator must give the content of the desired gas composition by using a measurement and automation software program. The content of each of the gases of the desired composition is given as the partial pressure of that gas in the gas mixture. The gas composition process starts with the first component of the gas-mixture, which is controlled by the input valve 424 (FIG. 16A). The input valve opens for a period of time, usually between 50 ms and 200 ms, and then closes and the pressure sensor is read out. The measured pressure in the chamber is $P_m$. If the pressure $P_m < P_1$, where $P_1$ is the pressure given by the operator, the input valve opens again. The process is repeated until $P_m >= P_1$. Then input valve 425 opens and the composition of the second gas component takes place as described in the case with input valve 424. When all input gases are composed into the mixing chamber, the output valve 427 opens until the pressure in the gas-mixing chamber reaches a value $P_{out}$, preliminary given by the operator. $P_{out}$ is always either equal to the atmospheric pressure or higher. The time and the frequency of the opening of the outlet valve can be given by the operator as well. Then the gas-composition process starts again with the opening of the first inlet valve (424). Outlet valves 428 and 429 can be optionally used for aeration of another cell culture chambers, bags or other vessels used in the present invention.

The sample chamber allows a large range of cell culture methods to be performed, such as growing of cells, separating, washing, enriching the cells or different kinds of cells, or others. The system of the invention can also be used to formulate drugs.

Manufacturing of cell preparations required for cellular therapy can include various combinations of basic operations to obtain a defined cell product with defined characteristics. It is unique to the invention that all these basic operations can be performed in a single, closed tubing set, eliminating the risks of otherwise required manual sample transfer steps.

Cell culture conditions for the examples are known in the art.

The features described herein may be of relevance for the realization of the present invention in any combination.

EXAMPLES

The following examples are provided to illustrate, but not limit the invention.

Example 1

Manufacturing of Stem Cell and Progenitor Grafts from Cord Blood

Human cord blood is diluted with CliniMACS PBS/EDTA Buffer, adjusted to the defined labeling volume by centrifugation, CliniMACS CD34 or CD133 Reagent is added and allowed to incubate with the cell sample for the specified labeling time, access reagent is removed by washing in the centrifuge chamber, CD34 or CD133 positive cells are enriched from the cell suspension and eluted from the MACS column directly with cell culture medium and transferred into the cell culture chamber. Media supplements (human serum albumin, cytokines) are automatically added from the vial attached to the tubing set. Enriched or isolated stem cells are cultivated for up to three weeks. Supplemented cell culture medium is intermittently added. Expanded cord blood cells are washed by centrifugation to remove cell culture medium and cells are resuspended in infusion solution (saline) supplemented with human serum albumin and transferred to the final product container (infusion bag or syringe).

Example 2

Manufacturing of a Dendritic Cell Vaccine

Human whole blood or apheresis harvest is diluted with CliniMACS PBS/EDTA Buffer, adjusted to the defined labeling volume by centrifugation, CliniMACS CD14 Reagent is added and allowed to incubate with the cell sample for the specified labeling time, access reagent is removed by washing in the centrifuge chamber, CD14 positive monocytes are enriched from the cell suspension and eluted from the MACS column directly with cell culture medium and transferred into the cell culture chamber. Media supplements (human serum albumin, cytokines) are automatically added from the vial attached to the tubing set. Enriched or isolated monocytes are cultivated into immature monocyte-derived dendritic cells. Media is exchanged by centrifugation and additional supplements are automatically added from the vial attached to the tubing set. Cells are cultivated and upon maturation antigens (recombinant protein, peptides, cell lysates, DNA) are automatically added from the vial attached to the tubing set. Monocyte derived dendritic cells are cultivated for antigen processing. Cell culture medium is removed by centrifugation and cells are resuspended in infusion solution (saline) supplemented with human serum albumine and transferred to the final product container (infusion bag or syringe).

Example 3

Manufacturing of a mDC and pDC Blood Dendritic Cell Vaccine

Apheresis harvest is diluted with CliniMACS PBS/EDTA Buffer automatically depleted of CD19 and subsequently enriched for CD304 (BDCA-4, CD1c, Neuropilin-1) or CD1c (BDCA-1) via the MACS column. DCs are eluted from the MACS column directly with cell culture medium and transferred into the cell culture chamber. Media supplements (human serum albumin, cytokines, activating components like recombinant protein, peptides, cell lysates, DNA) are automatically added from the vial attached to the tubing set and the cells are cultured for 24 h to achieve an optimal maturation and activation. Cell culture medium is removed by centrifugation and cells are resuspended in infusion solution (saline) optionally supplemented with human serum albumine and transferred to the final product container (infusion bag or syringe). The product container is removed from the tubing set of the invention for further user.

Example 4

Manufacturing of Antigen Specific T Cells

Human whole blood or apheresis harvest is washed and diluted with cell culture medium and transferred into the cell culture chamber. Antigen (recombinant protein, peptide pool or tumor cell lysate) and media supplements (human serum albumin, cytokines) are automatically added from the vials attached to the tubing set. Cells and antigen are cultivated for 3-16 hours to re-stimulate antigen specific T cells. Cell suspension is adjusted to the defined labeling volume by centrifugation, CliniMACS IFN-gamma Catchmatrix Reagent is added and allowed to incubate with the cell sample for the specified labeling time, and access reagent is removed by washing in the centrifuge chamber. Cells are transferred into the cell culture container and incubated for release of cytokines. Cell suspension is adjusted to the defined labeling volume by centrifugation, CliniMACS IFN-gamma Enrichment Reagent is added and allowed to incubate with the cell sample for the specified labeling time, access reagent is removed by washing in the centrifuge chamber, antigen specific cells are magnetically enriched from the cell suspension, and concentrated to a small, injectable volume by direct elution from the MACS column using supplemented infusion solution and transferred to the final product container (infusion bag or syringe).

Example 5

Manufacturing of a Activated Natural Killer Cells

Human whole blood or apheresis harvest is diluted with CliniMACS PBS/EDTA Buffer, adjusted to the defined labeling volume by centrifugation, CliniMACS CD3 Reagent is added and allowed to incubate with the cell sample for the specified labeling time, access reagent is removed by washing in the centrifuge chamber, CD3 positive cells are depleted from the cell suspension. CD3 negative target cells are adjusted to the labeling volume, CliniMACS CD56 Reagent is added and allowed to incubate with the cell sample for the specified labeling time, access reagent is removed by washing in the centrifuge chamber, CD56 positive cells are enriched and eluted from the MACS column directly with cell culture medium and transferred into the cell culture chamber. Media supplements (human serum albumin, cytokines such as IL-2 and/or IL-15) are automatically added from the vial attached to the tubing set. Enriched or isolated NK cells are cultured for 8-48 hours. Cell culture medium is removed from the cell product by centrifugation and cells are resuspended in infusion solution (saline) supplemented with human serum albumin and transferred to the final product container (infusion bag or syringe).

Example 6

Manufacturing of Expanded Natural Killer Cells

Human whole blood or apheresis harvest is diluted with CliniMACS PBS/EDTA Buffer, adjusted to the defined labeling volume by centrifugation, CliniMACS CD3 Reagent is added and allowed to incubate with the cell sample for the specified labeling time, access reagent is removed by washing in the centrifuge chamber, CD3 positive cells are depleted from the cell suspension. CD3 negative target cells are adjusted to the labeling volume, CliniMACS CD56 Reagent is added and allowed to incubate with the cell sample for the specified labeling time, access reagent is removed by washing in the centrifuge chamber, CD56 positive cells are enriched and eluted from the MACS column directly with cell culture medium and transferred into the cell culture chamber. Media supplements (human serum albumin, cytokines) are automatically added from the vial attached to the tubing set. Cell Expansion Beads loaded with antibodies directed against CD2 and CD335 (NKp46) or CD314 (NKG2D) and CD335 (NKp46) are transferred from the vial to the cell culture compartment. Enriched or isolated NK cells are cultured for one weak, starting at day 7, supplemented cell culture medium is added every 3 days in a 1:1 ratio and cells are cultivated until day 14-21.

Expanded NK cells are passed over the MACS column to remove cell expansion beads. Optionally expanded NK cells are further purified by CD3 depletion or CD56 enrichment (see above). Cell culture medium is removed from the cell product by centrifugation and cells are resuspended in infusion solution (saline) supplemented with human serum albumine and transferred to the final product container (infusion bag or syringe).

Example 7

Manufacturing of a Expanded T Helper Cells

Human whole blood or apheresis harvest is diluted with CliniMACS PBS/EDTA Buffer, adjusted to the defined labeling volume by centrifugation, CliniMACS CD4 Reagent is added and allowed to incubate with the cell sample for the specified labeling time, access reagent is removed by washing in the centrifuge chamber, CD4 positive cells are enriched and eluted from the MACS column directly with cell culture medium and transferred into the cell culture chamber. Media supplements (human serum albumin, cytokines) are automatically added from the vial attached to the tubing set. Cell Expansion Beads loaded with antibodies directed against CD2, CD3 and CD28 or alternatively CD3 and CD28 are transferred from the vial to the cell culture compartment. Isolated T helper cells are cultured, starting at day 3, supplemented cell culture medium is added every 2 days in a 1:1 ratio and cells are cultivated until day 14. Expanded T cells are passed over the MACS column to remove cell expansion beads. Cell culture medium is removed from the cell product by centrifugation and cells are resuspended in infusion solution (saline) optionally supplemented with human serum albumine and transferred to the final product container (infusion bag or syringe). The product container is removed from the tubing set of the invention for further user.

Example 10

Selection of CD133 Positive Stem Cells

The CD133 antigen is a stem cell marker and is specifically expressed on an immature subset of CD34$^+$ cells, on circulating endothelial progenitor cells and on a CD34$^-$ stem cell subset (De Wynter et al., 1998). Enriched or isolated CD133 positive cells using the CliniMACS CD133 System have been used for ex vivo expansion of hematopoietic progenitor cells form cord blood, and in autologous (Pasino et al., 2000) and allogeneic (Köhl et al., 2002) transplantation.

CD133$^+$ stem cells can be utilized in non-hematological applications for regenerative medicine. CD133 selected cells from bone marrow have come into focus for example regarding the treatment of ischemic heart diseases (Stamm et al., 2003).

Enrichment or isolation of CD133+ cells results in a removal of non target cells of more than 99.4% (2.2 log). See table 1.

TABLE 1

CD133 positive cells have been isolated from bone marrow using the present invention:

| Start volume [ml] | Starting frequency CD133+ | Final purity CD133+ | CD133$^-$ log depletion | Final cell number CD133+ | CD133$^+$ yield* |
|---|---|---|---|---|---|
| 17 | 0.51% | 56.54% | 2.2 | 5.5E5 | 60.89%* |
| 42 | 0.26% | 51.15% | 2.5 | 1.3E6 | 87.32%* |
| 53 | 0.62% | 66.16% | 2.7 | 2.5E6 | 56.65% |
| 34 | 0.26% | 48.89% | 2.3 | 8.4E5 | 77.96%* |
| 62 | 0.55% | 60.51% | 2.7 | 1.8E6 | 54.04% |

(*calculated in relation to CD133$^+$ cells recovered in all bags)

For comparison, all bone marrow products have also been processed using the CliniMACS® CD133 System with similar results.

Figure 20:
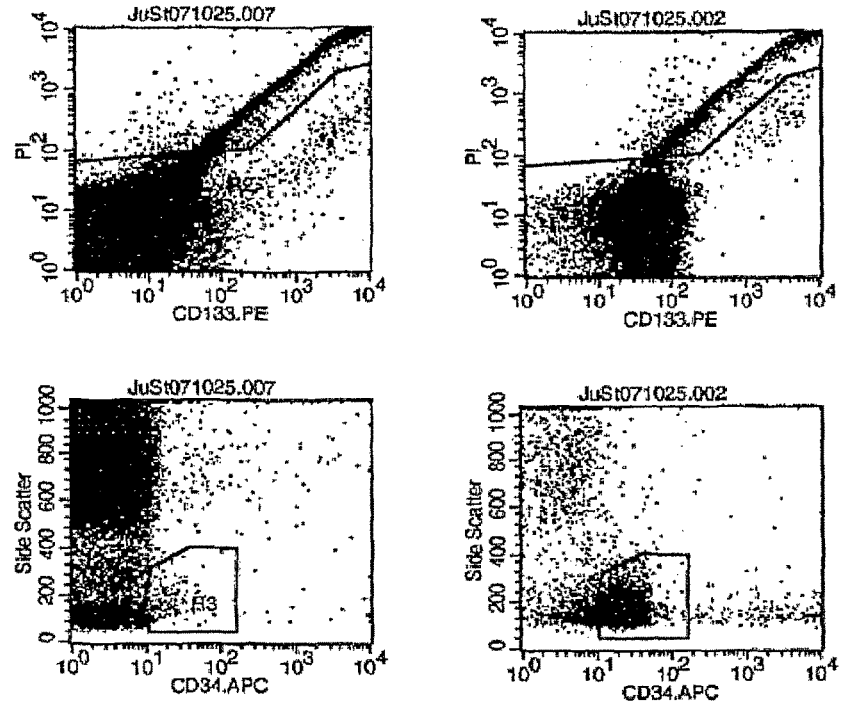
FIGS. 20 to 29 show the results of experiments performed with a system according to the present invention, using a method according to the present invention.

The dotplots in FIG. 20 show sample characteristics before (left) and after (right) automated processing using the present invention.

Example 11

Selection of CD14 Positive Cells

The CD14 antigen belongs to the LPS receptor complex and monocytes strongly express the antigen. CD14 selected monocytes can be used for subsequent generation of human monocyte-derived dendritic cells (MoDCs; Campbell et al., 2005). Dendritic Cells have great potential as cellular vaccines for various diseases, including solid tumors, hematological malignancies, viral infections and autoimmune diseases.

Figure 21:
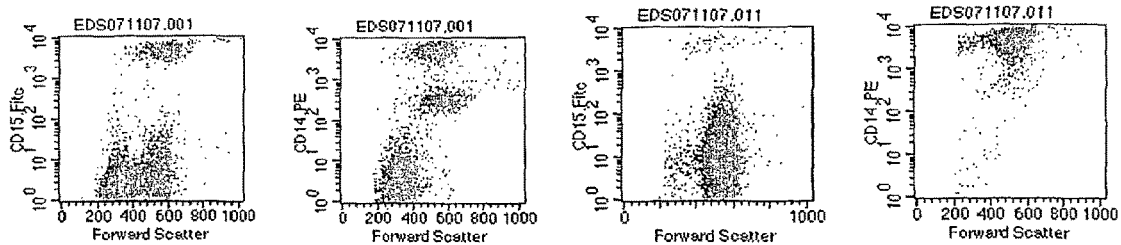
Figure 22:
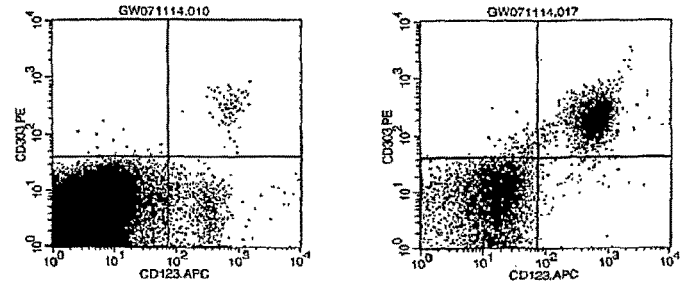
Figure 23:
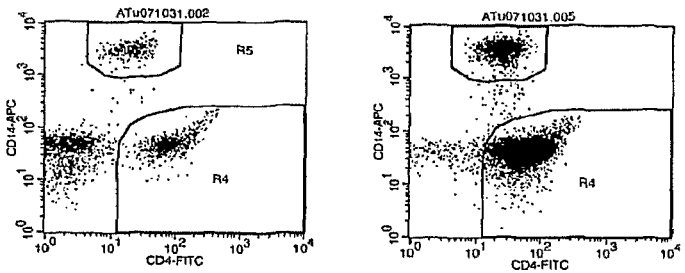
Figure 24:
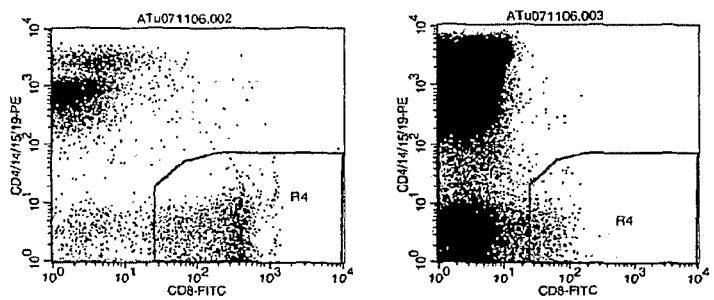
Figure 25:
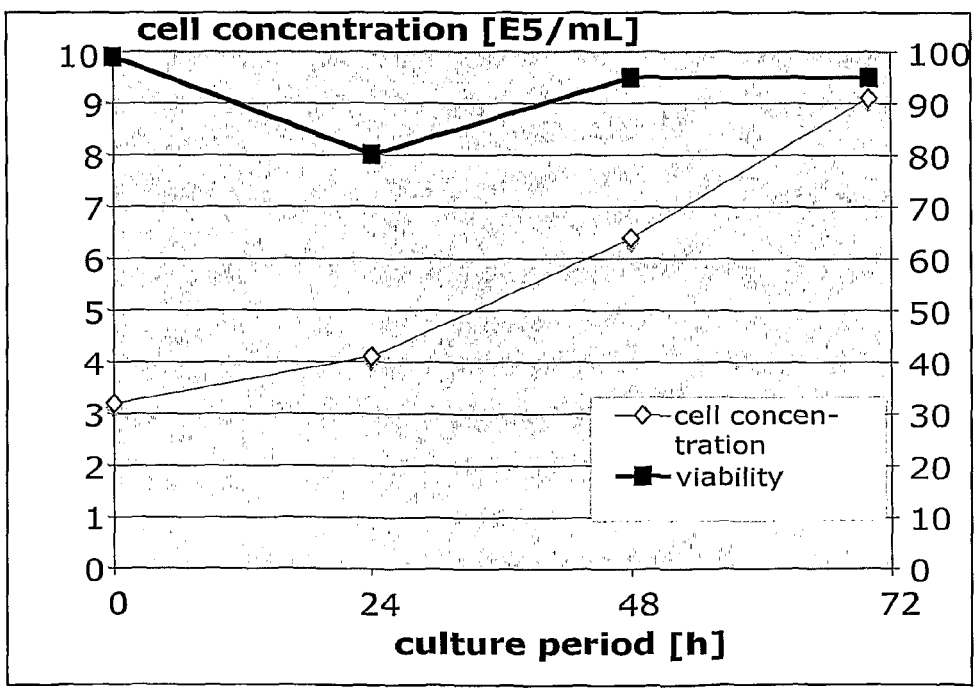

Monocytes have been isolated from two leukapheresis harvests using the present invention and the CliniMACS CD14 Reagent. Monocytes were enriched from 19.7%/31.8% (unprocessed harvest) to 98.2%/99.7% (final cell product) with a yield of 58%/21% (see FIG. 21)

MoDC could be generated from monocytes isolated using the present invention and showed identical characteristics to MoDCs generated from CliniMACS isolated monocytes.

Monocytes were also isolated from buffy coat from human whole blood using the present invention and could be enriched from 9.8% (unprocessed buffy coat) to 98.9% purity (final cell product) with a monocyte yield of 64%.

Example 12

CD304 Selection

In peripheral blood CD304 (BDCA-4, Neuropilin-1) is expressed on human plasmacytoid dendritic cells (PDCs). PDCs are the most potent Type I Interferon-producing cells (Dzionek et al., 2002). CD304 can be used to directly enrich or isolate dendritic cells from peripheral blood without a culturing period (as for MoDCs).

Enrichment or isolation of CD304 positive target cells requires extended washing steps which are time-consuming utilizing the CliniMACS sample preparation procedure in a blood bag centrifuge. Automated sample processing will facilitate use of CD304 isolated cells in vaccination trials.

CD304 positive cells were isolated or enriched from two leukapheresis harvest utilizing the present invention and CliniMACS CD304 Reagent. PDCs were enriched from 0.29% to 34.4% with a yield of 30% and from 0.43% to 80.5% with a yield of 39%.

Plasmacytoid Dendritic Cells from the second procedure were cultivated for 24 h with CPG C (ODN2395) and IL-3 or IL-3 alone for maturation induction. Cultivated cells were analyzed for maturation markers CD40 and CD80 and marker profile was identical to isolated CD304 positive PDCs using the CliniMACS CD304 System upon cultivation.

Example 13

Selection of CD4 Positive Cells

CD4 is an accessory molecule in the recognition of foreign antigens in association with MHC class II antigens by T cells. T helper cells and to a lower degree monocytes and dendritic cells express CD4.

For certain oncological settings preliminary data suggest that T cells in a graft or as a donor lymphocyte infusion may be beneficial (Falkenburg et al., 1999). In these settings a CD4 selection or CD8 depletion (see example 5) may be desired in the allogeneic transplantation setting. T helper cells may be capable of mounting anti-tumor responses, reducing the risk of Graft versus Host Disease (Alyea et al. 1998) and reconstituting the recipient's immune system (Bellucci et al., 2002).

CD4 positive T helper cells also play a significant role in HIV infection and progression. Selected T helper cells (potentially after genetic modification) may be desired for treatment of HIV complications.

CD4 positive cells were isolated or enriched from three buffy coat products from human whole blood utilizing the present invention and the CliniMACS CD4 Reagent. T helper cells were enriched from 27%/8.6%/15.9% to 90%/80%/81.3% purity with a yield of 93%/98%/51%. These results are well within the range of results obtained using the CliniMACS CD4 System.

Example 14

Depletion of CD8 Positive Cells

The CD8 antigen, a co-receptor for MHC class I molecules, is expressed on cytotoxic T cells and dimly on a subset of NK cells.

In the allogeneic transplantation setting CD8 T cells may be removed from a graft or donor lymphocyte infusion with the goal of preventing Graft versus Host Disease while maintaining Graft versus Leukemia effects Meyer et al. 2007).

CD8 positive cytotoxic T cells were depleted from three huffy coat products utilizing the present invention and the CliniMACS CD8 reagent. Cytotoxic T cells were depleted from 11.5%/8%/12% to 0.005%/0.004%/0.002% respectively. This represents a >99.97% (>3.5 log) removal of non-target cells. CD8 negative target cells were nearly completely recovered (85.1%/90.9%/94.4%).

Example 15

Preparation of Peripheral Blood Mononuclear Cells by Density Gradient Centrifugation Ficoll-Paque™ is a sterile density medium for the isolation of mononuclear cells from bone marrow, peripheral blood, and cord blood. It is an aqueous solution of density 1.077 g/ml, consisting of Ficoll PM400 (a highly branched, high-mass, hydrophilic polysaccharide), sodium diatrizoate and disodium calcium EDTA. Erythrocytes and granulocytes have a density of more than 1.077 g/ml while lymphocytes and monocytes have a lower density. When human blood is layered on top of the Ficoll-Paque lymphocytes and monocytes can be separated from erythrocytes and granulocytes under centrifugal force.

The present invention has been used for preparation of peripheral blood mononuclear cells by density gradient centrifugation. Buffy coat from human whole blood was layered onto a ring of Ficoll-Paque while the centrifugation chamber was rotating. The rotation speed had been adjusted to 2,900 rounds per minute and maintained for 20 minutes. An outer ring of erythrocytes and granulocytes, a ring of Ficoll-Paque, a ring of target cells (peripheral blood mononuclear cells, i.e. lymphocytes and monocytes) and an inner ring of platelet containing blood plasma and PBS buffer could be detected. The different layers were removed from the centrifugation chamber of the present invention through the luer ports and analyzed for content of different cells. 70% of the PBMC of the original blood product were recovered from the PBMC layer. This cell suspension only contained 1.1% of the original red blood cells. The present invention thus can be used for automated preparation of peripheral blood mononuclear cells (second ring) or platelet rich plasma (inner ring).

Example 16

Cell Culture

The centrifugation chamber of the present invention can be used for culturing of cells, similarly to cell culture flasks or bags. 3.2E5/ml of the human cell line K562 have been applied to a centrifugation chamber in a volume of 30 ml RPMI1640 cell culture medium supplemented with 10% fetal calf serum. The chamber was placed in a $CO_2$ incubator at 5% $CO_2$. Aliquots of the content have been removed from the chamber for cell counting and viability assessment after 24, 48 and 70 hours. Seeded cells expanded to 4.1E5/ml, 6.4E5/ml and 9.2E5/ml viable cells at 80%, 95% and 95% viability.

Example 17

Method for the Separation of CD133+ Cells Using a System of the Present Invention The whole separation procedure of CD133+ cells comprises several steps with following tasks:
1. Priming of the tubing set with buffer
2. Transfer of the bone marrow sample to centrifugation chamber
3. Preparation of the bone marrow sample in the centrifugation chamber.
4. Magnetic separation of CD133+ cells
5. Final volume reduction In the following, several steps will be described in detail.
1. Priming of the Tubing Set with Buffer In a first step the tubing set was primed with PEB (phosphate buffered saline supplemented with 2 mmol/l EDTA; 0.5% HSA).
2. Transfer of the Bone Marrow Sample to Centrifugation Chamber After priming of the tubing set the bone marrow sample was transferred from the sample bag 312 to the centrifugation chamber 332.
3. Preparation of the Bone Marrow Sample in the Centrifugation Chamber.

The sample preparation in the centrifugation chamber includes several steps where supernatant is removed from the chamber. During supernatant removal only cell free supernatant or supernatant with platelets in case of the platelet wash should be transferred. It is the aim to avoid white blood cells (WBCs) and therefore CD133+ cells to be removed along with the supernatant. The sample preparation includes following steps:
    generation of plasma
    reduction of platelets
    incubation with CD133 Microbeads (Miltenyi Biotec, Germany)
    removal of unbound CD133 Microbeads Generation of Plasma:

The plasma generated at the beginning of the sample preparation process serves the following two functions:
1. to act as a blocking reagent that blocks the Fc receptors of monocytes and hinders the Fc part of the CD133 antibodies bound to the microbeads to attach to monocytes. This would lead to a reduced purity of the product of the immunomagnetic separation process by monocytes, and
2. to act as a supplement for the buffer in which the final cell product is suspended. This provides a more physiological environment for the cell product than the used buffer alone. For the generation and collection of plasma, the sample is centrifuged until the majority of cellular components of the material as erythrocytes (RBCs), white blood cells (WBCs) and platelets are pelletized. The cell free supernatant is the transferred to a container (303) that acts as a reservoir For plasma generation, the cell material was centrifuged with 2000 rpm in the centrifugation chamber until all cellular components of the material as WBCs, RBCs and platelets are pelletized. The generation of plasma requires a centrifugation that leads to a supernatant with as low cell concentrations as possible and therefore a nearly complete sedimentation of all cellular blood components. The sedimentation time depends on the sample volume that is determined automatically during the sample transfer into the centrifugation chamber. The sedimentation time for different sample volumes is shown in table 2:

TABLE 2

Sedimentation time for different suspension volumes in the plasma generation process

| Volume interval | Maximum volume | Radius of air/liquid boundary layer | Sedimentation time |
|---|---|---|---|
| ≤100 ml | 100 ml | 5.21 cm | 8.01 min ≈ 8 min |
| 100 ml < V ≤ 125 ml | 125 ml | 4.99 cm | 11.82 min ≈ 12 min |
| 125 ml < V ≤ 150 ml | 150 ml | 4.77 cm | 15.98 min ≈ 16 min |
| 150 ml < V ≤ 175 ml | 175 ml | 4.53 cm | 20.57 min ≈ 21 min |
| 175 ml < V ≤ 200 ml | 200 ml | 4.28 cm | 25.69 min ≈ 26 min |

After centrifugation at 2000 rpm the rotation speed was gently reduced to 1000 rpm with a deceleration rate of 632 rpm/min. Then plasma is removed with a pump speed of 6 ml/min until air was pumped out of the chamber. The cell free supernatant is then transferred to a container that acts as a reservoir. Later, the plasma can be transferred from the container to the site in the process where it is used flow through a filter with 0.2 μm to remove all residual cells that were not removed during centrifugation.

Reduction of Platelets:

As the plasma generation removes the complete supernatant in the chamber, a residual volume of 70 ml is in the chamber. 150 ml PEB are added to dilute the suspension resulting in a total volume of 220 ml. The drum is then accelerated to 2000 rpm and the sedimentation executed for 100 sec in order to pelletize the RBCs and WBCs before the drum was decelerated to 1000 rpm with a deceleration rate of 632 rpm/min. Within this sedimentation time, only a small portion of the platelets reach the pellet when the deceleration of the chamber starts. Then the complete supernatant is removed at a speed of 6 ml/min. Analysis of the sample and the removed supernatant showed an experimental determined platelet removal of 50.8%. The remaining platelets are removed using a Filter (310).

Incubation with CD133 Microbeads

The CD133 microbeads are provided in a glass vials having a septum. In order to assure aseptic conditions, a filter with 0.2 μm pore size (306) is integrated into the branch of the tubing set connected to the vial. The vial is connected to the tubing set by a vented vial adapter (305). When the reagent is pumped to the chamber, the pressure within the part of the tubing set in front of the drum is monitored. When the vial runs empty, air moves to the filter. As the filter is wetted by the reagent, the pores are still filled with liquid when the air moves into the filter. Due to capillary forces the air cannot pass the membrane of the filter. As the pump continues to work, the pressure drop is detected by pressure sensor (329) and the software stops the pump. In this way combined with a rinsing step to remove residual reagent, the reagent is transferred automatically to the cell suspension in the chamber.

After transfer of plasma for blocking purposes the volume is adjusted to the labeling volume of 95 ml and the incubation starts. In the conventional sample preparation process the sample preparation bag has to be put on an orbital shaker and incubated for 30 mm at room temperature. The incubation process with the system of the present invention is realized as follows:
1. The drum is accelerated to a speed of 300 rpm. This makes the liquid move to the wall of the chamber.
2. The centrifugation is carried out for 10 seconds.
3. After that, the drum is stopped. The liquid moves back and has a horizontally aligned surface.
4. The chamber continues to stop for 50 seconds.
5. Steps 1-4 are repeated until the incubation time of 30 mm is elapsed.

This process leads to an efficient mixing of the liquid in the chamber.

Removal of Unbound Anti-CD133 Microbeads:

The beads wash is performed in order to remove the unbound reagent after the labeling and incubation. In the wash process the following steps are repeated for three times:
1. PEB is transferred to the centrifuge to dilute the suspension resulting in a total volume of 230 ml
2. Sedimentation of RBCs and WBCs is carried out at 2000 rpm for 140 seconds
3. The speed of the chamber is reduced from 2000 rpm to 1000 rpm
4. Supernatant is removed completely at a speed of 20 ml/min The beads wash process will consist of three washing steps and at least 97.2% of the unbound reagent is removed.

4. Magnetic Separation of CD133+ Cells

Figure 26:
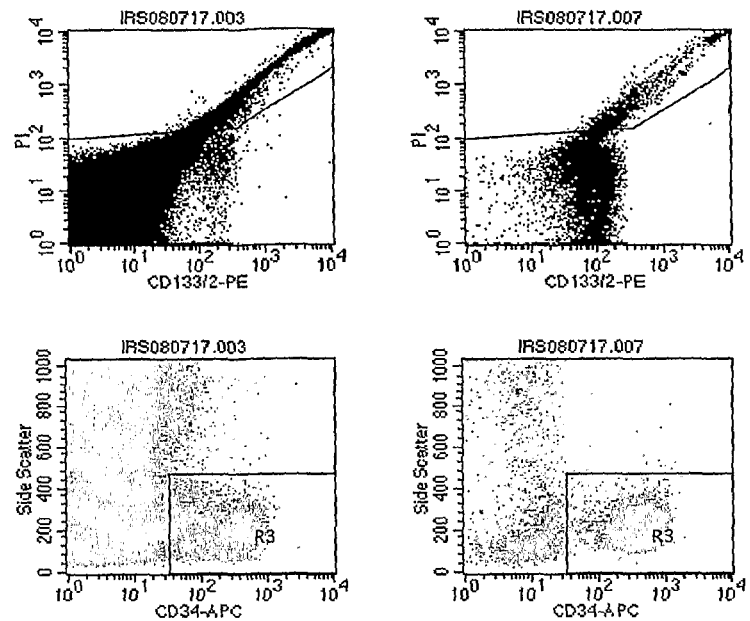

After the beads wash process CD133+ cells are separated using a magnetic separation column (CliniMACS column, Miltenyi Biotec GmbH, Germany). Therefore the cell suspension is transferred on the separation column with a loading rate of 5 ml/min. The magnetically labeled cells are retained in the magnetized column and separated from the unlabeled cells by rinsing of the column with PEB. The retained CD133+ cells are eluted by removing the magnetic field from the column. The CD133+ cells are pumped into a loop of the tubing set and reloaded on the separation column. This process was repeated once again and after the third reloading process, the CD133+ cells are finally eluted in 20 ml elution buffer (see table 3 and FIG. 26). The elution rate is 600 ml/min.

5. Final Volume Reduction

For cardial stem cell therapy, CD133+ cells should be available in a small final volume at most of 6 ml. Normally, CD133+ cells are finally eluted from the CliniMACS column in 20 ml elution buffer. For reducing of the final volume, three methods are possible: The final volume of isolated or enriched CD133+ cells can be reduced by 1. elution from the column in small volume,
2. filtration after magnetic separation, or
3. using the AutoMACS column (Miltenyi Biotec GmbH, Germany).

Figure 27:
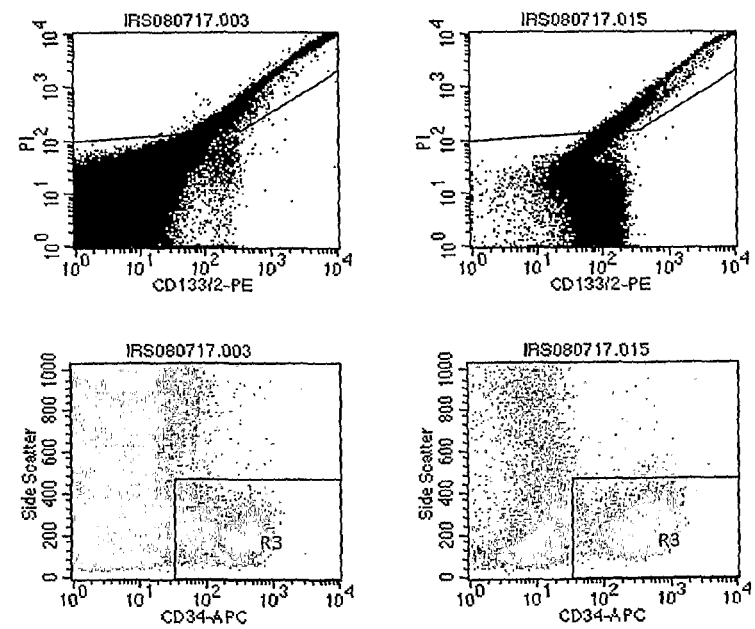

Elution from the Column in Small Volume:

Instead of elution in 20 ml elution buffer, CD133+ cells can be eluted from the CliniMACS column in 6 ml elution buffer. The elution rate is 600 ml/min. This method was tested by the enrichment of CD133+ cells from bone marrow. Enriched cells were determined by FACS analyses (see table 4 and FIG. 27).

Filtration after Magnetic Separation

Figure 28:
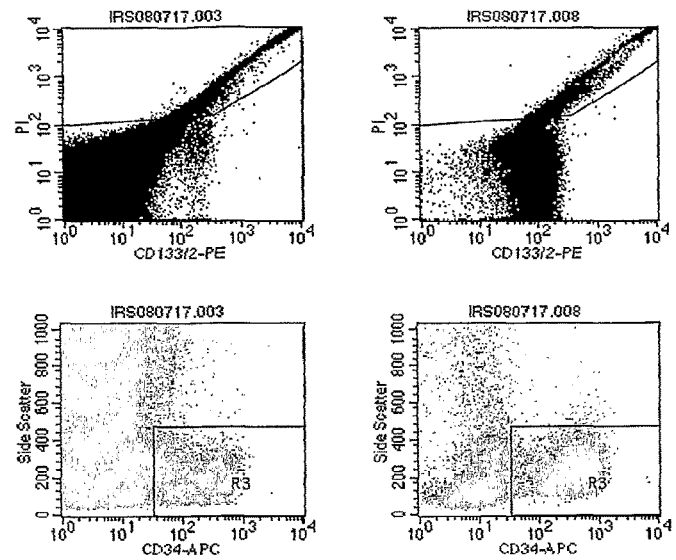

After elution from the CliniMACS separation column in 20 ml elution buffer CD133+ cells can be transferred on a filter (Pall IV-5, 0.2 µm or RoweFil 24, 1.2 µm) at a rate of 4 ml/min. Afterwards the cells are eluted in 2 ml from the filter. This method was tested by the enrichment of CD133+ cells from bone marrow. Enriched cells were determined by FACS analyses (see table 5 and FIG. 28).

Final Volume Reduction by Using the AutoMACS Column

Figure 29:
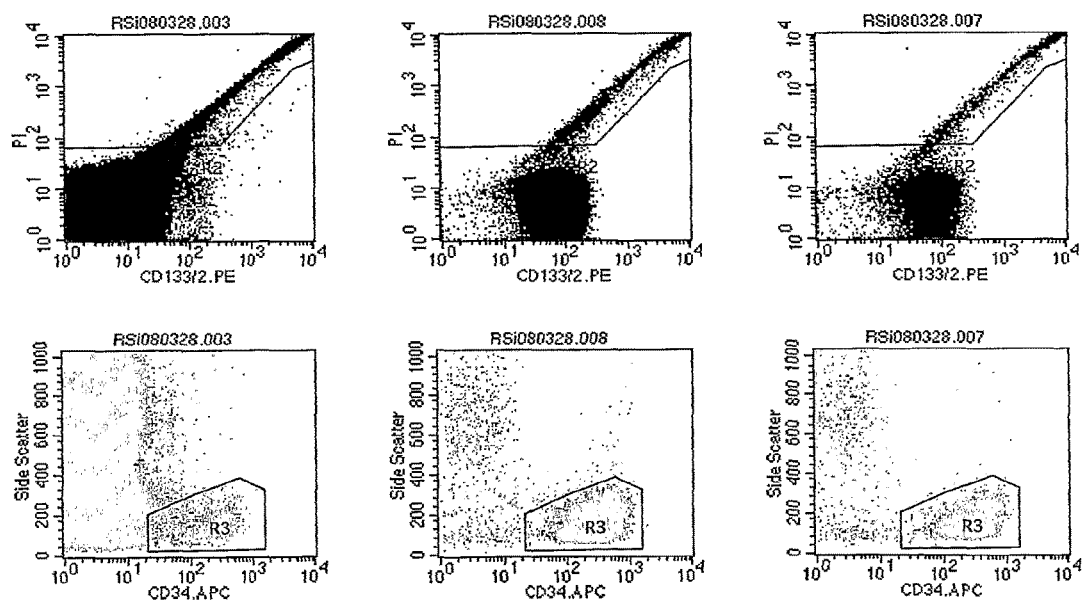

After elution from the CliniMACS column CD133+ cells can be loaded on an autoMACS column at a rate of 4 ml/min. Afterwards retained CD133+ cells are eluted in 4 ml from the autoMACS column. This method was tested by enrichment of CD133+ cells from bone marrow. Enriched dells were determined by FACS analyses (see table 6 and FIG. 29).

TABLE 3

Direct elution of the CD133+ cells in 20 ml.

| Start volume [ml] | Starting frequency CD133+ | Final purity CD133+ | CD133− log depletion | Final cell number CD133+ | CD133+ yield* |
|---|---|---|---|---|---|
| 91 | 0.39% | 82.95% | 3.4 | 2.89E6 | 49.57% |
| 86 | 0.67% | 66.99% | 2.8 | 5.72E6 | 56.67% |
| 129 | 0.31% | 82.6% | 3.4 | 4.11E6 | 43.42% |
| 57 | 0.76% | 59.18% | 2.3 | 5.1E6 | 72.24% |
| 61 | 0.14% | 74.72% | 3.2 | 4.25E5 | 84.32% |
| 114 | 0.37% | 88.19% | 3.4 | 1.79E6 | 50.08% |
| 77 | 0.74% | 83.5% | 3 | 2.12E6 | 58.56% |

TABLE 4

Direct elution of the CD133+ cells in 6 ml.

| Start volume [ml] | Starting frequency CD133+ | Final purity CD133+ | CD133− log depletion | Final cell number CD133+ | CD133+ yield* |
|---|---|---|---|---|---|
| 87 | 0.67% | 62.79% | 2.7 | 2.78E6 | 51.22% |
| 129 | 0.31% | 81.12% | 3.6 | 1.25E6 | 33.6% |
| 128 | 0.66% | 57.25% | 2.6 | 2.31E6 | 26.86% |

TABLE 5

Concentration of the CD133 + cells by filtration after magnetic separation.

| Start volume/ final volume [ml] | Starting frequency CD133+ | Final purity CD133+ | CD133− log depletion | Final cell number CD133+ | CD133+ yield* |
|---|---|---|---|---|---|
| 91/3.79 | 0.39% | 66.08% | 1.2 | 6.27E5 | 25.3% |
| 86/3.67 | 0.67% | 60.1% | 1.5 | 1.59E6 | 31.6% |
| 129/3.66 | 0.31% | 76.04% | 1.2 | 8.18E5 | 26.6% |

TABLE 6

Concentration of the CD133 + cells by using the AutoMACS column.

| Start volume/ final volume [ml] | Starting frequency CD133+ | Final purity CD133+ | CD133− log depletion | Final cell number CD133+ | CD133+ yield* |
|---|---|---|---|---|---|
| 57/2.78 | 0.76% | 71.3% | 0.9 | 2.35E6 | 39.9% |
| 61/5.68 | 0.14% | 82.84% | 0.4 | 1.73E5 | 43.1% |
| 114/5.64 | 0.37% | 93.57% | 0.7 | 8.51E5 | 28.6% |

(*calculated in relation to CD133+ cells recovered in all bags)

The invention claimed is:

1. An apparatus configured for fractionating a blood or bone marrow sample in a sterile tubing set installed on the apparatus, wherein the tubing set comprises:
   a) a first connecting member configured to receive the sample and deliver the sample to a rotatable container,
   b) said rotatable container installed in a centrifuge in the apparatus, wherein the rotatable container contains at least one processing chamber and is configured to rotate about an axis and thereby to apply centrifugal force to a blood or bone marrow sample in the chamber so as to separate cells from the sample according to a first cell characteristic;
   c) a second connecting member configured to receive a selected subset of cells that has been separated from the sample by the rotatable container and to deliver the subset to a cell separation column;
   d) said separation column installed in a column holder in the apparatus, which is configured such that cells can be delivered to the cell separation column by the second connecting member; and
   e) a third connecting member configured to recover cells that have been selected by the cell separation column in the holder according to a second cell characteristic and to deliver the selected cells to a product collection container;
   wherein the apparatus is configured to operate so that a sample is processed from the first connecting member of the tubing set through the rotatable container in the centrifuge and through the cell separation column in the column holder and a product thereof is delivered into the product collection container while maintaining sterility of the product throughout all the aforelisted components of the tubing set.

2. The apparatus of claim 1, wherein the rotatable container comprises a detection window that is positioned substantially perpendicular to the axis of rotation such that a detector can monitor separation of cells in the chamber radially through and along the detection window.

3. The apparatus of claim 2, wherein a prism or a mirror is positioned radially along the detection window.

4. The apparatus of claim 1, wherein the first connecting member is connected to the processing chamber of the rotatable container by way of a central line that passes through rotational seals and along the axis.

5. The apparatus of claim 1, wherein the first and the second connecting members are connected to the processing chamber of the rotatable container by way of an inner line and an outer line that both pass through rotational seals and along the axis.

6. The apparatus of claim 2, further comprising a detector that is positioned so as to receive light that has been provided by a light source and has passed through a portion of the sample along a radial cross-section of the rotatable container.

7. The apparatus of claim 6, configured so that upon processing of a blood sample in the rotatable container, the detector can detect an outer ring of erythrocytes and granulocytes, a ring of peripheral blood mononuclear cells, and an inner ring of platelets.

8. The apparatus of claim 1, whereby the rotatable container comprises an inlet and an outlet port configured for exchange of air or gas inside the chamber so as to support culturing of cells in the chamber under sterile conditions without stopping the centrifuge.

9. The apparatus of claim 1, wherein the rotatable container comprises a plurality of parallel surfaces that are perpendicular to the rotational axis, wherein the surfaces are configured so that cells can be cultured upon them.

10. The apparatus of claim 1, wherein the first characteristic is cell density.

11. The apparatus of claim 9, wherein the first characteristic is affinity for a surface, and the rotatable container is constructed such that cells adhering to the surfaces may be separated while the chamber is rotating from cells with lesser affinity for the surfaces.

12. The apparatus of claim 1, comprising fluid circuitry configured to distribute a plurality of different cell fractions from the rotatable container and/or the cell separation column each to a different cell collection container.

13. The apparatus of claim 1, comprising fluid circuitry configured to pass cells multiple times over a cell separation column in the column holder.

14. The apparatus of claim 1, wherein the cell separation column is configured to separate hematopoietic cells from the rotatable container according to a characteristic of a subset of cells in a sample, or a label that is attached selectively to a subset of cells in the sample.

15. The apparatus of claim 14, wherein the cell separation column is a magnetic separation column configured so that cells labeled with a magnetic label will be retained by the column, and cells that are not so labeled will pass through the column.

16. The apparatus of claim 14, wherein the cell separation column is configured with a ferromagnetic matrix that can be rendered magnetic to retain cells labeled with a magnetic particle, and then can be rendered non-magnetic to release cells that have been retained.

17. An apparatus configured for fractionating a cell sample, the apparatus comprising:
(a) a sample processing unit that includes a first holder sized and shaped to reversibly secure a rotatable container, and a drive configured to rotate such a rotatable container when secured in the first holder, thereby applying centrifugal force to a blood or bone marrow sample in the container so as to separate different cell types in the sample according to a first cell characteristic;
(b) a sample separation unit that includes a second holder sized and shaped to reversibly secure a cell separation column, the sample separation unit being configured to operate such a cell separation column secured in the second holder so as to separate different cell types according to a second cell characteristic;
wherein the apparatus is configured to be operatively installed with a sterile tubing set that comprises:
  (i) a first connector configured for sterile connection of a sample container;
  (ii) a rotatable container that operatively fits in the sample processing unit;
  (iii) a first inlet port configured to deliver a first cell population into the rotatable container for separation;
  (iv) a first outlet port configured to receive a selected subset of cells from the first cell population that have been separated by the rotatable container;
  (v) a second inlet port configured to deliver a second cell population onto a cell separation column secured in the second holder;
  (vi) said cell separation column which operatively fits in the sample separation unit;
  (vii) a second outlet port configured to receive a subset of cells that has been selected from the second cell population by the cell separation column; and
  (viii) a second connector configured for sterile connection to a product collection container;
so that when a cell sample is supplied into the tubing set through the first connector, the sample can be processed by the apparatus in the rotatable container secured in the first holder and processed by the apparatus in the cell separation column secured in the second holder, following which a product therefrom can be delivered by the apparatus though the second connector into a product collection container, whereby cells in the product have been kept sterile during processing in the sterile tubing set.

18. A system comprising the apparatus of claim 17 installed with the sterile tubing set such that the rotatable container is secured by and connected to the first holder and the cell separation column is secured by and connected to the second holder, wherein the cell separation column is configured to separate hematopoietic cells received from the rotatable container into one or more subsets according to a label that is attached selectively to a subset of cells in the sample.

19. The system of claim 18, wherein the rotatable container comprises an axis of rotation, and first inlet port and the first outlet port are connected to a processing chamber in the rotatable container by way of an inner line and an outer line that both pass through rotational seals and along the axis of rotation.

20. A method for fractionating a cell sample using the apparatus of claim 17, comprising:
a) installing said sterile tubing set on the apparatus so that the rotatable container is secured to the first holder and the cell separation column is secured to the second holder;
b) delivering a sample through the first connecting member into the rotatable container,
c) causing the rotatable container to rotate, thereby applying centrifugal force to the sample so as to separate different cell types from the sample according to a first characteristic;

d) processing a cell type separated by the rotatable container in the cell separation column so as to select cells therefrom according to a second characteristic; and e) recovering cells from the apparatus selected as having both the first and the second characteristics.

21. The method of claim 20, wherein the first characteristic is a cell density of a particular hematopoietic cell type.

22. The method of claim 20, wherein the second characteristic comprises the presence or absence of a cell-surface marker selected from CD34, CD133, CD14, CD304, CD4, and CD8.

23. The method of claim 20, wherein the second characteristic is labeled with a magnetic particle.

* * * * *